United States Patent
Giroux

(10) Patent No.: US 9,943,095 B2
(45) Date of Patent: *Apr. 17, 2018

(54) PRODUCTION OF HIGH QUALITY DURUM WHEAT HAVING INCREASED AMYLOSE CONTENT

(71) Applicant: Montana State University, Bozeman, MT (US)

(72) Inventor: Michael J. Giroux, Bozeman, MT (US)

(73) Assignee: Montana State University, Bozeman, MT (US)

( * ) Notice: Subject to any disclaimer, the term of this patent is extended or adjusted under 35 U.S.C. 154(b) by 124 days.

This patent is subject to a terminal disclaimer.

(21) Appl. No.: 14/438,117

(22) PCT Filed: Oct. 23, 2013

(86) PCT No.: PCT/US2013/066373

§ 371 (c)(1),
(2) Date: Apr. 23, 2015

(87) PCT Pub. No.: WO2014/066497

PCT Pub. Date: May 1, 2014

(65) Prior Publication Data

US 2015/0264875 A1 Sep. 24, 2015

Related U.S. Application Data

(60) Provisional application No. 61/736,136, filed on Dec. 12, 2012, provisional application No. 61/717,357, filed on Oct. 23, 2012.

(51) Int. Cl.
| | |
|---|---|
| *C12N 15/01* | (2006.01) |
| *A01H 1/06* | (2006.01) |
| *A01H 5/10* | (2006.01) |
| *A23L 29/212* | (2016.01) |
| *A23L 7/10* | (2016.01) |
| *C07K 14/415* | (2006.01) |
| *C12N 15/82* | (2006.01) |
| *A23L 7/109* | (2016.01) |
| *A23L 33/21* | (2016.01) |

(52) U.S. Cl.
CPC ............ *A23L 7/198* (2016.08); *A01H 5/10* (2013.01); *A23L 7/10* (2016.08); *A23L 7/109* (2016.08); *A23L 29/212* (2016.08); *A23L 33/21* (2016.08); *C07K 14/415* (2013.01); *C12N 15/8245* (2013.01)

(58) Field of Classification Search
None
See application file for complete search history.

(56) References Cited

U.S. PATENT DOCUMENTS

| | | |
|---|---|---|
| 4,595,597 A | 6/1986 | Lenchin et al. |
| 6,570,008 B1 | 5/2003 | Broglie |
| 6,897,354 B1 | 5/2005 | Yamamori |
| 7,001,771 B1 | 2/2006 | Morell et al. |
| 7,001,939 B2 | 2/2006 | Yamamori |
| 7,700,826 B2 | 4/2010 | Morell et al. |
| 7,993,686 B2 | 8/2011 | Bird et al. |
| 9,439,447 B2 | 9/2016 | Giroux |
| 2002/0138876 A1 | 9/2002 | Block et al. |
| 2003/0106099 A1 | 6/2003 | Konzak et al. |
| 2006/0286186 A1 | 12/2006 | Bird |
| 2007/0044171 A1 | 2/2007 | Kovalic et al. |
| 2007/0118916 A1 | 5/2007 | Puzio et al. |
| 2009/0106863 A1 | 4/2009 | Frohberg et al. |
| 2010/0034953 A1 | 2/2010 | Frohberg |
| 2011/0070352 A1 | 3/2011 | Regina et al. |
| 2011/0281818 A1 | 11/2011 | Jenkins et al. |
| 2014/0199313 A1 | 4/2014 | Plesch et al. |
| 2014/0127388 A1 | 5/2014 | Giroux |
| 2017/0006815 A1 | 1/2017 | Giroux |

FOREIGN PATENT DOCUMENTS

| | | |
|---|---|---|
| EP | 0512249 A1 | 11/1992 |
| EP | 2183964 A1 | 5/2010 |
| WO | WO 2005/001098 | 1/2005 |
| WO | WO 2014/066497 A2 | 5/2014 |
| WO | WO 2017/008001 A1 | 1/2017 |

OTHER PUBLICATIONS

Slade et al. Nature Biotechnology 23(1): 75-81 (Jan. 2005).*
Martin et al. Cereal Chemistry 91(2): 176-182 (Mar. 2014).*
European Examination Report for EP 14113.159, dated May 3, 2016, 11 pages.
Craig et al., "Mutations in the gene encoding starch synthase II profoundly alter amylopectin structure in pea embryos," Plant Cell 10:413-426 (1998).
Hazard et al., "Induced Mutations in the Starch Branching Enzyme II (SBEII) Genes Increase Amylose and Resistant Starch Content in Durum Wheat," Crop Sci. 52:1754-1766 (2012).
Hogg et al., "Creation of a high-amylose durum wheat through mutagenesis of starch synthase II (SSIIa)," J. Cereal Science 57:377-383 (2013).
Kosar-Hashemi et al., "Multiple effects of the starch synthase II mutation in developing wheat endosperm," Funct. Plant Biol. 34:431-438 (2007).
Lafiandra et al., "Approaches for Modification of Starch Composition in Durum Wheat," Cereal Chem. 87:28-34 (2010).
Miura et al., "Genetic control of amylose content in wheat endosperm starch and differential effects of 3 Wx genes," Theoret. Appl. Genet. 89:276-280 (1994).

(Continued)

*Primary Examiner* — David T Fox

(74) *Attorney, Agent, or Firm* — Cooley LLP

(57) ABSTRACT

The present invention provides compositions and methods of altering/improving Durum wheat phenotypes. Furthermore, methods of breeding Durum wheat and/or other closely related species to produce plants having altered or improved phenotypes are provided.

27 Claims, 7 Drawing Sheets

(56) References Cited

OTHER PUBLICATIONS

Regina et al., "High-amylose wheat generated by RNA interference improves indices of large-bowel health in rats," Proc. Natl. Acad. Sci. USA 103:3546-3551 (2006).
Sestili et al., "Production of novel allelic variation for genes involved in starch biosynthesis through mutagenesis," Mol. Breeding 25:145-154 (2010).
Sestili et al., "Increasing the amylose content of durum wheat through silencing of the SBEIIa genes," BMC Plant Biol. 10:144 (2010).
Shimbata et al., "Mutations in wheat starch synthase II genes and PCR-based selection of a SGP-1 null line," Theoret. Appl. Genet. 111:1072-1079 (2005).
Yamamori et al., "Genetic elimination of a starch granule protein, SGP-1, of wheat generates an altered starch with apparent high amylose," Theoret. Appl. Genet. 101:21-29 (2000).
Yamamori et al., "Resistant starch and starch pasting properties of a starch synthase IIa-deficient wheat with apparent high amylose," Aust. J. Agr. Res. 57:531-535 (2006).
International Search Report for PCT/US2013/066373 dated May 20, 2014.
International Search Report for PCT/US2016/041478 dated Dec. 8, 2016.
Written Opinion for PCT/US2016/041478 dated Dec. 8, 2016.
Q2WGB1, UniProtKB entry Q2WGB1_WHEAT, Jan. 10, 2006 [online]. [Retrieved on Sep. 21, 2016]. Retrieved from the internet <URL:http://www.uniprot.org/uniprovQ2WGB1.txt> entire document.
Written Opinion for PCT/US2013/066373 dated May 20, 2014.
International Preliminary Report on Patentability for PCT/US2013/066373 dated Apr. 28, 2015.
Slade et al., "Development of high amylose wheat through TILLING", BMC Plant Biology, 12:69 (2012).
European Examination Report for EP 13848736.8-1358, dated May 3, 2016, 11 pages.

\* cited by examiner

SEQUENCE LISTING

```
<160> NUMBER OF SEQ ID NOS: 24

<210> SEQ ID NO 1
<211> LENGTH: 119
<212> TYPE: PRT
```

<213> ORGANISM: Triticum durum

<400> SEQUENCE: 1

Val Phe Val Cys Asn Asp Trp His Thr Gly Leu Leu Ala Cys Tyr Leu
1               5                   10                  15

Lys Ser Asn Tyr Gln Ser Asn Gly Ile Tyr Arg Thr Ala Lys Val Ala
            20                  25                  30

Phe Cys Ile His Asn Ile Ser Tyr Gln Gly Arg Phe Ser Phe Asp Asp
        35                  40                  45

Phe Ala Gln Leu Asn Leu Pro Asp Arg Phe Lys Ser Ser Phe Asp Phe
    50                  55                  60

Ile Asp Gly Tyr Asp Lys Pro Val Glu Gly Arg Lys Ile Asn Trp Met
65                  70                  75                  80

Lys Ala Gly Ile Leu Gln Ala Asp Lys Val Leu Thr Val Ser Pro Tyr
                85                  90                  95

Tyr Ala Glu Glu Leu Ile Ser Gly Glu Ala Arg Gly Cys Glu Leu Asp
            100                 105                 110

Asn Ile Met Arg Leu Thr Gly
        115

<210> SEQ ID NO 2
<211> LENGTH: 579
<212> TYPE: PRT
<213> ORGANISM: Triticum durum

<400> SEQUENCE: 2

Leu Val Thr Ser Gln Leu Ala Thr Ser Gly Thr Val Leu Gly Ile Thr
1               5                   10                  15

Asp Arg Phe Arg His Ala Gly Phe Gln Gly Val Arg Pro Arg Ser Pro
            20                  25                  30

Ala Asp Ala Pro Leu Gly Met Arg Thr Thr Gly Ala Ser Ala Ala Pro
        35                  40                  45

Lys Gln Gln Ser Arg Lys Ala His Arg Gly Thr Arg Arg Cys Leu Ser
    50                  55                  60

Met Val Val Arg Ala Thr Gly Ser Ala Gly Met Asn Leu Val Phe Val
65                  70                  75                  80

Gly Ala Glu Met Ala Pro Trp Ser Lys Thr Gly Gly Leu Gly Asp Val
                85                  90                  95

Leu Gly Gly Leu Pro Pro Ala Met Ala Ala Asn Gly His Arg Val Met
            100                 105                 110

Val Ile Ser Pro Arg Tyr Asp Gln Tyr Lys Asp Ala Trp Asp Thr Ser
        115                 120                 125

Val Val Ser Glu Ile Lys Val Ala Asp Glu Tyr Glu Arg Val Arg Tyr
    130                 135                 140

Phe His Cys Tyr Lys Arg Gly Val Asp Arg Val Phe Val Asp His Pro
145                 150                 155                 160

Cys Phe Leu Glu Lys Val Arg Gly Lys Thr Lys Glu Lys Ile Tyr Gly
                165                 170                 175

Pro Asp Ala Gly Thr Asp Tyr Glu Asp Asn Gln Leu Arg Phe Ser Leu
            180                 185                 190

Leu Cys Gln Ala Ala Leu Glu Ala Pro Arg Ile Leu Asp Leu Asn Asn
        195                 200                 205

Asn Pro Tyr Phe Ser Gly Pro Tyr Gly Glu Asp Val Val Phe Val Cys
    210                 215                 220

Asn Asp Trp His Thr Gly Leu Leu Ala Cys Tyr Leu Lys Ser Asn Tyr

-continued

```
                225                 230                 235                 240
        Gln Ser Ser Gly Ile Tyr Arg Thr Ala Lys Val Ala Phe Cys Ile His
                        245                 250                 255

Asn Ile Ser Tyr Gln Gly Arg Phe Ser Phe Asp Asp Phe Ala Gln Leu
                        260                 265                 270

Asn Leu Pro Asp Arg Phe Lys Ser Ser Phe Asp Phe Ile Asp Gly Tyr
                        275                 280                 285

Asp Lys Pro Val Glu Gly Arg Lys Ile Asn Trp Met Lys Ala Gly Ile
                        290                 295                 300

Leu Gln Ala Asp Lys Val Leu Thr Val Ser Pro Tyr Tyr Ala Glu Glu
        305                 310                 315                 320

Leu Ile Ser Gly Glu Ala Arg Gly Cys Glu Leu Asp Asn Ile Met Arg
                        325                 330                 335

Leu Thr Gly Ile Thr Gly Ile Val Asn Gly Met Asp Val Ser Glu Trp
                        340                 345                 350

Asp Pro Ala Lys Asp Lys Phe Leu Ala Ala Asn Tyr Asp Val Thr Thr
                        355                 360                 365

Ala Leu Glu Gly Lys Ala Leu Asn Lys Glu Ala Leu Gln Ala Glu Val
                        370                 375                 380

Gly Leu Pro Val Asp Arg Lys Val Pro Leu Val Ala Phe Ile Gly Arg
        385                 390                 395                 400

Leu Glu Glu Gln Lys Gly Pro Asp Val Met Ile Ala Ala Ile Pro Glu
                        405                 410                 415

Ile Leu Lys Glu Glu Asp Val Gln Ile Val Leu Leu Gly Thr Gly Lys
                        420                 425                 430

Lys Lys Phe Glu Arg Leu Leu Lys Ser Val Glu Glu Lys Phe Pro Ser
                        435                 440                 445

Lys Val Arg Ala Val Val Arg Phe Asn Ala Pro Leu Ala His Gln Met
                        450                 455                 460

Met Ala Gly Ala Asp Val Leu Ala Val Thr Ser Arg Phe Glu Pro Cys
        465                 470                 475                 480

Gly Leu Ile Gln Leu Gln Gly Met Arg Tyr Gly Thr Pro Cys Ala Cys
                        485                 490                 495

Ala Ser Thr Gly Gly Leu Val Asp Thr Ile Val Glu Gly Lys Thr Gly
                        500                 505                 510

Phe His Met Gly Arg Leu Ser Val Asp Cys Asn Val Val Glu Pro Ala
                        515                 520                 525

Asp Val Lys Lys Val Val Thr Thr Leu Lys Arg Ala Val Lys Val Val
                        530                 535                 540

Gly Thr Pro Ala Tyr His Glu Met Val Lys Asn Cys Met Ile Gln Asp
        545                 550                 555                 560

Leu Ser Trp Lys Gly Pro Ala Lys Asn Trp Glu Asp Val Leu Leu Glu
                        565                 570                 575

Leu Gly Val

<210> SEQ ID NO 3
<211> LENGTH: 2780
<212> TYPE: DNA
<213> ORGANISM: Triticum aestivum

<400> SEQUENCE: 3
cggaggacca acccgcgcat cgtaccatcg cccgccccga tcccggccgc cgccatgtcg      60
tcggcggtcg cgtccgccgc gtccttcctc gcgctcgcct ccgcctcccc cgggagatca     120
```

```
cgcaggcggg cgagggtgag cgcgccgcca ccccacgccg gggccggcag gctgcactgg    180
ccgccgtggc cgccgcagcg cacggctcgc gacggaggtg tggccgcgcg cgccgccggg    240
aagaaggacg cgagggtcga cgacgacgcc gcgtccgcga ggcagccccg cgcacgccgc    300
ggtggcgccg ccaccaaggt cgcggagcgg agggatcccg tcaagacgct cgatcgcgac    360
gccgcggaag gtggcgcgcc ggcaccgccg gcaccgaggc aggacgccgc ccgtccaccg    420
agtatgaacg gcacgccggt gaacggtgag aacaaatcta ccggcggcgg cggcgcgacc    480
aaagacagcg ggctgcccgc acccgcacgc gcgccccatc cgtcgaccca gaacagagta    540
ccagtgaacg gtgaaaacaa agctaacgtc gcctcgccgc cgacgagcat agccgaggtc    600
gtggctccgg attccgcagc taccatttcc atcagtgaca aggcgccgga gtccgttgtc    660
ccagccgaga agccgccgcc gtcgtccggc tcaaatttcg tggtctcggc ttctgctccc    720
aggctggaca ttgacagcga tgttgaacct gaactgaaga agggtgcggt catcgtcgaa    780
gaagctccaa acccaaaggc tctttcgccg cctgcagccc ccgctgtaca agaagacctt    840
tgggacttca agaaatacat tggcttcgag gagcccgtgg aggccaagga tgatggctgg    900
gctgttgcag atgatgcggg ctcctttgaa catcaccaga accatgattc cggacctttg    960
gcaggggaga cgtcatgaa cgtggtcgtc gtggctgctg aatgttctcc ctggtgcaaa   1020
acaggtggtc ttggagatgt tgcgggtgct ctgcccaagg ctttggcaaa gagaggacat   1080
cgtgttatgg ttgtggtacc aaggtatggg gactatgagg aagcctacga tgtcggagtc   1140
cgaaaatact acaaggctgc tggacaggat atggaagtga attatttcca tgcttatatc   1200
gatgagttga ttttgtgtt cattgacgct cctatcttcc gacaccgtca ggaagacatt   1260
tatgggggca gcagacagga aattatgaag cgcatgattt tgttctgcaa ggccgctgtc   1320
gaggttcctt ggcacgttcc atgcggcggt gtcccttatg gggatggaaa tctggtgttt   1380
attgcaaatg attggcacac ggcactcctg cctgtctatc tgaaagcata ttacagggac   1440
catggtttga tgcagtacac tcggtccatt atggtgatac ataacatcgc gcaccagggc   1500
cgtggcccag tagatgaatt cccgttcacc gagttgcctg agcactacct ggaacacttc   1560
agactgtacg accccgtggg tggtgagcac gccaactact cgccgccgg cctgaagatg   1620 gcggaccagg ttgtcgtggt gagccccggg tacctgtggg agctcaagac ggtggagggc   1680
ggctgggggc ttcacgacat catacggcag aacgactgga agaccgcgg catcgtcaac   1740 ggcatcgaca acatggagtg gaaccccgag gtggacgtcc acctccagtc ggacggctac   1800
accaacttct ccctgagcac gctggactcc ggcaagcggc agtgcaagga ggccctgcag   1860
cgcgagctgg gcctgcaggt ccgcgccgac gtgccgctgc tcggcttcat cggccgcctg   1920
gacgggcaga agggcgtgga gatcatcgcg gacgccatgc cctggatcgt gagccaggac   1980
gtgcagctgg tcatgctggg caccggccgc cacgacctgg agagcatgct gcggcacttc   2040
gagcgggagc accacgacaa ggtgcgcggg tgggtggggt tctccgtgcg cctggcgcac   2100
cggatcacgg cgggcgccga cgcgctcctc atgccctccc ggttcgagcc gtgcgggctg   2160
aaccagctct acgccatggc ctacggcacc gtcccgtcg tgcacgccgt cggcgggctg   2220
agggacaccg tgccgccgtt cgacccctc aaccactccg gcctcgggtg gacgttcgac   2280
cgcgccgagg cgcacaagct gatcgaggcg ctcgggcact gcctccgcac ctaccgggac   2340
tacaaggaga gctggagggg cctccaggag cgcggcatgt cgcaggactt cagctgggag   2400
catgccgcca agctctacga ggacgtcctc ctcaaggcca gtaccagtg gtgaacgcta   2460 gctgctagcc gctccagccc cgcatgcgtg catgcatgag agggtggaac tgcgcattgc   2520
```

-continued

```
gcccgcagga acgtgccatc cttctcgatg ggagcgccgg catccgcgag gtgcagtgac    2580
atgagaggtg tgtgtggttg agacgctgat tccgatctcg atctggtccg tagcagagta    2640
gagcggacgt agggaagcgc tccttgttgc aggtatatgg gaatgttgtc aacttggtat    2700
tgtagtttgc tatgttgtat gcgttattac aatgttgtta cttattcttg ttaaaaaaaa    2760
aaaaaaaaaa aaaaaaaaa                                                 2780
```

<210> SEQ ID NO 4
<211> LENGTH: 799
<212> TYPE: PRT
<213> ORGANISM: Triticum aestivum

<400> SEQUENCE: 4

```
Met Ser Ser Ala Val Ala Ser Ala Ala Ser Phe Leu Ala Leu Ala Ser
1               5                   10                  15

Ala Ser Pro Gly Arg Ser Arg Arg Ala Arg Val Ser Ala Pro Pro
            20                  25                  30

Pro His Ala Gly Ala Gly Arg Leu His Trp Pro Pro Trp Pro Pro Gln
            35                  40                  45

Arg Thr Ala Arg Asp Gly Val Ala Ala Arg Ala Gly Lys Lys
    50                  55                  60

Asp Ala Arg Val Asp Asp Ala Ala Ser Ala Arg Gln Pro Arg Ala
65                  70                  75                  80

Arg Arg Gly Gly Ala Ala Thr Lys Val Ala Glu Arg Arg Asp Pro Val
                85                  90                  95

Lys Thr Leu Asp Arg Asp Ala Ala Glu Gly Ala Pro Ala Pro
            100                 105                 110

Ala Pro Arg Gln Asp Ala Ala Arg Pro Pro Ser Met Asn Gly Thr Pro
            115                 120                 125

Val Asn Gly Glu Asn Lys Ser Thr Gly Gly Gly Ala Thr Lys Asp
    130                 135                 140

Ser Gly Leu Pro Ala Pro Ala Arg Ala Pro His Pro Ser Thr Gln Asn
145                 150                 155                 160

Arg Val Pro Val Asn Gly Glu Asn Lys Ala Asn Val Ala Ser Pro Pro
                165                 170                 175

Thr Ser Ile Ala Glu Val Val Ala Pro Asp Ser Ala Ala Thr Ile Ser
            180                 185                 190

Ile Ser Asp Lys Ala Pro Glu Ser Val Val Pro Ala Glu Lys Pro Pro
        195                 200                 205

Pro Ser Ser Gly Ser Asn Phe Val Val Ser Ala Ser Ala Pro Arg Leu
    210                 215                 220

Asp Ile Asp Ser Asp Val Glu Pro Glu Leu Lys Lys Gly Ala Val Ile
225                 230                 235                 240

Val Glu Glu Ala Pro Asn Pro Lys Ala Leu Ser Pro Pro Ala Ala Pro
                245                 250                 255

Ala Val Gln Glu Asp Leu Trp Asp Phe Lys Lys Tyr Ile Gly Phe Glu
            260                 265                 270

Glu Pro Val Glu Ala Lys Asp Asp Gly Trp Ala Val Ala Asp Asp Ala
        275                 280                 285

Gly Ser Phe Glu His His Gln Asn His Asp Ser Gly Pro Leu Ala Gly
    290                 295                 300

Glu Asn Val Met Asn Val Val Val Ala Ala Glu Cys Ser Pro Trp
305                 310                 315                 320
```

```
Cys Lys Thr Gly Gly Leu Gly Asp Val Ala Gly Ala Leu Pro Lys Ala
            325                 330                 335

Leu Ala Lys Arg Gly His Arg Val Met Val Val Pro Arg Tyr Gly
        340                 345                 350

Asp Tyr Glu Ala Tyr Asp Val Gly Val Arg Lys Tyr Tyr Lys Ala
        355                 360                 365

Ala Gly Gln Asp Met Glu Val Asn Tyr Phe His Ala Tyr Ile Asp Gly
        370                 375                 380

Val Asp Phe Val Phe Ile Asp Ala Pro Ile Phe Arg His Arg Gln Glu
385                 390                 395                 400

Asp Ile Tyr Gly Gly Ser Arg Gln Glu Ile Met Lys Arg Met Ile Leu
            405                 410                 415

Phe Cys Lys Ala Ala Val Glu Val Pro Trp His Val Pro Cys Gly Gly
            420                 425                 430

Val Pro Tyr Gly Asp Gly Asn Leu Val Phe Ile Ala Asn Asp Trp His
            435                 440                 445

Thr Ala Leu Leu Pro Val Tyr Leu Lys Ala Tyr Tyr Arg Asp His Gly
        450                 455                 460

Leu Met Gln Tyr Thr Arg Ser Ile Met Val Ile His Asn Ile Ala His
465                 470                 475                 480

Gln Gly Arg Gly Pro Val Asp Glu Phe Pro Phe Thr Glu Leu Pro Glu
            485                 490                 495

His Tyr Leu Glu His Phe Arg Leu Tyr Asp Pro Val Gly Gly Glu His
            500                 505                 510

Ala Asn Tyr Phe Ala Ala Gly Leu Lys Met Ala Asp Gln Val Val Val
            515                 520                 525

Val Ser Pro Gly Tyr Leu Trp Glu Leu Lys Thr Val Glu Gly Gly Trp
        530                 535                 540

Gly Leu His Asp Ile Ile Arg Gln Asn Asp Trp Lys Thr Arg Gly Ile
545                 550                 555                 560

Val Asn Gly Ile Asp Asn Met Glu Trp Asn Pro Glu Val Asp Val His
            565                 570                 575

Leu Gln Ser Asp Gly Tyr Thr Asn Phe Ser Leu Ser Thr Leu Asp Ser
        580                 585                 590

Gly Lys Arg Gln Cys Lys Glu Ala Leu Gln Arg Glu Leu Gly Leu Gln
        595                 600                 605

Val Arg Ala Asp Val Pro Leu Leu Gly Phe Ile Gly Arg Leu Asp Gly
        610                 615                 620

Gln Lys Gly Val Glu Ile Ile Ala Asp Ala Met Pro Trp Ile Val Ser
625                 630                 635                 640

Gln Asp Val Gln Leu Val Met Leu Gly Thr Gly Arg His Asp Leu Glu
            645                 650                 655

Ser Met Leu Arg His Phe Glu Arg Glu His His Asp Lys Val Arg Gly
            660                 665                 670

Trp Val Gly Phe Ser Val Arg Leu Ala His Arg Ile Thr Ala Gly Ala
        675                 680                 685

Asp Ala Leu Leu Met Pro Ser Arg Phe Glu Pro Cys Gly Leu Asn Gln
        690                 695                 700

Leu Tyr Ala Met Ala Tyr Gly Thr Val Pro Val Val His Ala Val Gly
705                 710                 715                 720

Gly Leu Arg Asp Thr Val Pro Pro Phe Asp Pro Phe Asn His Ser Gly
            725                 730                 735

Leu Gly Trp Thr Phe Asp Arg Ala Glu Ala His Lys Leu Ile Glu Ala
```

```
                 740                 745                 750
Leu Gly His Cys Leu Arg Thr Tyr Arg Asp Tyr Lys Glu Ser Trp Arg
                755                 760                 765
Gly Leu Gln Glu Arg Gly Met Ser Gln Asp Phe Ser Trp Glu His Ala
            770                 775                 780
Ala Lys Leu Tyr Glu Asp Val Leu Leu Lys Ala Lys Tyr Gln Trp
785                 790                 795
```

<210> SEQ ID NO 5
<211> LENGTH: 2793
<212> TYPE: DNA
<213> ORGANISM: Triticum aestivum

<400> SEQUENCE: 5

| | | | | | |
|---|---|---|---|---|---|
| gcactccagt | ccagtccagc | ccactgccgc | gctactcccc | actcccactg | ccaccacctc | 60 |
| cgcctgcgcc | gcgctctggg | cggaccaacc | cgcgcatcgt | atcacgatca | cccaccccga | 120 |
| tcccggccgc | cgccatgtcg | tcggcggtcg | cgtccgccgc | gtccttcctc | cgctcgcgt | 180 |
| ccgcctcccc | cgggagatca | cggaggagga | cgagggtgag | cgcgtcgcca | ccccacaccg | 240 |
| gggctggcag | gttgcactgg | ccgccgtcgc | cgccgcagcg | cacggctcgc | gacggagcag | 300 |
| tggccgcgcg | cgccgccggg | aagaaggacg | cggggatcga | cgacgccgcg | cccgcgaggc | 360 |
| agccccgcgc | actccgcggt | ggcgccgcca | ccaaggttgc | ggagcggagg | gatcccgtca | 420 |
| agacgctcga | tcgcgacgcc | gcggaaggtg | gcgcgccgtc | cccgccggca | ccgaggcagg | 480 |
| aggacgcccg | tctgccgagc | atgaacggca | tgccggtgaa | cggtgaaaac | aaatctaccg | 540 |
| gcggcggcgg | cgcgactaaa | gacagcgggc | tgcccgcacc | cgcacgcgcg | ccccagccgt | 600 |
| cgagccagaa | cagagtaccg | gtgaatggtg | aaaacaaagc | taacgtcgcc | tcgccgccga | 660 |
| cgagcatagc | cgaggtcgcg | gctccggatc | ccgcagctac | catttccatc | agtgacaagg | 720 |
| cgccagagtc | cgttgtccca | gccgagaagg | cgccgccgtc | gtccggctca | aatttcgtgc | 780 |
| cctcggcttc | tgctcccggg | tctgacactg | tcagcgacgt | ggaacttgaa | ctgaagaagg | 840 |
| gtgcggtcat | tgtcaaagaa | gctccaaacc | caaaggctct | tcgccgcct | gcagcacccg | 900 |
| ctgtacaaca | agacctttgg | gacttcaaga | aatacattgg | tttcgaggag | cccgtggagg | 960 |
| ccaaggatga | tggccgggct | gttgcagatg | atgcgggctc | cttcgaacac | caccagaatc | 1020 |
| acgattccgg | gcctttggca | ggggagaacg | tcatgaacgt | ggtcgtcgtg | gctgctgaat | 1080 |
| gttctccctg | gtgcaaaaca | ggtggtcttg | gagatgttgc | cggtgctttg | cccaaggctt | 1140 |
| tggcgaagag | aggacatcgt | gttatggttg | tggtaccaag | gtatgggac | tatgaggaag | 1200 |
| cctacgatgt | cggagtccga | aaatactaca | aggctgctgg | acaggatatg | gaagtgaatt | 1260 |
| atttccatgc | ttatatcgat | ggagttgatt | ttgtgttcat | tgacgctcct | ctcttccgac | 1320 |
| accgccagga | agacatttat | gggggcagca | gacaggaaat | tatgaagcgc | atgattttgt | 1380 |
| tctgcaaggc | cgctgtcgag | gttccatggc | acgttccatg | cggcggtgtc | ccttatgggg | 1440 |
| atggaaatct | ggtgtttatt | gcaaatgatt | ggcacacggc | actcctgcct | gtctatctga | 1500 |
| aagcatatta | cagggaccat | ggtttgatgc | agtacactcg | gtccattatg | gtgatacata | 1560 |
| acatcgctca | ccagggccgt | ggcccagtag | atgagttccc | gttcaccgag | ttgcctgagc | 1620 |
| actacctgga | acacttcaga | ctgtacgacc | ccgtgggtgg | tgaacacgcc | aactacttcg | 1680 |
| ccgccggcct | gaagatggcg | gaccaggttg | tcgtcgtgag | cccggggtac | ctgtgggagc | 1740 |
| tgaagacggt | ggagggcggc | tgggggcttc | acgacatcat | acggcagaac | gactggaaga | 1800 |

-continued

```
cccgcggcat cgtgaacggc atcgacaaca tggagtggaa ccccgaggtg gacgtccacc    1860
tcaagtcgga cggctacacc aacttctccc tggggacgct ggactccggc aagcggcagt    1920
gcaaggaggc cctgcagcgg gagctgggcc tgcaggtccg cggcgacgtg ccgctgctcg    1980
gcttcatcgg gcgcctggac gggcagaagg gcgtggagat catcgcggac gcgatgccct    2040
ggatcgtgag ccaggacgtg cagctggtca tgctgggcac cgggcgccac gacctggagg    2100
gcatgctgcg gcacttcgag cgggagcacc acgacaaggt gcgcgggtgg gtggggttct    2160
ccgtgcggct ggcgcaccgg atcacggccg gcgccgacgc gctcctcatg ccctcccggt    2220
tcgagccgtg cggactgaac cagctctacg ccatggccta cggcaccgtc ccgtcgtgc     2280 atgccgtcgg cggcctgagg gacaccgtgc cgccgttcga ccccttcaac cactccgggc    2340
tcgggtggac gttcgaccgc gcagaggcgc agaagctgat cgaggcgctc gggcactgcc    2400
tccgcaccta ccgggactac aaggagagct gggggggct ccaggagcgc ggcatgtcgc     2460
aggacttcag ctgggagcat gccgccaagc tctacgagga cgtcctcgtc aaggccaagt    2520
accagtggtg aacgctagct gctagccggt ccagccccgc atgcgtgcat gacaggatgg    2580
aattgcgcat tgcgcacgca ggaatgtgcc atggagcgcc ggcatccgcg aagtacagtg    2640
acatgaggtg tgtgtggttg agacgctgat tccgatctgg tccgtagcag agtagagcgg    2700
aggtagggaa gcgctccttg ttacaggtat atgggaatgt tgttaacttg gtattgtaat    2760
ttgttatgtt gtgtgcatta ttacaaaggg caa                                 2793
```

<210> SEQ ID NO 6
<211> LENGTH: 798
<212> TYPE: PRT
<213> ORGANISM: Triticum aestivum

<400> SEQUENCE: 6

```
Met Ser Ser Ala Val Ala Ser Ala Ala Ser Phe Leu Ala Leu Ala Ser
1               5                   10                  15

Ala Ser Pro Gly Arg Ser Arg Arg Thr Arg Val Ser Ala Ser Pro
            20                  25                  30

Pro His Thr Gly Ala Gly Arg Leu His Trp Pro Pro Ser Pro Pro Gln
        35                  40                  45

Arg Thr Ala Arg Asp Gly Ala Val Ala Arg Ala Ala Gly Lys Lys
    50                  55                  60

Asp Ala Gly Ile Asp Asp Ala Ala Pro Ala Arg Gln Pro Arg Ala Leu
65                  70                  75                  80

Arg Gly Gly Ala Ala Thr Lys Val Ala Glu Arg Arg Asp Pro Val Lys
                85                  90                  95

Thr Leu Asp Arg Asp Ala Ala Glu Gly Gly Ala Pro Ser Pro Ala
            100                 105                 110

Pro Arg Gln Glu Asp Ala Arg Leu Pro Ser Met Asn Gly Met Pro Val
        115                 120                 125

Asn Gly Glu Asn Lys Ser Thr Gly Gly Gly Ala Thr Lys Asp Ser
    130                 135                 140

Gly Leu Pro Ala Pro Ala Arg Ala Pro Gln Pro Ser Ser Gln Asn Arg
145                 150                 155                 160

Val Pro Val Asn Gly Glu Asn Lys Ala Asn Val Ala Ser Pro Thr
                165                 170                 175

Ser Ile Ala Glu Val Ala Ala Pro Asp Pro Ala Ala Thr Ile Ser Ile
            180                 185                 190

Ser Asp Lys Ala Pro Glu Ser Val Val Pro Ala Glu Lys Ala Pro Pro
```

-continued

```
             195                 200                 205
Ser Ser Gly Ser Asn Phe Val Pro Ser Ala Ala Pro Gly Ser Asp
    210                 215                 220
Thr Val Ser Asp Val Glu Leu Glu Leu Lys Lys Gly Ala Val Ile Val
225                 230                 235                 240
Lys Glu Ala Pro Asn Pro Lys Ala Leu Ser Pro Pro Ala Ala Pro Ala
                245                 250                 255
Val Gln Gln Asp Leu Trp Asp Phe Lys Lys Tyr Ile Gly Phe Glu Glu
                260                 265                 270
Pro Val Glu Ala Lys Asp Asp Gly Arg Ala Val Ala Asp Asp Ala Gly
                275                 280                 285
Ser Phe Glu His His Gln Asn His Asp Ser Gly Pro Leu Ala Gly Glu
                290                 295                 300
Asn Val Met Asn Val Val Val Ala Ala Glu Cys Ser Pro Trp Cys
305                 310                 315                 320
Lys Thr Gly Gly Leu Gly Asp Val Ala Gly Leu Pro Lys Ala Leu
                325                 330                 335
Ala Lys Arg Gly His Arg Val Met Val Val Pro Arg Tyr Gly Asp
                340                 345                 350
Tyr Glu Glu Ala Tyr Asp Val Gly Val Arg Lys Tyr Tyr Lys Ala Ala
                355                 360                 365
Gly Gln Asp Met Glu Val Asn Tyr Phe His Ala Tyr Ile Asp Gly Val
                370                 375                 380
Asp Phe Val Phe Ile Asp Ala Pro Leu Phe Arg His Arg Gln Glu Asp
385                 390                 395                 400
Ile Tyr Gly Gly Ser Arg Gln Glu Ile Met Lys Arg Met Ile Leu Phe
                405                 410                 415
Cys Lys Ala Ala Val Glu Val Pro Trp His Val Pro Cys Gly Gly Val
                420                 425                 430
Pro Tyr Gly Asp Gly Asn Leu Val Phe Ile Ala Asn Asp Trp His Thr
                435                 440                 445
Ala Leu Leu Pro Val Tyr Leu Lys Ala Tyr Tyr Arg Asp His Gly Leu
                450                 455                 460
Met Gln Tyr Thr Arg Ser Ile Met Val Ile His Asn Ile Ala His Gln
465                 470                 475                 480
Gly Arg Gly Pro Val Asp Glu Phe Pro Phe Thr Glu Leu Pro Glu His
                485                 490                 495
Tyr Leu Glu His Phe Arg Leu Tyr Asp Pro Val Gly Gly Glu His Ala
                500                 505                 510
Asn Tyr Phe Ala Ala Gly Leu Lys Met Ala Asp Gln Val Val Val Val
                515                 520                 525
Ser Pro Gly Tyr Leu Trp Glu Leu Lys Thr Val Glu Gly Gly Trp Gly
                530                 535                 540
Leu His Asp Ile Ile Arg Gln Asn Asp Trp Lys Thr Arg Gly Ile Val
545                 550                 555                 560
Asn Gly Ile Asp Asn Met Glu Trp Asn Pro Glu Val Asp Val His Leu
                565                 570                 575
Lys Ser Asp Gly Tyr Thr Asn Phe Ser Leu Gly Thr Leu Asp Ser Gly
                580                 585                 590
Lys Arg Gln Cys Lys Glu Ala Leu Gln Arg Glu Leu Gly Leu Gln Val
                595                 600                 605
Arg Gly Asp Val Pro Leu Leu Gly Phe Ile Gly Arg Leu Asp Gly Gln
                610                 615                 620
```

```
Lys Gly Val Glu Ile Ile Ala Asp Ala Met Pro Trp Ile Val Ser Gln
625                 630                 635                 640

Asp Val Gln Leu Val Met Leu Gly Thr Gly Arg His Asp Leu Glu Gly
            645                 650                 655

Met Leu Arg His Phe Glu Arg Glu His His Asp Lys Val Arg Gly Trp
        660                 665                 670

Val Gly Phe Ser Val Arg Leu Ala His Arg Ile Thr Ala Gly Ala Asp
    675                 680                 685

Ala Leu Leu Met Pro Ser Arg Phe Glu Pro Cys Gly Leu Asn Gln Leu
690                 695                 700

Tyr Ala Met Ala Tyr Gly Thr Val Pro Val Val His Ala Val Gly Gly
705                 710                 715                 720

Leu Arg Asp Thr Val Pro Pro Phe Asp Pro Phe Asn His Ser Gly Leu
                725                 730                 735

Gly Trp Thr Phe Asp Arg Ala Glu Ala Gln Lys Leu Ile Glu Ala Leu
            740                 745                 750

Gly His Cys Leu Arg Thr Tyr Arg Asp Tyr Lys Glu Ser Trp Arg Gly
        755                 760                 765

Leu Gln Glu Arg Gly Met Ser Gln Asp Phe Ser Trp Glu His Ala Ala
    770                 775                 780

Lys Leu Tyr Glu Asp Val Leu Val Lys Ala Lys Tyr Gln Trp
785                 790                 795

<210> SEQ ID NO 7
<211> LENGTH: 2805
<212> TYPE: DNA
<213> ORGANISM: Triticum aestivum

<400> SEQUENCE: 7
cctgcgcgcg ccatggcggc tctggtcacg tcccagctcg ccacctccgg caccgtcctc      60
agcgtcaccg acagattccg gcgtccaggt tttcagggcc tgaggccccg gaacccggcg     120
gatgcggcgc tcggcatgag gactgtcgga gcgagcgccg ccccaaagca agcaggaaa      180 ccgcaccgat tcgaccggcg gtgcctctcc atggtggtgc gcgccacggg cagcggcggc     240
atgaacctcg tgttcgtcgg cgccgagatg gcgccctgga gcaagactgg cggcctcggc     300
gacgtcctcg ggggcctccc cgccgccatg gccgtaagct gcgccactg ccttcttata      360 aatgtttctt cctgcagcca tgcctgccgt acaacgggt gccgtgtccg tgcaggccaa      420
cggtcaccgg gtcatggtca tctccccgcg ctacgaccag tacaaggacg cctgggacac     480
cagcgtcatc tccgaggtat atatccgcca catgaattat cacaattcac atgctcctgc     540
acatttctgc aagactttac tgactggctg atctcgcag atcaaggtcg ttgacaggta     600
cgagagggtg aggtacttcc actgctacaa gcgcggggtg gaccgcgtgt tcgtcgacca     660
cccgtgcttc ctggagaagg tgaccgatcg ctcgccgtcg atcgatcaag ctagctcctc     720
gtcgtctcaa cccgcatggt gtttgataat ttcagtgagt ctttgcgtct gctggttaca     780
atttccaggt ccggggcaag accaaggaga agatctatgg acccgacgcc ggcaccgact     840
acgaggacaa ccagcagcgc ttcagccttc tctgccaggc agcacttgag gtgcccagga     900
tcctcgacct caacaacaac ccacactttt ctggacccta cggtaagatc aagaacaact     960
agagtgtatc tgaagaactt gatttctact tgagagcact ggatgattat catcttcctt    1020
gtatcttggt gctgccatgc tatgccgtgc cgtgccgcgc cgcgcagggg aagacgtggt    1080
gtttgtgtgc aacgactggc acacgggcct tctggcctgc tacctcaaga gcaactacca    1140
```

```
gtccaatggc atctatagga cggccaaggt tttgcatctt ctgaaacttt atattcgctc    1200
tgcatatcaa ttttgcggtt cattctggca gcctgaattt tacattgcaa ctccatttca    1260
tggctaggtg gcattctgca tccacaacat ctcgtaccag ggccgcttct ccttcgacga    1320
cttcgcgcag ctcaacctgc ctgacaggtt caagtcgtcc ttcgacttca tcgacggcta    1380
cgacaagccg gtggaggggc gcaagatcaa ctggatgaag gccgggatcc tgcaggccga    1440
caaggtgctg actgtgagcc cctactatgc tgagagcta atctctggcg aagccagggg    1500
ctgcgagctc gacaacatca tgcgcctcac tgggatcacc ggcatcgtca cggcatgga    1560 cgtcagcgag tgggacccca tcaaggacaa gttcctcacc gtcaactacg acgtcaccac    1620
cgtgagcacc cacccaccca cacaaagatt tcttccggtg atcgctggtt ctgggtggat    1680
tctgagttct gacaaacgag gcaaagtgac aggcgttgga ggggaaggcg ctgaacaagg    1740
aggcgctgca ggccgaggtg gggctgccgg tggaccggaa ggtgcccctg gtggcgttca    1800
tcggcaggct ggaggagcag aagggccccg acgtgatgat cgccgccatc ccggagatcg    1860
tgaaggagga ggacgtccag atcgttctcc tggtacgatc gaccgacatt gctgacccgt    1920
tcaggaaaat ctcctgatag ctcgccgtgg ggatgggtgg gtgactgact gatcgaatgc    1980
attgcagggc accgggaaga agaagtttga gcggctgctc aagagcgtgg aggagaagtt    2040
cccgaccaag gtgtgggccg tggtcaggtt caacgcgccg ctggctcacc agatgatggc    2100
cggcgccgac gtgctggcgg tcaccagccg cttcgagccc tgcggcctca tccagctcca    2160
gggaatgcgc tacggaacgg taaacgcatc ctccttcagt ccttcttgcc agttcctcac    2220
ctcctttgca tatccatggc catgaccgaa gtttctttca aatttcagc cgtgcgcctg    2280 cgcgtcgaca ggcgggctcg tcgacactat cgtggaaggc aagaccgggt tccacatggg    2340
ccgcctcagc gttgacgtat gctcatcgat cctcttgtat acattcattc atcttgttca    2400
tcatggcagc tcagacagat catgaagtgg tgcacttttc ttgttggtgg ccagtgcaac    2460
gtggtggagc cggccgacgt gaagaaggtg gtcaccaccc tgaagcgcgc cgtcaaggtc    2520
gtcggcacgc cggcgtacca tgagatggtc aagaactgca tgatacagga tctctcctgg    2580
aaggtaagtc gtctctggtt cagtatgcac ttcctggaac aactaagagt gaagggccga    2640
tgtatccatt aatggtggct tgcgcatatg atgcaggggc ctgccaagaa ctgggaggac    2700
gtgcttctgg aactgggggt ggaggggagc gagccggcac tcgtcggcga ggagatcgcg    2760
ccgctcgccc tggagaacgt cgccgctccc tgaagagaga aagaa              2805
```

<210> SEQ ID NO 8
<211> LENGTH: 604
<212> TYPE: PRT
<213> ORGANISM: Triticum aestivum

<400> SEQUENCE: 8

Met Ala Ala Leu Val Thr Ser Gln Leu Ala Thr Ser Gly Thr Val Leu
1               5                   10                  15

Ser Val Thr Asp Arg Phe Arg Arg Pro Gly Phe Gln Gly Leu Arg Pro
            20                  25                  30

Arg Asn Pro Ala Asp Ala Ala Leu Gly Met Arg Thr Val Gly Ala Ser
        35                  40                  45

Ala Ala Pro Lys Gln Ser Arg Lys Pro His Arg Phe Asp Arg Arg Cys
    50                  55                  60

Leu Ser Met Val Val Arg Ala Thr Gly Ser Gly Gly Met Asn Leu Val
65                  70                  75                  80

```
Phe Val Gly Ala Glu Met Ala Pro Trp Ser Lys Thr Gly Leu Gly
                85                  90                  95

Asp Val Leu Gly Gly Leu Pro Ala Ala Met Ala Ala Asn Gly His Arg
            100                 105                 110

Val Met Val Ile Ser Pro Arg Tyr Asp Gln Tyr Lys Asp Ala Trp Asp
            115                 120                 125

Thr Ser Val Ile Ser Glu Ile Lys Val Val Asp Arg Tyr Glu Arg Val
        130                 135                 140

Arg Tyr Phe His Cys Tyr Lys Arg Gly Val Asp Arg Val Phe Val Asp
145                 150                 155                 160

His Pro Cys Phe Leu Glu Lys Val Arg Gly Lys Thr Lys Glu Lys Ile
                165                 170                 175

Tyr Gly Pro Asp Ala Gly Thr Asp Tyr Glu Asp Asn Gln Gln Arg Phe
            180                 185                 190

Ser Leu Leu Cys Gln Ala Ala Leu Glu Val Pro Arg Ile Leu Asp Leu
        195                 200                 205

Asn Asn Asn Pro His Phe Ser Gly Pro Tyr Gly Glu Asp Val Val Phe
210                 215                 220

Val Cys Asn Asp Trp His Thr Gly Leu Leu Ala Cys Tyr Leu Lys Ser
225                 230                 235                 240

Asn Tyr Gln Ser Asn Gly Ile Tyr Arg Thr Ala Lys Val Ala Phe Cys
                245                 250                 255

Ile His Asn Ile Ser Tyr Gln Gly Arg Phe Ser Phe Asp Asp Phe Ala
            260                 265                 270

Gln Leu Asn Leu Pro Asp Arg Phe Lys Ser Ser Phe Asp Phe Ile Asp
        275                 280                 285

Gly Tyr Asp Lys Pro Val Glu Gly Arg Lys Ile Asn Trp Met Lys Ala
            290                 295                 300

Gly Ile Leu Gln Ala Asp Lys Val Leu Thr Val Ser Pro Tyr Tyr Ala
305                 310                 315                 320

Glu Glu Leu Ile Ser Gly Glu Ala Arg Gly Cys Glu Leu Asp Asn Ile
                325                 330                 335

Met Arg Leu Thr Gly Ile Thr Gly Ile Val Asn Gly Met Asp Val Ser
            340                 345                 350

Glu Trp Asp Pro Ile Lys Asp Lys Phe Leu Thr Val Asn Tyr Asp Val
        355                 360                 365

Thr Thr Ala Leu Glu Gly Lys Ala Leu Asn Lys Glu Ala Leu Gln Ala
    370                 375                 380

Glu Val Gly Leu Pro Val Asp Arg Lys Val Pro Leu Val Ala Phe Ile
385                 390                 395                 400

Gly Arg Leu Glu Glu Gln Lys Gly Pro Asp Val Met Ile Ala Ala Ile
                405                 410                 415

Pro Glu Ile Val Lys Glu Glu Asp Val Gln Ile Val Leu Leu Gly Thr
            420                 425                 430

Gly Lys Lys Lys Phe Glu Arg Leu Leu Lys Ser Val Glu Glu Lys Phe
        435                 440                 445

Pro Thr Lys Val Trp Ala Val Val Arg Phe Asn Ala Pro Leu Ala His
    450                 455                 460

Gln Met Met Ala Gly Ala Asp Val Leu Ala Val Thr Ser Arg Phe Glu
465                 470                 475                 480

Pro Cys Gly Leu Ile Gln Leu Gln Gly Met Arg Tyr Gly Thr Pro Cys
                485                 490                 495
```

```
Ala Cys Ala Ser Thr Gly Gly Leu Val Asp Thr Ile Val Glu Gly Lys
                500                 505                 510

Thr Gly Phe His Met Gly Arg Leu Ser Val Asp Cys Asn Val Val Glu
        515                 520                 525

Pro Ala Asp Val Lys Lys Val Val Thr Thr Leu Lys Arg Ala Val Lys
    530                 535                 540

Val Val Gly Thr Pro Ala Tyr His Glu Met Val Lys Asn Cys Met Ile
545                 550                 555                 560

Gln Asp Leu Ser Trp Lys Gly Pro Ala Lys Asn Trp Glu Asp Val Leu
                565                 570                 575

Leu Glu Leu Gly Val Glu Gly Ser Glu Pro Gly Ile Val Gly Glu Glu
            580                 585                 590

Ile Ala Pro Leu Ala Leu Glu Asn Val Ala Ala Pro
            595                 600

<210> SEQ ID NO 9
<211> LENGTH: 2818
<212> TYPE: DNA
<213> ORGANISM: Triticum aestivum

<400> SEQUENCE: 9
cctgcgcgcg cgatggcggc tctggtcacg tcgcagctcg ccacctccgg caccgtcctc      60
ggcatcaccg acaggttccg gcgtgcaggt tttcagggtg tgaggccccg gagcccggca     120
gatgcgccgc tcggcatgag gactaccgga gcgagcgccg ccccgaagca acaaagccgg     180
aaagcgcacc gcgggacccg gcggtgcctc tccatggtgg tgcgcgccac gggcagcgcc     240
ggcatgaacc tcgtgttcgt cggcgccgag atggcgccct ggagcaagac cggcggcctc     300
ggcgacgtcc tcggggggcct ccccccagcc atggccgtaa gctagctagc tagcaccact     360
gtcttctgat aatgtttctt cttgcagcca gccatgcctg ccattacaag tttacaactg     420
atgctgtgtc tgcaggccaa cggtcaccgg gtcatggtca tctccccgcg ctacgaccag     480
tacaaggacg cctgggacac cagcgtcgtc tccgaggtac acatatatcc gccacatgaa     540
ttatcacagt tcacatgctc ctgcacattt ctgcaaggtt ccactcaccg actggatttc     600
acagatcaag gtcgcggacg agtacgagag ggtgaggtac ttccactgct acaagcgcgg     660
ggtggaccgc gtgttcgtcg accacccgtg cttcctggag aaggtgacca atcgtcgtcg     720
tcgatcgatc aatcgatcaa gctatctttt cgtcgtctca acattcatgg tgattgattt     780
gggtgagtct ttgtttctgc tggttgcaat ttccaggtcc ggggcaagac caaggagaag     840
atctacgggc ccgatgccgg cacggactac gaggacaacc agctacgctt cagcctgctc     900
tgccaggcag cgcttgaggc acccaggatc ctcgacctca caacaaccc atacttctcc     960 ggaccctacg gtaagatcaa caacacccag cagctactag agtgtctgaa gaacttgatt    1020
tcttcttgag agcactggat gattatcatc ttccctgtgt cttggtgctg ccacgccatg    1080
ctatgccgcg ccacgccgcg caggggaaga cgtggtgttc gtgtgcaacg actggcacac    1140
gggccttctg gcctgctacc tcaagagcaa ctaccagtcc agtggcatct ataggacggc    1200
caaggttttg catcttctca aactttatat tctctctgca gaattttaca ttgcaacttc    1260
atttcatgtc caggtagcgt tctgcatcca aacatctcg tatcagggcc gcttctcctt    1320
cgacgacttc gcgcagctca acctgcccga caggttcaag tcgtccttcg acttcatcga    1380
cggctacgac aagccggtgg aggggcgcaa gatcaactgg atgaaggccg ggatcctgca    1440
ggccgacaag gtgctcacgg tgagcccta ctacgcggag gagctcatct ccggcgaagc    1500
```

-continued

```
caggggctgc gagctcgaca acatcatgcg cctcacgggc atcaccggca tcgtcaacgg    1560
catggacgtc agcgagtggg accccgccaa ggacaagttc ctcgccgcca actacgacgt    1620
caccaccgtg agcacccgcc cacccacaca cccacacaaa gatttcttcc ggtgattgct    1680
ggttctgggt gggttctgac ggacgaggca aagtgacagg cgttggaggg gaaggcgctg    1740
aacaaggagg cgctgcaggc cgaggtgggg ctgccggtgg accggaaggt gcccctggtg    1800
gccttcatcg gcaggctgga ggagcagaag ggccccgacg tgatgatcgc cgccatcccg    1860
gagatcttga aggaggagga cgtccagatc gttctcctgg tacgtcatcg accccaaccg    1920
caacccgacc gccattgctg aagcttcaat caagcagacc taaggaatga tcggatgcat    1980
tgcagggcac cgggaagaag aagtttgagc ggctgctcaa gagcgtggag gagaagttcc    2040
cgagcaaggt gagggccgtg gtcaggttca acgcgccgct ggctcaccag atgatggccg    2100
gcgccgacgt gctcgccgtc accagccgct tcgagccctg cggcctcatc cagctccagg    2160
ggatgcgcta cggaacggta aacgccgcct cctccttcct gccgattcct tatctccccg    2220
cgtatccatg gccatgaccg aagtttcttt caaatttgca gccgtgcgcg tgcgcgtcca    2280
ccggcgggct cgtcgacacg atcatggagg gcaagaccgg gttccacatg gccgcctca    2340 gcgtcgacgt aggctcgtcg atcccttgtg taaattcttc attttgttca tcctgggagc    2400
tcaggcagat catgaaatgg tttcctttt cctcttggtg gccagtgcaa cgtggtggag    2460
ccggccgacg tgaagaaggt ggtgaccacc ctgaagcgcg ccgtcaaggt cgtcggcacg    2520
ccagcctacc atgagatggt caagaactgc atgatccagg atctctcctg gaaggtaagt    2580
cgtctctggt ctggtttagg atgcatttc cagaacaact aagagttgag actacaatgg    2640
tgctcgtgct cgatgcatcc attaatggtg gcttgcgcat atggtgcagg ggccagccaa    2700
gaactgggag gacgtgcttc tggaactggg ggtcgagggg agcgagccag gggtcatcgg    2760
cgaggagatt gcgccgctcg ccatggagaa cgtcgccgct ccctgaagag aggaaaga    2818
```

<210> SEQ ID NO 10
<211> LENGTH: 605
<212> TYPE: PRT
<213> ORGANISM: Triticum aestivum

<400> SEQUENCE: 10

```
Met Ala Ala Leu Val Thr Ser Gln Leu Ala Thr Ser Gly Thr Val Leu
1               5                   10                  15

Gly Ile Thr Asp Arg Phe Arg Arg Ala Gly Phe Gln Gly Val Arg Pro
            20                  25                  30

Arg Ser Pro Ala Asp Ala Pro Leu Gly Met Arg Thr Thr Gly Ala Ser
        35                  40                  45

Ala Ala Pro Lys Gln Gln Ser Arg Lys Ala His Arg Gly Thr Arg Arg
    50                  55                  60

Cys Leu Ser Met Val Val Arg Ala Thr Gly Ser Ala Gly Met Asn Leu
65                  70                  75                  80

Val Phe Val Gly Ala Glu Met Ala Pro Trp Ser Lys Thr Gly Gly Leu
                85                  90                  95

Gly Asp Val Leu Gly Gly Leu Pro Pro Ala Met Ala Ala Asn Gly His
            100                 105                 110

Arg Val Met Val Ile Ser Pro Arg Tyr Asp Gln Tyr Lys Asp Ala Trp
        115                 120                 125

Asp Thr Ser Val Val Ser Glu Ile Lys Val Ala Asp Glu Tyr Glu Arg
    130                 135                 140
```

```
Val Arg Tyr Phe His Cys Tyr Lys Arg Gly Val Asp Arg Val Phe Val
145                 150                 155                 160

Asp His Pro Cys Phe Leu Glu Lys Val Arg Gly Lys Thr Lys Glu Lys
                165                 170                 175

Ile Tyr Gly Pro Asp Ala Gly Thr Asp Tyr Glu Asp Asn Gln Leu Arg
            180                 185                 190

Phe Ser Leu Leu Cys Gln Ala Ala Leu Glu Ala Pro Arg Ile Leu Asp
        195                 200                 205

Leu Asn Asn Pro Tyr Phe Ser Gly Pro Tyr Gly Glu Asp Val Val
    210                 215                 220

Phe Val Cys Asn Asp Trp His Thr Gly Leu Leu Ala Cys Tyr Leu Lys
225                 230                 235                 240

Ser Asn Tyr Gln Ser Ser Gly Ile Tyr Arg Thr Ala Lys Val Ala Phe
                245                 250                 255

Cys Ile His Asn Ile Ser Tyr Gln Gly Arg Phe Ser Phe Asp Asp Phe
            260                 265                 270

Ala Gln Leu Asn Leu Pro Asp Arg Phe Lys Ser Ser Phe Asp Phe Ile
        275                 280                 285

Asp Gly Tyr Asp Lys Pro Val Glu Gly Arg Lys Ile Asn Trp Met Lys
    290                 295                 300

Ala Gly Ile Leu Gln Ala Asp Lys Val Leu Thr Val Ser Pro Tyr Tyr
305                 310                 315                 320

Ala Glu Glu Leu Ile Ser Gly Glu Ala Arg Gly Cys Glu Leu Asp Asn
                325                 330                 335

Ile Met Arg Leu Thr Gly Ile Thr Gly Ile Val Asn Gly Met Asp Val
            340                 345                 350

Ser Glu Trp Asp Pro Ala Lys Asp Lys Phe Leu Ala Ala Asn Tyr Asp
        355                 360                 365

Val Thr Thr Ala Leu Glu Gly Lys Ala Leu Asn Lys Glu Ala Leu Gln
    370                 375                 380

Ala Glu Val Gly Leu Pro Val Asp Arg Lys Val Pro Leu Val Ala Phe
385                 390                 395                 400

Ile Gly Arg Leu Glu Glu Gln Lys Gly Pro Asp Val Met Ile Ala Ala
                405                 410                 415

Ile Pro Glu Ile Leu Lys Glu Glu Asp Val Gln Ile Val Leu Leu Gly
            420                 425                 430

Thr Gly Lys Lys Lys Phe Glu Arg Leu Leu Lys Ser Val Glu Glu Lys
        435                 440                 445

Phe Pro Ser Lys Val Arg Ala Val Arg Phe Asn Ala Pro Leu Ala
    450                 455                 460

His Gln Met Met Ala Gly Ala Asp Val Leu Ala Val Thr Ser Arg Phe
465                 470                 475                 480

Glu Pro Cys Gly Leu Ile Gln Leu Gln Gly Met Arg Tyr Gly Thr Pro
                485                 490                 495

Cys Ala Cys Ala Ser Thr Gly Gly Leu Val Asp Thr Ile Met Glu Gly
            500                 505                 510

Lys Thr Gly Phe His Met Gly Arg Leu Ser Val Asp Cys Asn Val Val
        515                 520                 525

Glu Pro Ala Asp Val Lys Lys Val Thr Thr Leu Lys Arg Ala Val
    530                 535                 540

Lys Val Val Gly Thr Pro Ala Tyr His Glu Met Val Lys Asn Cys Met
545                 550                 555                 560

Ile Gln Asp Leu Ser Trp Lys Gly Pro Ala Lys Asn Trp Glu Asp Val
```

565                 570                 575
Leu Leu Glu Leu Gly Val Glu Gly Ser Glu Pro Gly Val Ile Gly Glu
        580                 585                 590

Glu Ile Ala Pro Leu Ala Met Glu Asn Val Ala Ala Pro
        595                 600             605

<210> SEQ ID NO 11
<211> LENGTH: 2575
<212> TYPE: DNA
<213> ORGANISM: Triticum aestivum

<400> SEQUENCE: 11
cggcacgagc ggcacgagat cacctcggcc tcggccaccg gcaaaccccc cgatccgctt      60
ttgcaggcag cgcactaaaa ccccggggag cgcgccccgc ggcagcagca gcaccgcagt     120
gggagagaga ggcttcgccc cggcccgcac cgagcggggc gatccaccgt ccgtgcgtcc     180
gcacctcctc cgcctcctcc cctgtcccgc gcgcccacac ccatggcggc gacgggcgtc     240
ggcgccgggt gcctcgcccc cagcgtccgc ctgcgcgccg atccggcgac ggcggcccgg     300
gcgtccgcct gcgtcgtccg cgcgcggctc cggcgcttgg cgcggggccg ctacgtcgcc     360
gagctcagca gggagggccc cgcggcgcgc cccgcgcagc agcagcaact ggccccgccg     420
ctcgtgccag gcttcctcgc gccgccgccg cccgcgcccg ccagtcgcc ggccccgacg      480 cagccgcccc tgccggacgc cggcgtgggg gaactcgcgc ccgacctcct gctcgaaggg     540
attgctgagg attccatcga cagcataatt gtggctgcaa gtgagcagga ttctgagatc     600
atggatgcga atgagcaacc tcaagctaaa gttacacgta gcatcgtgtt tgtgactggt     660
gaagctgctc cttatgcaaa gtcagggggg ctgggagatg tttgtggttc gttaccaatt     720
gctcttgctg ctcgtggtca ccgtgtgatg gttgtaatgc caagatactt gaatgggtcc     780
tctgataaaa actatgcaaa ggcattatac actgggaagc acattaagat tccatgcttt     840 ggggggatcac atgaagtgac ctttttttcat gagtatagag acaacgtcga ttgggtgttt     900
gtcgatcatc cgtcatatca tagaccagga agtttatatg gagataattt tggtgctttt     960
ggtgataatc agttcagata cactccctt tgctatgctg catgcgaggc cccactaatc    1020
cttgaattgg gaggatatat ttatggacag aattgcatgt ttgttgtgaa cgattggcat    1080
gccagccttg tgccagtcct tcttgctgca aaatatagac catacggtgt ttacagagat    1140
tcccgcagca cccttgttat acataattta gcacatcagg gtgtggagcc tgcaagtaca    1200
tatcctgatc tgggattgcc acctgaatgg tatggagctt tagaatgggt atttccagaa    1260
tgggcaagga ggcatgccct tgacaagggt gaggcagtta acttttttgaa aggagcagtc    1320 gtgacagcag atcgaattgt gaccgtcagt caggggttatt catgggaggt cacaactgct    1380
gaaggtggac agggcctcaa tgagctctta agctcccgaa aaagtgtatt gaatggaatt    1440
gtaaatggaa ttgacattaa tgattggaac cccaccacag acaagtgtct ccctcatcat    1500
tattctgtcg atgacctctc tggaaaggcc aaatgtaaag ctgaattgca gaaggagctg    1560
ggtttacctg taagggagga tgttcctctg attggcttta ttggaagact ggattaccag    1620
aaaggcattg atctcattaa aatgccattc cagagctca tgagggagga cgtgcagttt    1680
gtcatgcttg gatctgggga tccaattttt gaaggctgga tgagatctac cgagtcgagt    1740
tacaaggata aattccgtgg atgggttgga tttagtgttc cagtttccca cagaataact    1800
gcaggttgcg atatattgtt aatgccatcc aggtttgaac cttgtggtct taatcagcta    1860
tatgctatgc aatatggtac agttcctgta gttcatggaa ctgggggcct ccgagacaca    1920

-continued

```
gtcgagacct tcaacccttt tggtgcaaaa ggagaggagg gtacagggtg ggcgttctca    1980
ccgctaaccg tggacaagat gttgtgggca ttgcgaaccg cgatgtcgac attcagggag    2040
cacaagccgt cctgggaggg gctcatgaag cgaggcatga cgaaagacca tacgtgggac    2100
catgccgccg agcagtacga gcagatcttc gaatgggcct tcgtggacca accctacgtc    2160
atgtagacgg ggactgggga ggtcgaagcg cgggtctcct tgagctctga agacatgttc    2220
ctcatccttc cgcggcccgg aaggataccc ctgtacattg cgttgtcctg ctacagtaga    2280
gtcgcaatgc gcctgcttgc ttggtccgcc ggttcgagag tagatgacgg ctgtgctgct    2340
gcggcggtga cagcttcggg tggatgacag ttacagtttt ggggaataag gaagggatgt    2400
gctgcaggat ggttaacagc aaagcaccac tcagatggca gcctctctgt ccgtgttaca    2460
gctgaaatca gaaaccaact ggtgactctt tagccttagc gattgtgaag tttgttgcat    2520
tctgtgtatg ttgtcttgtc cttagctgac aaatatttga cctgttggat aattc         2575
```

<210> SEQ ID NO 12
<211> LENGTH: 647
<212> TYPE: PRT
<213> ORGANISM: Triticum aestivum

<400> SEQUENCE: 12

```
Met Ala Ala Thr Gly Val Gly Ala Gly Cys Leu Ala Pro Ser Val Arg
1               5                   10                  15

Leu Arg Ala Asp Pro Ala Thr Ala Ala Arg Ala Ser Ala Cys Val Val
                20                  25                  30

Arg Ala Arg Leu Arg Arg Leu Ala Arg Gly Arg Tyr Val Ala Glu Leu
            35                  40                  45

Ser Arg Glu Gly Pro Ala Ala Arg Pro Ala Gln Gln Gln Leu Ala
        50                  55                  60

Pro Pro Leu Val Pro Gly Phe Leu Ala Pro Pro Pro Ala Pro Ala
65                  70                  75                  80

Gln Ser Pro Ala Pro Thr Gln Pro Pro Leu Pro Asp Ala Gly Val Gly
                85                  90                  95

Glu Leu Ala Pro Asp Leu Leu Leu Glu Gly Ile Ala Glu Asp Ser Ile
            100                 105                 110

Asp Ser Ile Ile Val Ala Ala Ser Glu Gln Asp Ser Glu Ile Met Asp
        115                 120                 125

Ala Asn Glu Gln Pro Gln Ala Lys Val Thr Arg Ser Ile Val Phe Val
    130                 135                 140

Thr Gly Glu Ala Ala Pro Tyr Ala Lys Ser Gly Gly Leu Gly Asp Val
145                 150                 155                 160

Cys Gly Ser Leu Pro Ile Ala Leu Ala Ala Arg Gly His Arg Val Met
                165                 170                 175

Val Val Met Pro Arg Tyr Leu Asn Gly Ser Ser Asp Lys Asn Tyr Ala
            180                 185                 190

Lys Ala Leu Tyr Thr Gly Lys His Ile Lys Ile Pro Cys Phe Gly Gly
        195                 200                 205

Ser His Glu Val Thr Phe Phe His Glu Tyr Arg Asp Asn Val Asp Trp
    210                 215                 220

Val Phe Val Asp His Pro Ser Tyr His Arg Pro Gly Ser Leu Tyr Gly
225                 230                 235                 240

Asp Asn Phe Gly Ala Phe Gly Asp Asn Gln Phe Arg Tyr Thr Leu Leu
                245                 250                 255
```

```
Cys Tyr Ala Ala Cys Glu Ala Pro Leu Ile Leu Glu Leu Gly Gly Tyr
            260                 265                 270

Ile Tyr Gly Gln Asn Cys Met Phe Val Val Asn Asp Trp His Ala Ser
        275                 280                 285

Leu Val Pro Val Leu Leu Ala Ala Lys Tyr Arg Pro Tyr Gly Val Tyr
    290                 295                 300

Arg Asp Ser Arg Ser Thr Leu Val Ile His Asn Leu Ala His Gln Gly
305                 310                 315                 320

Val Glu Pro Ala Ser Thr Tyr Pro Asp Leu Gly Leu Pro Pro Glu Trp
                325                 330                 335

Tyr Gly Ala Leu Glu Trp Val Phe Pro Glu Trp Ala Arg Arg His Ala
            340                 345                 350

Leu Asp Lys Gly Glu Ala Val Asn Phe Leu Lys Gly Ala Val Val Thr
        355                 360                 365

Ala Asp Arg Ile Val Thr Val Ser Gln Gly Tyr Ser Trp Glu Val Thr
    370                 375                 380

Thr Ala Glu Gly Gly Gln Gly Leu Asn Glu Leu Leu Ser Ser Arg Lys
385                 390                 395                 400

Ser Val Leu Asn Gly Ile Val Asn Gly Ile Asp Ile Asn Asp Trp Asn
                405                 410                 415

Pro Thr Thr Asp Lys Cys Leu Pro His His Tyr Ser Val Asp Asp Leu
            420                 425                 430

Ser Gly Lys Ala Lys Cys Lys Ala Glu Leu Gln Lys Glu Leu Gly Leu
        435                 440                 445

Pro Val Arg Glu Asp Val Pro Leu Ile Gly Phe Ile Gly Arg Leu Asp
    450                 455                 460

Tyr Gln Lys Gly Ile Asp Leu Ile Lys Met Ala Ile Pro Glu Leu Met
465                 470                 475                 480

Arg Glu Asp Val Gln Phe Val Met Leu Gly Ser Gly Asp Pro Ile Phe
                485                 490                 495

Glu Gly Trp Met Arg Ser Thr Glu Ser Ser Tyr Lys Asp Lys Phe Arg
            500                 505                 510

Gly Trp Val Gly Phe Ser Val Pro Val Ser His Arg Ile Thr Ala Gly
        515                 520                 525

Cys Asp Ile Leu Leu Met Pro Ser Arg Phe Glu Pro Cys Gly Leu Asn
    530                 535                 540

Gln Leu Tyr Ala Met Gln Tyr Gly Thr Val Pro Val Val His Gly Thr
545                 550                 555                 560

Gly Gly Leu Arg Asp Thr Val Glu Thr Phe Asn Pro Phe Gly Ala Lys
                565                 570                 575

Gly Glu Glu Gly Thr Gly Trp Ala Phe Ser Pro Leu Thr Val Asp Lys
            580                 585                 590

Met Leu Trp Ala Leu Arg Thr Ala Met Ser Thr Phe Arg Glu His Lys
        595                 600                 605

Pro Ser Trp Glu Gly Leu Met Lys Arg Gly Met Thr Lys Asp His Thr
    610                 615                 620

Trp Asp His Ala Ala Glu Gln Tyr Glu Gln Ile Phe Glu Trp Ala Phe
625                 630                 635                 640

Val Asp Gln Pro Tyr Val Met
                645

<210> SEQ ID NO 13
<211> LENGTH: 2421
<212> TYPE: DNA
```

<213> ORGANISM: Triticum aestivum

<400> SEQUENCE: 13

```
cggcacgagg gcagcagcag caccgcagtg ggagagagag gcttcgcccc ggcccgcacc      60
gagcgcgcgg ggcgatccac cgtccgcccg tccgcacctc ctcctctgct ccgcgggccc     120
gcacccatgg cggcgacggg cgtcggcgcc gggtgcctcg cccccagcgt ccgcctgcgc     180
gccgatccgg cgacggcggc ccgagcgtcc gcctgcgtcg tccgcgcgcg gctccggcgc     240
gtcgcgcggg gccgctacgt cgccgagctc agcagggagg ccccgcggc gcgccccgcg      300
cagcagcagc agctggcccc gccgctcgtg ccaggcttcc tcgcgccgcc gccgcccgcg     360
cccgcccagt cgccggcccc gacgcagccg cccctgccgg acgccggcgt gggggaactc     420
gcgcccgacc tcctgctcga agggattgct gaggattcca ttgacagcat aattgtggct     480
gcaagtgagc aggattctga gatcatggat gccaaggatc aacctcaagc taaagttact     540
cgcagcatcg tgtttgtgac tggggaagct gctccttatg caaagtcagg ggggttggga     600
gatgtttgtg gttcgttacc aattgctctt gctgctcgtg gtcaccgagt gatggttgta     660
atgccaagat acttaaatgg gtcctctgat aaaaactatg caaaggcatt atacactgcg     720
aagcacatta agattccatg ctttggggga tcacatgaag tgacctttt tcatgagtat      780
agagacaacg tcgattgggt gtttgtcgat catccgtcat atcacagacc aggaagttta     840
tatggagata ttttggtgc ttttggtgat aatcagttca gatacacact cctttgctat      900
gctgcatgcg aggccccact aatccttgaa ttgggaggat atatttatgg acagaattgc     960
atgtttgttg tgaacgattg gcatgccagc cttgtgccag tccttcttgc tgcaaaatat    1020
agaccatacg gtgtttacag agattcccgc agcacccttg ttatacataa tttagcacat    1080
cagggtgtgg agcctgcaag tacatatcct gatctgggat tgcctcctga atggtatgga    1140
gctttagaat gggtatttcc agaatgggca aggaggcatg cccttgacaa gggtgaggca    1200
gttaactttt tgaaaggagc agttgtgaca gcagatcgga ttgtgaccgt cagtcagggt    1260
tattcatggg aggtcacaac tgctgaaggt ggacagggcc tcaatgagct cttaagctcc    1320
cgaaaaagtg tattgaatgg aattgtaaat ggaattgaca ttaatgattg gaaccccacc    1380
acagacaagt gtctccctca tcattattct gtcgatgacc tctctggaaa ggccaaatgt    1440
aaagctgaat tgcagaagga gttgggttta cctgtaaggg aggatgttcc tctgattggc    1500
tttattggaa gactggatta ccagaaaggc attgatctca ttaaaatggc cattccagag    1560
ctcatgaggg aggacgtgca atttgtcatg cttggatctg gggatccaat tttttgaaggc    1620
tggatgagat ctaccgagtc gagttacaag gataaattcc gtggatgggt tggatttagt    1680
gttccagttt cccacagaat aactgcaggt tgcgatatat tgttaatgcc atcgagattt    1740
gaaccttgcg gtcttaatca gctatatgct atgcaatatg gtacagttcc tgtagttcat    1800
ggaactgggg gcctccgaga cacagtcgag accttcaacc cttttggtgc aaaaggagag    1860
gagggtacag ggtgggcgtt ctcaccgcta accgtggaca gatgttgtg ggcattgcga      1920
accgcgatgt cgacattcag ggagcacaag ccgtcctggg aggggctcat gaagcgaggc    1980
atgacgaaag accatacgtg ggaccatgcc gccgagcagt acgagcagat cttcgagtgg    2040
gccttcgtgg accaacccta cgtcatgtag acggggactg gggaggtcca agtgcgagtc    2100
tccttgagct ctgaagacat cctcttcatc cttccgcggc ccggaaggat acccctgtac    2160
attgcgttgt cctgctacag tagagtcgca atgcgcctgc ttgctttggt tcgccggttc    2220
gagaacatat gacggctgtg ctgctgcggc ggtgacagct tcgggtggac gacagttaca    2280
```

-continued

```
gtttgggga ataaggaagg gatgtgctgc aggatggtta acagcaaagc accactcaga    2340
tggcagcctc tctgtccgtg ttacagctga atcagaaac caactggtga ctctttagcc    2400
ttagtgattg tgaagtttgt t                                              2421
```

<210> SEQ ID NO 14
<211> LENGTH: 647
<212> TYPE: PRT
<213> ORGANISM: Triticum aestivum

<400> SEQUENCE: 14

```
Met Ala Ala Thr Gly Val Gly Ala Gly Cys Leu Ala Pro Ser Val Arg
1               5                   10                  15

Leu Arg Ala Asp Pro Ala Thr Ala Ala Arg Ala Ser Ala Cys Val Val
            20                  25                  30

Arg Ala Arg Leu Arg Arg Val Ala Arg Gly Arg Tyr Val Ala Glu Leu
        35                  40                  45

Ser Arg Glu Gly Pro Ala Ala Arg Pro Ala Gln Gln Gln Leu Ala
    50                  55                  60

Pro Pro Leu Val Pro Gly Phe Leu Ala Pro Pro Pro Ala Pro Ala
65                  70                  75                  80

Gln Ser Pro Ala Pro Thr Gln Pro Pro Leu Pro Asp Ala Gly Val Gly
                85                  90                  95

Glu Leu Ala Pro Asp Leu Leu Leu Glu Gly Ile Ala Glu Asp Ser Ile
            100                 105                 110

Asp Ser Ile Ile Val Ala Ala Ser Glu Gln Asp Ser Glu Ile Met Asp
        115                 120                 125

Ala Lys Asp Gln Pro Gln Ala Lys Val Thr Arg Ser Ile Val Phe Val
    130                 135                 140

Thr Gly Glu Ala Ala Pro Tyr Ala Lys Ser Gly Gly Leu Gly Asp Val
145                 150                 155                 160

Cys Gly Ser Leu Pro Ile Ala Leu Ala Ala Arg Gly His Arg Val Met
                165                 170                 175

Val Val Met Pro Arg Tyr Leu Asn Gly Ser Ser Asp Lys Asn Tyr Ala
            180                 185                 190

Lys Ala Leu Tyr Thr Ala Lys His Ile Lys Ile Pro Cys Phe Gly Gly
        195                 200                 205

Ser His Glu Val Thr Phe Phe His Glu Tyr Arg Asp Asn Val Asp Trp
    210                 215                 220

Val Phe Val Asp His Pro Ser Tyr His Arg Pro Gly Ser Leu Tyr Gly
225                 230                 235                 240

Asp Asn Phe Gly Ala Phe Gly Asp Asn Gln Phe Arg Tyr Thr Leu Leu
                245                 250                 255

Cys Tyr Ala Ala Cys Glu Ala Pro Leu Ile Leu Glu Leu Gly Gly Tyr
            260                 265                 270

Ile Tyr Gly Gln Asn Cys Met Phe Val Val Asn Asp Trp His Ala Ser
        275                 280                 285

Leu Val Pro Val Leu Leu Ala Ala Lys Tyr Arg Pro Tyr Gly Val Tyr
    290                 295                 300

Arg Asp Ser Arg Ser Thr Leu Val Ile His Asn Leu Ala His Gln Gly
305                 310                 315                 320

Val Glu Pro Ala Ser Thr Tyr Pro Asp Leu Gly Leu Pro Pro Glu Trp
                325                 330                 335

Tyr Gly Ala Leu Glu Trp Val Phe Pro Glu Trp Ala Arg Arg His Ala
```

```
              340             345             350
Leu Asp Lys Gly Glu Ala Val Asn Phe Leu Lys Gly Ala Val Val Thr
            355                 360                 365

Ala Asp Arg Ile Val Thr Val Ser Gln Gly Tyr Ser Trp Glu Val Thr
        370                 375                 380

Thr Ala Glu Gly Gly Gln Gly Leu Asn Glu Leu Leu Ser Ser Arg Lys
385                 390                 395                 400

Ser Val Leu Asn Gly Ile Val Asn Gly Ile Asp Ile Asn Asp Trp Asn
                405                 410                 415

Pro Thr Thr Asp Lys Cys Leu Pro His His Tyr Ser Val Asp Asp Leu
            420                 425                 430

Ser Gly Lys Ala Lys Cys Lys Ala Glu Leu Gln Lys Glu Leu Gly Leu
        435                 440                 445

Pro Val Arg Glu Asp Val Pro Leu Ile Gly Phe Ile Gly Arg Leu Asp
    450                 455                 460

Tyr Gln Lys Gly Ile Asp Leu Ile Lys Met Ala Ile Pro Glu Leu Met
465                 470                 475                 480

Arg Glu Asp Val Gln Phe Val Met Leu Gly Ser Gly Asp Pro Ile Phe
                485                 490                 495

Glu Gly Trp Met Arg Ser Thr Glu Ser Ser Tyr Lys Asp Lys Phe Arg
            500                 505                 510

Gly Trp Val Gly Phe Ser Val Pro Val Ser His Arg Ile Thr Ala Gly
        515                 520                 525

Cys Asp Ile Leu Leu Met Pro Ser Arg Phe Glu Pro Cys Gly Leu Asn
    530                 535                 540

Gln Leu Tyr Ala Met Gln Tyr Gly Thr Val Pro Val Val His Gly Thr
545                 550                 555                 560

Gly Gly Leu Arg Asp Thr Val Glu Thr Phe Asn Pro Phe Gly Ala Lys
                565                 570                 575

Gly Glu Glu Gly Thr Gly Trp Ala Phe Ser Pro Leu Thr Val Asp Lys
            580                 585                 590

Met Leu Trp Ala Leu Arg Thr Ala Met Ser Thr Phe Arg Glu His Lys
        595                 600                 605

Pro Ser Trp Glu Gly Leu Met Lys Arg Gly Met Thr Lys Asp His Thr
    610                 615                 620

Trp Asp His Ala Ala Glu Gln Tyr Glu Gln Ile Phe Glu Trp Ala Phe
625                 630                 635                 640

Val Asp Gln Pro Tyr Val Met
                645

<210> SEQ ID NO 15
<211> LENGTH: 2797
<212> TYPE: DNA
<213> ORGANISM: Triticum aestivum

<400> SEQUENCE: 15
ccgccgccat cgacgaagat gctctgcctc accgcctcct cctcgccctc gccctcgccc      60
tctctcccgc cgcgcccctc ccgtcccgct gctgaccggc ccggaccggg gatctcgggc     120
ggcggcaatg tgcggctgag cgcggtgccc gcgccgtctt cgcttcgctg gtcgtggccg     180
cggaaggcca agagcaagtt ctctgttccc gtgtctgcgc aagagaata caccatggca     240 acagctgaag atggcttcgg cgaccttccg atatacgatc tggatcccaa gttcgccggc     300
ttcaaggacc acttcagtta caggatgaaa aagtatcttg aacagaaaca ttcgatcgag     360
```

```
aaatacgagg ggggccttga agagttctct aaaggctact tgaagtttgg gatcaacaca    420
gaaaatgacg caactgtgta ccgggaatgg gcccctgcag caaaggatgc acaacttatt    480
ggtgacttca acaactggaa tggctctggg cacaggatga caaaggataa ttttggtgtt    540
tggtcaatca ggatttccca tgtcaatggg aaacctgcca tccccataa ttccaaggtt     600
aaatttcgat ttcaccgtgg agatggacta tgggtcgatc gggttcctgc atggattcgt    660
tatgcaactt tgatgcctc taaatttgga gctccatatg acggtgttca ctgggatcca     720
ccaactggtg aaaggtatgt gtttaagcat cctcggcctc gaaagcctga cgctccacgt    780
atttacgagg ctcatgtggg gatgagtggt gaaaagcctg aagtaagcac atacagagaa    840
tttgcagaca atgtgttacc gcgcataaag gcaaacaact acaacacagt tcagctgatg    900
gcaatcatgg aacattcata ttatgcttct tttggatacc atgtgacgaa tttcttcgca    960
gttagcagca gatcaggaac accagaggac ctcaaatatc ttgttgacaa ggcacatagc   1020
ttaggggttgc gtgttctgat ggatgttgtc catagccatg cgagcagtaa tatgacagat   1080
ggtctaaatg gctatgatgt tggacaaaac acacaggagt cctatttcca tacaggagaa   1140
agggggttatc ataaactgtg ggatagtcgc ctgttcaact atgccaattg ggaggtctta   1200
cggtatcttc tttctaatct gagatattgg atggacgaat tcatgtttga cggcttccga   1260
tttgatggag taacatccat gctatataat caccatggta tcaatatgtc attcgctgga   1320
aattacaagg aatattttgg tttggatacc gatgtagatg cagttgttta cataatgctt   1380
gcgaaccatt taatgcacaa aatcttgcca gaagcaactg ttgttgcaga agatgtttca   1440
ggcatgccag tgctttgtcg gtcagttgat gaaggtggag tagggtttga ctatcgcctt   1500
gctatggcta ttcctgatag atggattgac tacttgaaga acaaagatga ccttgaatgg   1560
tcaatgagtg caatagcaca tactctgacc aacaggagat atacgaaaaa gtgcattgca   1620
tatgctgaga gccacgatca gtctattgtt ggcgacaaga ctatggcatt tctcttgatg   1680
gacaaggaaa tgtatactgg catgtcagac ttgcagcctg cttcacctac aattgatcgt   1740
ggaattgcac ttcaaaagat gattcacttc atcaccatgg cccttggagg tgatggctac   1800
ttgaatttta tgggtaatga gtttggccac ccagaatgga ttgactttcc aagagaaggc   1860
aacaactgga gttatgataa atgcagacgc cagtggagcc tctcagacat tgatcaccta   1920
cgatacaagt acatgaacgc atttgatcaa gcaatgaatg cgctcgacga caagttttcc   1980
ttcctatcgt catcaaagca gattgtcagc gacatgaatg aggaaaagaa gattattgta   2040
tttgaacgtg gagatctggt cttcgtcttc aactttcatc ccagtaaaac ttatgatggt   2100
tacaaagtcg gatgtgattt gcctgggaag tacaaggtag ctctggactc cgatgctctg   2160
atgtttggtg gacatggaag agtggcccat gacaacgatc acttcacgtc acctgaagga   2220
gtaccaggag tacctgaaac aaacttcaac aaccgcccta ttcattcaa agtcctgtct    2280
ccacccccgca cttgtgtggc ttactatcgc gtcgaggaaa aagcggaaaa gcctaaggat   2340
gaaggagctg cttcttgggg caaagctgct cctgggtaca tcgatgttga agccactcgt   2400
gtcaaagacg cagcagatgg tgaggcgact tctggttcca aaaaggcgtc tacaggaggt   2460
gactccagca agaagggaat taactttgtc ttcgggtcac ctgacaaaga taacaaataa   2520
gcaccatatc aacgcttgat cagaaccgtg taccgacgtc cttgtaatat tcctgctatt   2580
gctagtagta gcaatactgt caaactgtgc agacttgaga ttctggcttg gactttgctg   2640
aggttaccta ctatatagaa agataaataa gaggtgatgg tgcgggtcga gtccggctat   2700
atgtgccaaa tatgcgccat cccgagtcct ctgtcataaa ggaagtttcg ggctttcagc   2760
```
ccagaataaa aacagttgtc tgtttgcaaa aaaaaaa 2797

<210> SEQ ID NO 16
<211> LENGTH: 833
<212> TYPE: PRT
<213> ORGANISM: Triticum aestivum

<400> SEQUENCE: 16

Met Leu Cys Leu Thr Ala Ser Ser Pro Ser Pro Ser Pro Ser Leu
1               5                   10                  15

Pro Pro Arg Pro Ser Arg Pro Ala Ala Asp Arg Pro Gly Pro Gly Ile
            20                  25                  30

Ser Gly Gly Gly Asn Val Arg Leu Ser Ala Val Pro Ala Pro Ser Ser
        35                  40                  45

Leu Arg Trp Ser Trp Pro Arg Lys Ala Lys Ser Lys Phe Ser Val Pro
50                  55                  60

Val Ser Ala Pro Arg Glu Tyr Thr Met Ala Thr Ala Glu Asp Gly Phe
65                  70                  75                  80

Gly Asp Leu Pro Ile Tyr Asp Leu Asp Pro Lys Phe Ala Gly Phe Lys
                85                  90                  95

Asp His Phe Ser Tyr Arg Met Lys Lys Tyr Leu Glu Gln Lys His Ser
            100                 105                 110

Ile Glu Lys Tyr Glu Gly Gly Leu Glu Glu Phe Ser Lys Gly Tyr Leu
        115                 120                 125

Lys Phe Gly Ile Asn Thr Glu Asn Asp Ala Thr Val Tyr Arg Glu Trp
130                 135                 140

Ala Pro Ala Ala Lys Asp Ala Gln Leu Ile Gly Asp Phe Asn Asn Trp
145                 150                 155                 160

Asn Gly Ser Gly His Arg Met Thr Lys Asp Asn Phe Gly Val Trp Ser
                165                 170                 175

Ile Arg Ile Ser His Val Asn Gly Lys Pro Ala Ile Pro His Asn Ser
            180                 185                 190

Lys Val Lys Phe Arg Phe His Arg Gly Asp Gly Leu Trp Val Asp Arg
        195                 200                 205

Val Pro Ala Trp Ile Arg Tyr Ala Thr Phe Asp Ala Ser Lys Phe Gly
210                 215                 220

Ala Pro Tyr Asp Gly Val His Trp Asp Pro Pro Thr Gly Glu Arg Tyr
225                 230                 235                 240

Val Phe Lys His Pro Arg Pro Arg Lys Pro Asp Ala Pro Arg Ile Tyr
                245                 250                 255

Glu Ala His Val Gly Met Ser Gly Glu Lys Pro Glu Val Ser Thr Tyr
            260                 265                 270

Arg Glu Phe Ala Asp Asn Val Leu Pro Arg Ile Lys Ala Asn Asn Tyr
        275                 280                 285

Asn Thr Val Gln Leu Met Ala Ile Met Glu His Ser Tyr Tyr Ala Ser
290                 295                 300

Phe Gly Tyr His Val Thr Asn Phe Phe Ala Val Ser Ser Arg Ser Gly
305                 310                 315                 320

Thr Pro Glu Asp Leu Lys Tyr Leu Val Asp Lys Ala His Ser Leu Gly
                325                 330                 335

Leu Arg Val Leu Met Asp Val Val His Ser His Ala Ser Ser Asn Met
            340                 345                 350

Thr Asp Gly Leu Asn Gly Tyr Asp Val Gly Gln Asn Thr Gln Glu Ser
        355                 360                 365

```
Tyr Phe His Thr Gly Glu Arg Gly Tyr His Lys Leu Trp Asp Ser Arg
    370                 375                 380

Leu Phe Asn Tyr Ala Asn Trp Glu Val Leu Arg Tyr Leu Leu Ser Asn
385                 390                 395                 400

Leu Arg Tyr Trp Met Asp Glu Phe Met Phe Asp Gly Phe Arg Phe Asp
                405                 410                 415

Gly Val Thr Ser Met Leu Tyr Asn His His Gly Ile Asn Met Ser Phe
            420                 425                 430

Ala Gly Asn Tyr Lys Glu Tyr Phe Gly Leu Asp Thr Asp Val Asp Ala
        435                 440                 445

Val Val Tyr Ile Met Leu Ala Asn His Leu Met His Lys Ile Leu Pro
    450                 455                 460

Glu Ala Thr Val Val Ala Glu Asp Val Ser Gly Met Pro Val Leu Cys
465                 470                 475                 480

Arg Ser Val Asp Glu Gly Val Gly Phe Asp Tyr Arg Leu Ala Met
                485                 490                 495

Ala Ile Pro Asp Arg Trp Ile Asp Tyr Leu Lys Asn Lys Asp Asp Leu
                500                 505                 510

Glu Trp Ser Met Ser Ala Ile Ala His Thr Leu Thr Asn Arg Arg Tyr
            515                 520                 525

Thr Glu Lys Cys Ile Ala Tyr Ala Glu Ser His Asp Gln Ser Ile Val
    530                 535                 540

Gly Asp Lys Thr Met Ala Phe Leu Leu Met Asp Lys Glu Met Tyr Thr
545                 550                 555                 560

Gly Met Ser Asp Leu Gln Pro Ala Ser Pro Thr Ile Asp Arg Gly Ile
                565                 570                 575

Ala Leu Gln Lys Met Ile His Phe Ile Thr Met Ala Leu Gly Gly Asp
            580                 585                 590

Gly Tyr Leu Asn Phe Met Gly Asn Glu Phe Gly His Pro Glu Trp Ile
        595                 600                 605

Asp Phe Pro Arg Glu Gly Asn Asn Trp Ser Tyr Asp Lys Cys Arg Arg
    610                 615                 620

Gln Trp Ser Leu Ser Asp Ile Asp His Leu Arg Tyr Lys Tyr Met Asn
625                 630                 635                 640

Ala Phe Asp Gln Ala Met Asn Ala Leu Asp Asp Lys Phe Ser Phe Leu
                645                 650                 655

Ser Ser Ser Lys Gln Ile Val Ser Asp Met Asn Glu Glu Lys Lys Ile
            660                 665                 670

Ile Val Phe Glu Arg Gly Asp Leu Val Phe Val Phe Asn Phe His Pro
        675                 680                 685

Ser Lys Thr Tyr Asp Gly Tyr Lys Val Gly Cys Asp Leu Pro Gly Lys
    690                 695                 700

Tyr Lys Val Ala Leu Asp Ser Asp Ala Leu Met Phe Gly Gly His Gly
705                 710                 715                 720

Arg Val Ala His Asp Asn Asp His Phe Thr Ser Pro Glu Gly Val Pro
                725                 730                 735

Gly Val Pro Glu Thr Asn Phe Asn Asn Arg Pro Asn Ser Phe Lys Val
            740                 745                 750

Leu Ser Pro Pro Arg Thr Cys Val Ala Tyr Tyr Arg Val Glu Glu Lys
        755                 760                 765

Ala Glu Lys Pro Lys Asp Glu Gly Ala Ala Ser Trp Gly Lys Ala Ala
    770                 775                 780
```

```
Pro Gly Tyr Ile Asp Val Glu Ala Thr Arg Val Lys Asp Ala Ala Asp
785                 790                 795                 800

Gly Glu Ala Thr Ser Gly Ser Lys Lys Ala Ser Thr Gly Gly Asp Ser
                805                 810                 815

Ser Lys Lys Gly Ile Asn Phe Val Phe Gly Ser Pro Asp Lys Asp Asn
                820                 825                 830

Lys

<210> SEQ ID NO 17
<211> LENGTH: 10143
<212> TYPE: DNA
<213> ORGANISM: Triticum aestivum

<400> SEQUENCE: 17
ggttccgcgc tgcatttcgg ccggcgggtt gagtgagatc tgggccactg accgactcac    60
tcgctcgctg cgcggggatg cgacgtttg cggtgtccgg cgcgaccctc ggtgtggcgc    120
ggcccgccgg cgccggcggc ggactgctgc cgcgatccgg ctcggagcgg aggggcgggg   180
tggacctgcc gtcgctgctc ctcaggaaga aggactcctc tcgtacgcct cgctcgctcg   240
ctccaatctc cccgtccatt tttgcccccc ttctctctcc ctatctgcgc gcgcatggcc   300
tgttcgatgc tgttccccag ttgatctcca tcaacgagag agatagctgg attaggcgat   360
cgcctgcgtc agtgtcaccc aggccctggt gttatcacgg cttttgatcat ctcctcccat   420 tctgatattt tctcactctt tcttctgttc ttgctgtaac tgcaagttgt agcattgtct    480
cactattgta gtcatccttg cattgcaggc gccgtcctga gccgcgcggc ctctccaggg    540
aaggtcctgg tgcctgacgg tgagagcgac gacttggcaa gtccggcgca acctgaagaa    600
ttacaggtac acaccatcgt gccgggaaat cttcatacaa tcgttattca cttaccaaat    660
gccggatgaa accaagccgc ggaggcgtca ggttttgagc ttcttctatc agcattgtgc    720
agtactgcac tgccttgtgc attttgttag ccgtggcccc gtgctggctc ttgggccact    780
gaaaactcag atggatgtgc attctagcaa gaacttcacg aaataatgca ctgtttgtgg    840
tttcgttagt ctgctctaca attgctattt tcgtgctgta gatacctgaa gacatcgagg    900
agcaaacggc tgaagtaaac atgacagggg ggactgcaga aaaacttgaa tcttcagaac    960
cgactcaagg cattgtggaa acaatcactg atggtgtaac caaggagtt aaggaactag   1020 tcgtggggga gaaaccgcga gttgtcccaa aaccaggaga tgggcagaaa atatacgaga   1080
ttgacccaac gctgaaagat tttcggagcc atcttgacta ccggtaatgc ctacccgcta   1140
ctttcgctca ttttgaatta aggtcctttc gtcatgcaaa tttggggaac atcaaagaga   1200
caaagactag ggaccactat ttcttacagt tcccctcatg gtctgagaat atgctgggac   1260
gtagatgtat aattgatggc tacaatttgc tcataattac gatacaaata actgtctctg   1320
atcattgcaa ttacagagtg gcaaactgat taaaatgtga tagatgggtt atagatttta   1380
ctttgctaat tcctctacca aattcctggg gaaaaaatc taccagttgg gcaacttagt   1440
ttcttatctt tgttgcctct tgttttggg gaaaacacac tgctaaattt gaatgatttt   1500
gggtatgcct ccgtggattc aacagataca gcgaatacag gagaattcgt gctgctattg   1560
accaacatga aggtggattg gaagcatttt ctcgtggtta tgaaaagctt ggatttaccc   1620
gcaggtaaat ttaaagcttc agtattatga agcgcctcca ctagtctact tgcatatctt   1680
acaagaaaat ttataattcc tgttttcgcc tctcttttt ccagtgctga aggtattgtc   1740
tagttgcata tcttataaga aaatttatgt tcctgttttc ccctattttc cagtgctgaa   1800
```

```
ggtatcactt accgagaatg ggctcctgga gcgcatgtac gtcttttaag tcttaacaga   1860
caccttccaa ttcattgtta atggtcacac tattcaccaa ctagcttact ggacttacaa   1920
cttagcttac tgaatactga ccagttgctc taaatttatg atctggcttt tgcatcctat   1980
tacagtctgc agcattagta ggtgacttca acaattggaa tccgaatgca gatactatga   2040
ccagagtatg tctacagctt ggcaatcttc cacctttgct tcataactac tgatacatct   2100
atttgtattt attttgctgt ttgcacattc cttaaagttg agcctcaact atatcatatc   2160
aaaatggtat aatttgtcag tgtcttaagc ttcagcctaa agattctact gaaattggtc   2220
catcttttg agattgaaaa tgagtatatt aaggatggat gaataggtgc aacactccca   2280
ttctttggta gaaccttctg cattatgtgt gtttttcat ctacaatgag catatttcca   2340
tgctatcagt gaaggtttgc tcctattgat gccgatattt gatatgatct tttcaggatg   2400
attatggtgt ttgggagatt ttcctcccta acaatgctga tggatcccca gctattcctc   2460
atggctcacg tgtaaaggta agctggccaa ttatttagtt gagcatgtag cattttcgaa   2520
ctctgcccac taagggtccc tttgcctttc tgttttctag atacgatgg atactccatc   2580
tggtgtgaag gattcaattt ctgcttggat caagttctct gtgcaggctc caggtgaaat   2640
accattcaat ggcatatatt atgatccacc tgaagaggta agtatcgatc tccattacat   2700
tattaaatga aatttccagt gttacggttt tttaataccc atttcgtgtc tcactgacat   2760
gtgagtcaag acaatacttt agaatttgga agtgacatat gcattaattc accttctaag   2820
ggctaagggg caagcaacca tggtgatgtt tgtatgcttg tgtgtgactt aagatcttat   2880
agctctttta tgtgttctct gttggttagg atattccatt ttgaccttt gtgaccattt   2940
actaaggata ttttacatgc aaatgcagga gaagtatgtc ttccaacatc ctcaacctaa   3000
acgaccagag tcactgagga tttatgaatc acacattgga atgagcagcc cagtatgtca   3060
ataagttatt tcacctgttt ctggtctgat ggtctattct atggattttt tagttctgtt   3120
atgtattgtt aacatataac atggtgcatt cacgtgacaa cctcgatttt attttctaat   3180
gttattgcaa tagctcggta taatgtaacc atgttactag cttaagatgg ttagggtttc   3240
ccacttagga tgtatgaaat atcgcattgg agcatctcca gcaagccatt ttttgacgg   3300
ttaacagcag gagctctgct tttcattata ggagagggaa atgctgtaca gactgaagtc   3360
agtcagagca aagtaactta gaatcattta tgggccaccc tgcacagggc agaaggcagg   3420
caggaacgat cctctacagc cgtcggattg cctccatcag aggaatcctg gccgttaatc   3480
atgctctggc ccagtggtca gaatgcatca accagactga ggtgctcgcc tccttattgg   3540
taaaggatgc agcggtacga gcctattgaa cagatcctgt tcaagtaagg ccgttctcca   3600
gcaagccatt tcctagctta ttaatgagag agagagaggg gggggtctg tattctgcga   3660
gcaattcaaa aacttccatt gttctgaggt gtacgcattg tagggatctc ccattatgaa   3720
gaggatatag ttaattcttt gtaacctact tggaaacttg agtcttgcgg catcgctaat   3780
atattctatc atcacaatac ttagaggatg catctgaata ttttagtggg atcttgcaca   3840
ggaaccgaag ataaattcat atgctaattt tagggatgag gtgctgccaa gaattaaaag   3900
gcttggatac aatgcagtgc agataatggc aatccaggag cattcatact atgcgagctt   3960
tgggtattca cacaatccat tttttctgt tctttttct gtatgcgcct cttcacccat   4020
ttggagctat tacatcctaa tgcttcgtgc acatagaata tttggatata attctttagt   4080
agacatatag tacaacaaca gttggtattt ctgacttgta tgaccatttt attgttgttg   4140
gcttgttcca ggtaccatgt tactaatttt tttgcaccaa gtagccgttt tggaactcca   4200
```

```
gaggacttaa aatccctgat cgatagagca catgagcttg gtttgcttgt tcttatggat   4260
attgttcata ggtaagtagt ccaattaatt ttagctgctt tactgtttat ctggtattct   4320
aaatggcagg gccgtatcga cgagtatttt tccattctat ataattgtgc tacatgactt   4380
cttttttctc agatgtatta aaccagttgg acatcaaatg tatttggtac atctagtaaa   4440
ctgacagttt caaaagaaca tcgttttgta atggcaacat gatttgatgc catagatgtg   4500
gactgagaag ttcagatgct atcaagaaaa ttaatcaact ggccatgtac tcgtggcact   4560
acatagagtt tgcaagttgg aaaactgaca gcaatacctc actgataagt agctaggccc   4620
cacttgccag cttcatatta gatgttactt ccctgttgaa ctcatttgaa catattactt   4680
aaagttcttc atttgtccta agtcaaactt ctttaagttt gaccaagtct actgaaaaat   4740
atatcaacat ctacaacacc aaattggttt cattagattc acaattttta ttttgttata   4800
ttagcacacc tttgatgttg tagatatcag cacattttc tacagacttg gtcaaatata   4860
gagaagtttg acttaggaca aatctagaac ttcaatcaat ttggatcaga ggggatagtc   4920
catactggtt gattatattc ggtaacatca ataatatag atagatgtca cactttaac   4980 aaaaaaatca gaccttgtca ccaaatatgt atcagaccat ctgtttgctt tagccacttg   5040
ttttcatatt tatgtgtttg tacctaatct atttttactt ctacttggtt tggttgattt   5100
tttttcagtt gcattgcttc atcaatgatt ttgtgtaccc tgcagtcatt catcaaataa   5160 taccccttgac ggcttgaatg gtttcgatgg cactgataca cattacttcc acggtggtcc   5220
acgtggccat cattggatgt gggattctcg tctattcaac tatgggagtt gggaagtatg   5280
tagctctgac ttctgtcacc atatttggct aactgttcct gttaaatctg ttcttacaca   5340
tgtcgatatt ctattcttat gtaggtattg agattcttac tgtcaaacgc gagatggtgg   5400
cttgaagaat ataagtttga tggatttcga tttgatgggg tgacctccat gatgtatact   5460
caccatggat tacaagtaag tcatcaagtg gtttcagtaa cttttttagg gcactgaaat   5520
aattgctatg catcataaca tgtatcatga tcaggacttg tgctacggag tcttagatag   5580
ttccctagta cgcttgtaca attttacctg atgagatcat ggacgattcg aagtgattat   5640
tatttatttt tcttctaagt ttgcttcttg ttctagatga catttactgg gaactatggc   5700
gagtattttg gatttgctac tgatgttgac gcggtagttt acttgatgct ggtcaacgat   5760
ctaattcatg gactttatcc tgatgctgta tccattggtg aagatgtaag tgcttacagt   5820
atttatgatt tttaaccagt taagtagttt tattttggga tcaggctgtt actctttttg   5880 ttagggtaa gatctctctt ttcataacaa tgctaattta taccttgtat gataatgcat   5940
cacttaggta atttgaaaag tgcaaggcca ttcaagctta cgagcatatt ttttgatggc   6000
tgtaatttat ttgatagtat gcttgtttgg gttttcagt aaatgggagt gtgtgactaa   6060
tgttgtatta gaaatgggca accttgtcaa ttgcttcaga aggctaactt agattccgta   6120
aacgcttcag aaatgagagg ctattcccat ggacatgaaa ttatacttca gtgtgttctg   6180
tacatgtatt tgtaagagca agagcaacat ggtttaactt aaattcctgc actgctatgg   6240
aatctcactg tatgttgtta gtgtaacatc cgcaaacaag taatcctgag ctttcaactc   6300
atgagaaaat atgaggttcc acttctgcca gcattaactg ttcacagttc taatttgtgt   6360
aactgtgaaa ttgttcaggt cagtggaatg cccacatttt gcatccctgt tccagatggt   6420
ggtgttggtt ttgactatcg cttgcatatg gctgtagcag ataaatggat tgaactcctc   6480
aagtaagtgc aggaatattg gtgattacat gcgcacaatg atctagatta caatttctaa   6540
```

```
atggtaaaag gaaaatatgt atgtgaatat ctagacattt tcctgttatc agcttgtata    6600
cgagaagtca tacatggttt aaatagcaaa tctcagaaat gtaatggcta gtgtctttat    6660
gctggacatt gtacattgcg ctgtagcagg ccagtcaaca cagttagcaa tattttcaga    6720
aacaataatt atttatatcc gtatatgggg aaagtaggta tataaactgt ggtcattaat    6780
tgtgttcacc ttttgtcctg tataagcatg ggcagtaggt aataaattta gccagataaa    6840
ataaatcgtt attaggttta caaaggaat atacagggtc atgtagcata tctagttgta    6900
attattgaaa aggctgacaa aaggctcggt aaaaaaaatc cagatacgca ggaacgcgac    6960
taaagctcaa atatttatag tggtctctgt tgcttgctgt atatttgtat ctgcacatat    7020
atgaaattac tactacacag ctgccaatct gtcatgatct gtgttctgct ttgtgctatt    7080
taaattttaa ttcgatacat tggcaataat aaacttaact attcaaccaa tttggtggat    7140
accagagatt tctgccctct tttcgtaatg ttgtgctcct gctgctgttc tctgctgtta    7200
caaaagctgt tctcagtttt tttacatcat tattttgtg tgtgagtact tttagcatgt    7260
ttttcgaagc tgtgagttgt tggtacttaa tacattcttg gtagtgtcca aatatgctgc    7320
agtctaattt agcatttctt taacacaggc aaagtgacga atcttggaaa atgggtgata    7380
ttgtgcacac cctaacaaat agaaggtggc ttgagaagtg tgtaacttat gcagaaagtc    7440
atgatcaagc actagttggt gacaagacta ttgcattctg gttgatggat aaggtactag    7500
ctgttacttt tggaccaaaa gaattacaca attgatttgt ctcatcagat tgctagtgtt    7560
ttcttgtgat aaagattggc tgcgtcaccc atcaccagct atttcccaac tgttacttga    7620
gcaaaatttg ctgaaaacgt accatgtggt actgtggcgg cttgtgaact ttgactgtta    7680
tggtgcaaat ttctgttctt attttttga ttgcttatgt taccgttcat ttgctcatcc    7740
ctttcagaga ccagccaaag tcacgtgtag ctgtgtgatc tattatctga atcttgagca    7800
aattttatta atagggtaaa acccaacgaa ttatttgctt gaattttaat atacagacgt    7860
atagtcacct ggtgctttct taaatgatta ccatagtgcc tgaaggctga atagttttg    7920
gcgtttcttg gacgccgcct aaaggagtga ttttgggtag attcctggtc gagccctcgt    7980
tacaacatac atttgggaga tatgcttagt aactgctctg ggaagtttgg tcagaagtct    8040
gcatctacac gctccttgag gttttattat gacgccatct ttgtaactag tggcagctgt    8100
aaggaaacac attcaaaagg aaacggtcac attattctag tcaggaccac cacactaaga    8160
ggaatattct gttccaattt tatgagtttt tgggactcca aagggaacaa aagtgtctca    8220
tattgtgctt ataactacag ttgttttttat accagtgtag ttccattcca ggacagttga    8280
tacttggtac tgtgctgtaa attattgatc tggcatagaa cagcatgaac atatcaagct    8340
ctctttgtgc aggatatgta tgatttcatg gctctggata ggccttcaac tcctcgcatt    8400
gatcgtggca tagcattaca taaaatgatc aggcttgtca ccatgggttt aggtggtgaa    8460
ggctatctta acttcatggg aaatgagttt gggcatcctg gtcagtcttt acaacttttaa    8520
ttgcattctg catagttgtg atttactgta atttgaacca tgctttgttt tcacattgta    8580
tgtattatgt aatctgttgc ttccaaggag gaagttaact tctatttact tggcagaatg    8640
gatagatttt ccaagaggtc cgcaaactct tccaaccggc aaagtctctcc ctggaaataa    8700
caatagttat gataaatgcc gccgtagatt tgatcttgta agttttagct tagctattac    8760
atttcctcac tagatcttta tcggccattt atttcttgat gaaatcataa tgtttgttag    8820
gaaagatcaa cattgctttt gtagttttgt agacgttaac ataaatatgt gttaagagtt    8880
gttgatcatt aagaatatca tgattttttg tagggagatg cagattttct tagatatcgt    8940
```

```
ggtatgcaag agttcgatca ggcaatgcag catcttgagg aaaaatatgg ggtatgtcac    9000
tggtttgtct ttgttgcata acaagtcaca gtttaacatt agtctcttca aatggtcaaa    9060
aaagtgtaga attaatttct gtaatgagat gaaaactgtg caaggcggg agctggaatt     9120 gctcttcacc aattaaaact attttcttga gcgatagtgt attgatacct ataccaacac    9180
tgacaatgta actgcagttt atgacatctg agcaccagta tgtttcacgg aaacacgagg    9240
aagataaggt gatcatcttc gaaagaggag atttggtatt tgttttcaac ttccactgga    9300
gcaatagctt ttttgactac cgtgttgggt gttccaggcc tgggaagtac aaggtatgct    9360
ttgcttttgc attgtccacc cttcaccagt agggttagtg ggggcttcta caacttttaa    9420
gtccacatgt atagagtttg ttggtcgtgc agctatcaat ataaagaata tgataatttg    9480
taaagaaaag aatttgttgc tcgagctgtt gtagtcatat aacatccccg aagcacatct    9540
actattcatt catattatct acttaagggt ttgttacaat ctttgtactc agttggactc    9600
actctaatac tggaactgtt taccgaatct accctaatca tcctagcagt tttagagcag    9660
ccccatttgg acagtccact gggtttagtt ggtttgtgac agtttctgct atttcttatc    9720
aggtggcctt agactccgac gatgcactct ttggtggatt cagcaggctt gatcatgatg    9780
tcgactactt cacaaccgta agtctgggcc aagcgttac ttgactcgtc ttgactcaac     9840
tgcttacaaa tctgaatcaa cttctcattt gctgatgccc ttgcaggaac atccgcatga    9900
caacaggccg cgctctttct cggtgtacac tccgagcaga actgcggtcg tgtatgccct    9960
tacagagtaa gaaccagcag ctgcttgtta caaggcaaag agagaactcc agagagctcg   10020
tggatcgtga gcgaagcgac gggcaacggc gcgaggctgc tctaagcgcc atgactggga   10080
ggggatcgtg cctcttcccc agatgccagg aggagcagat ggataggtag cttgttggtg   10140
agc                                                                 10143
```

<210> SEQ ID NO 18
<211> LENGTH: 823
<212> TYPE: PRT
<213> ORGANISM: Triticum aestivum

<400> SEQUENCE: 18

```
Met Ala Thr Phe Ala Val Ser Gly Ala Thr Leu Gly Val Ala Arg Pro
1               5                   10                  15

Ala Gly Ala Gly Gly Leu Leu Pro Arg Ser Gly Ser Glu Arg Arg
                20                  25                  30

Gly Gly Val Asp Leu Pro Ser Leu Leu Arg Lys Lys Asp Ser Ser
        35                  40                  45

Arg Ala Val Leu Ser Arg Ala Ala Ser Pro Gly Lys Val Leu Val Pro
    50                  55                  60

Asp Gly Glu Ser Asp Asp Leu Ala Ser Pro Ala Gln Pro Glu Glu Leu
65                  70                  75                  80

Gln Ile Pro Glu Asp Ile Glu Glu Gln Thr Ala Glu Val Asn Met Thr
                85                  90                  95

Gly Gly Thr Ala Glu Lys Leu Glu Ser Ser Glu Pro Thr Gln Gly Ile
                100                 105                 110

Val Glu Thr Ile Thr Asp Gly Val Thr Lys Gly Val Lys Glu Leu Val
            115                 120                 125

Val Gly Glu Lys Pro Arg Val Val Pro Lys Pro Gly Asp Gly Gln Lys
    130                 135                 140

Ile Tyr Glu Ile Asp Pro Thr Leu Lys Asp Phe Arg Ser His Leu Asp
```

```
                145                 150                 155                 160
Tyr Arg Tyr Ser Glu Tyr Arg Ile Arg Ala Ala Ile Asp Gln His
                165                 170                 175

Glu Gly Gly Leu Glu Ala Phe Ser Arg Gly Tyr Glu Lys Leu Gly Phe
                180                 185                 190

Thr Arg Ser Ala Glu Gly Ile Thr Tyr Arg Glu Trp Ala Pro Gly Ala
                195                 200                 205

His Ser Ala Ala Leu Val Gly Asp Phe Asn Asn Trp Asn Pro Asn Ala
                210                 215                 220

Asp Thr Met Thr Arg Asp Asp Tyr Gly Val Trp Glu Ile Phe Leu Pro
225                 230                 235                 240

Asn Asn Ala Asp Gly Ser Pro Ala Ile Pro His Gly Ser Arg Val Lys
                245                 250                 255

Ile Arg Met Asp Thr Pro Ser Gly Val Lys Asp Ser Ile Ser Ala Trp
                260                 265                 270

Ile Lys Phe Ser Val Gln Ala Pro Gly Glu Ile Pro Phe Asn Gly Ile
                275                 280                 285

Tyr Tyr Asp Pro Pro Glu Glu Glu Lys Tyr Val Phe Gln His Pro Gln
                290                 295                 300

Pro Lys Arg Pro Glu Ser Leu Arg Ile Tyr Glu Ser His Ile Gly Met
305                 310                 315                 320

Ser Ser Pro Glu Pro Lys Ile Asn Ser Tyr Ala Asn Phe Arg Asp Glu
                325                 330                 335

Val Leu Pro Arg Ile Lys Arg Leu Gly Tyr Asn Ala Val Gln Ile Met
                340                 345                 350

Ala Ile Gln Glu His Ser Tyr Tyr Ala Ser Phe Gly Tyr His Val Thr
                355                 360                 365

Asn Phe Phe Ala Pro Ser Ser Arg Phe Gly Thr Pro Glu Asp Leu Lys
                370                 375                 380

Ser Leu Ile Asp Arg Ala His Glu Leu Gly Leu Leu Val Leu Met Asp
385                 390                 395                 400

Ile Val His Ser His Ser Ser Asn Asn Thr Leu Asp Gly Leu Asn Gly
                405                 410                 415

Phe Asp Gly Thr Asp Thr His Tyr Phe His Gly Gly Pro Arg Gly His
                420                 425                 430

His Trp Met Trp Asp Ser Arg Leu Phe Asn Tyr Gly Ser Trp Glu Val
                435                 440                 445

Leu Arg Phe Leu Leu Ser Asn Ala Arg Trp Trp Leu Glu Glu Tyr Lys
                450                 455                 460

Phe Asp Gly Phe Arg Phe Asp Gly Val Thr Ser Met Met Tyr Thr His
465                 470                 475                 480

His Gly Leu Gln Met Thr Phe Thr Gly Asn Tyr Gly Glu Tyr Phe Gly
                485                 490                 495

Phe Ala Thr Asp Val Asp Ala Val Val Tyr Leu Met Leu Val Asn Asp
                500                 505                 510

Leu Ile His Gly Leu Tyr Pro Asp Ala Val Ser Ile Gly Glu Asp Val
                515                 520                 525

Ser Gly Met Pro Thr Phe Cys Ile Pro Val Pro Asp Gly Gly Val Gly
                530                 535                 540

Phe Asp Tyr Arg Leu His Met Ala Val Ala Asp Lys Trp Ile Glu Leu
545                 550                 555                 560

Leu Lys Gln Ser Asp Glu Ser Trp Lys Met Gly Asp Ile Val His Thr
                565                 570                 575
```

```
Leu Thr Asn Arg Arg Trp Leu Glu Lys Cys Val Thr Tyr Ala Glu Ser
            580                 585                 590

His Asp Gln Ala Leu Val Gly Asp Lys Thr Ile Ala Phe Trp Leu Met
        595                 600                 605

Asp Lys Asp Met Tyr Asp Phe Met Ala Leu Asp Arg Pro Ser Thr Pro
    610                 615                 620

Arg Ile Asp Arg Gly Ile Ala Leu His Lys Met Ile Arg Leu Val Thr
625                 630                 635                 640

Met Gly Leu Gly Gly Glu Gly Tyr Leu Asn Phe Met Gly Asn Glu Phe
                645                 650                 655

Gly His Pro Glu Trp Ile Asp Phe Pro Arg Gly Pro Gln Thr Leu Pro
            660                 665                 670

Thr Gly Lys Val Leu Pro Gly Asn Asn Asn Ser Tyr Asp Lys Cys Arg
        675                 680                 685

Arg Arg Phe Asp Leu Gly Asp Ala Asp Phe Leu Arg Tyr Arg Gly Met
    690                 695                 700

Gln Glu Phe Asp Gln Ala Met Gln His Leu Glu Glu Lys Tyr Gly Phe
705                 710                 715                 720

Met Thr Ser Glu His Gln Tyr Val Ser Arg Lys His Glu Glu Asp Lys
                725                 730                 735

Val Ile Ile Phe Glu Arg Gly Asp Leu Val Phe Val Phe Asn Phe His
            740                 745                 750

Trp Ser Asn Ser Phe Phe Asp Tyr Arg Val Gly Cys Ser Arg Pro Gly
        755                 760                 765

Lys Tyr Lys Val Ala Leu Ser Asp Ala Leu Phe Gly Gly Phe
    770                 775                 780

Ser Arg Leu Asp His Asp Val Asp Tyr Phe Thr Thr Glu His Pro His
785                 790                 795                 800

Asp Asn Arg Pro Arg Ser Phe Ser Val Tyr Thr Pro Ser Arg Thr Ala
                805                 810                 815

Val Val Tyr Ala Leu Thr Glu
            820

<210> SEQ ID NO 19
<211> LENGTH: 2860
<212> TYPE: DNA
<213> ORGANISM: Triticum aestivum
<220> FEATURE:
<221> NAME/KEY: misc_feature
<222> LOCATION: (2833)..(2833)
<223> OTHER INFORMATION: n is a, c, g, or t
<220> FEATURE:
<221> NAME/KEY: misc_feature
<222> LOCATION: (2854)..(2854)
<223> OTHER INFORMATION: n is a, c, g, or t

<400> SEQUENCE: 19
cgtgggttta agcaggagac gaggcggggt cagttgggca gttaggttgg atccgatccg      60
gctgcggcgg cggcgacggg atggctgcgc cggcattcgc agtttccgcg gcggggctgg     120
cccggccgtc ggctcctcga tccggcgggg cagagcggag ggggcgcggg gtggagctgc     180
agtcgccatc gctgctcttc ggccgcaaca agggcacccg ttcacccgt gccgtcggcg      240 tcggaggttc tggatggcgc gtggtcatgc gcgcgggggg gccgtccggg gaggtgatga     300
tccctgacgg cggtagtggc ggaacaccgc cttccatcga cggtcccgtt cagttcgatt     360
ctgatgatct gaaggttcca ttcattgatg atgaaacaag cctacaggat ggaggtgaag     420
```

```
atagtatttg gtcttcagag acaaatcagg ttagtgaaga aattgatgct gaagacacga    480
gcagaatgga caaagaatca tctacgaggg agaaattacg cattctgcca ccaccgggaa    540
atggacagca aatatacgag attgacccaa cgctccgaga ctttaagtac catcttgagt    600
atcgatatag cctatacagg agaatacgtt cagacattga tgaacacgaa ggaggcatgg    660
atgtattttc ccgcggttac gagaagtttg gatttatgcg cagcgctgaa ggtatcactt    720
accgagaatg ggctcctgga gcagattctg cagcattagt tggcgacttc aacaattggg    780
atccaaatgc agaccatatg agcaaaaatg accttggtgt ttgggagatt tttctgccaa    840
acaatgcaga tggttcgcca ccaattcctc acggctcacg ggtgaaggtg cgaatgggta    900
ctccatctgg gacaaaggat tcaattcctg cttggatcaa gtactccgtg cagactccag    960
gagatatacc atacaatgga atatattatg atcctcccga agaggagaag tatgtattca   1020
agcatcctca acctaaacga ccaaaatcat tgcggatata tgaaacacat gttggcatga   1080
gtagcccgga accaaagatc aacacatatg caaacttcag ggatgaggtg cttccaagaa   1140
ttaaaagact tggatacaat gcagtgcaaa taatggcaat ccaagagcac tcatactatg   1200
gaagctttgg gtaccatgtt accaatttct ttgcaccaag tagccgtttt gggtccccag   1260
aagatttaaa atctttgatt gatagagctc acgagcttgg cttggttgtc ctcatggatg   1320
ttgttcacag tcacgcgtca ataatacct tggacgggtt gaatggtttt gatggcacgg   1380
atacacatta cttccatggc ggttcacggg ccatcactg gatgtgggat tcccgtgtgt   1440
ttaactatgg gaataaggaa gttataaggt ttctactttc caatgcaaga tggtggctag   1500
aggagtataa gtttgatggt ttccgattcg atggcgcgac ctccatgatg tatacccatc   1560
atggattaca agtaaccttt acaggaagct accatgaata ttttggcttt gccactgatg   1620
tagatgcggt cgtttacttg atgctgatga atgatctaat tcatgggttt tatcctgaag   1680
ccgtaactat cggtgaagat gttagtggaa tgcctacatt tgcccttcct gttcaagttg   1740
gtggggttgg ttttgactat cgcttacata tggctgttgc ccgcaaatgg attgaacttc   1800
tcaaaggaaa cgatgaagct tgggagatgg gtaatattgt gcacacacta acaaacagaa   1860
ggtggctgga aaagtgtgtt acttatgctg aaagtcacga tcaagcactt gttggagaca   1920
agactattgc attctggttg atggacaagg atatgtatga tttcatggcg ctgaacggac   1980
cttcgacgcc taatattgat cgtggaatag cactgcataa aatgattaga cttatcacaa   2040
tgggtctagg aggagagggt tatcttaact ttatgggaaa tgagttcggg catcctgaat   2100
ggatagactt tccaagaggc ccacaagtac ttccaagtgg taagttcatc ccaggaaaca   2160
acaacagtta cgacaaatgc cgtcgaagat ttgacctggg tgatgcagaa tttcttaggt   2220
atcatggtat gcagcagttt gatcaggcaa tgcagcatct tgaggaaaaa tatggtttta   2280
tgacatcaga ccaccagtac gtatctcgga aacatgagga agataaggtg atcgtgtttg   2340
aaaaagggga cttggtattt gtgttcaact tccactggag tagtagctat ttcgactacc   2400
gggtcggctg tttaaagcct gggaagtaca aggtggtctt agactcggac gctggactct   2460
ttggtggatt tggtaggatc catcacactg cagagcactt cacttctgac tgccaacatg   2520
acaacaggcc ccattcattc tcagtgtaca ctcctagcag aacctgtgtt gtctatgctc   2580
caatgaacta acagcaaagt gcagcatacg cgtgcgcgct gttgttgcta gtagcaagaa   2640
aaatcgtatg gtcaatacaa ccaggtgcaa ggtttaataa ggattttgc ttcaacgagt    2700
cctggataga caagacaaca tgatgttgtg ctgtgtgctc ccaatcccca gggcgttgtg   2760
aagaaaacat gctcatctgt gttatttat ggatcagcga cgaaacctcc cccaaatacc   2820
```

```
cctttttttt ttnaaaggag gataggcccc cggncttttgc                        2860
```

<210> SEQ ID NO 20
<211> LENGTH: 836
<212> TYPE: PRT
<213> ORGANISM: Triticum aestivum

<400> SEQUENCE: 20

| Met | Ala | Ala | Pro | Ala | Phe | Ala | Val | Ser | Ala | Gly | Leu | Ala | Arg | Pro |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Ser Ala Pro Arg Ser Gly Gly Ala Glu Arg Arg Gly Arg Gly Val Glu
            20                  25                  30

Leu Gln Ser Pro Ser Leu Leu Phe Gly Arg Asn Lys Gly Thr Arg Ser
                35                  40                  45

Pro Arg Ala Val Gly Val Gly Ser Gly Trp Arg Val Val Met Arg
 50                  55                  60

Ala Gly Gly Pro Ser Gly Glu Val Met Ile Pro Asp Gly Gly Ser Gly
 65                  70                  75                  80

Gly Thr Pro Pro Ser Ile Asp Gly Pro Val Gln Phe Ser Asp Asp
                 85                  90                  95

Leu Lys Val Pro Phe Ile Asp Asp Glu Thr Ser Leu Gln Asp Gly Gly
                100                 105                 110

Glu Asp Ser Ile Trp Ser Ser Glu Thr Asn Gln Val Ser Glu Glu Ile
                115                 120                 125

Asp Ala Glu Asp Thr Ser Arg Met Asp Lys Glu Ser Ser Thr Arg Glu
            130                 135                 140

Lys Leu Arg Ile Leu Pro Pro Gly Asn Gly Gln Gln Ile Tyr Glu
145                 150                 155                 160

Ile Asp Pro Thr Leu Arg Asp Phe Lys Tyr His Leu Glu Tyr Arg Tyr
                165                 170                 175

Ser Leu Tyr Arg Arg Ile Arg Ser Asp Ile Asp Glu His Glu Gly Gly
                180                 185                 190

Met Asp Val Phe Ser Arg Gly Tyr Glu Lys Phe Gly Phe Met Arg Ser
            195                 200                 205

Ala Glu Gly Ile Thr Tyr Arg Glu Trp Ala Pro Gly Ala Asp Ser Ala
    210                 215                 220

Ala Leu Val Gly Asp Phe Asn Asn Trp Asp Pro Asn Ala Asp His Met
225                 230                 235                 240

Ser Lys Asn Asp Leu Gly Val Trp Glu Ile Phe Leu Pro Asn Asn Ala
                245                 250                 255

Asp Gly Ser Pro Pro Ile Pro His Gly Ser Arg Val Lys Val Arg Met
            260                 265                 270

Gly Thr Pro Ser Gly Thr Lys Asp Ser Ile Pro Ala Trp Ile Lys Tyr
        275                 280                 285

Ser Val Gln Thr Pro Gly Asp Ile Pro Tyr Asn Gly Ile Tyr Tyr Asp
    290                 295                 300

Pro Pro Glu Glu Glu Lys Tyr Val Phe Lys His Pro Gln Pro Lys Arg
305                 310                 315                 320

Pro Lys Ser Leu Arg Ile Tyr Glu Thr His Val Gly Met Ser Ser Pro
                325                 330                 335

Glu Pro Lys Ile Asn Thr Tyr Ala Asn Phe Arg Asp Glu Val Leu Pro
            340                 345                 350

Arg Ile Lys Arg Leu Gly Tyr Asn Ala Val Gln Ile Met Ala Ile Gln
        355                 360                 365

-continued

```
Glu His Ser Tyr Tyr Gly Ser Phe Gly Tyr His Val Thr Asn Phe Phe
    370                 375                 380
Ala Pro Ser Ser Arg Phe Gly Ser Pro Glu Asp Leu Lys Ser Leu Ile
385                 390                 395                 400
Asp Arg Ala His Glu Leu Gly Leu Val Val Leu Met Asp Val Val His
                405                 410                 415
Ser His Ala Ser Asn Asn Thr Leu Asp Gly Leu Asn Gly Phe Asp Gly
                420                 425                 430
Thr Asp Thr His Tyr Phe His Gly Gly Ser Arg Gly His His Trp Met
                435                 440                 445
Trp Asp Ser Arg Val Phe Asn Tyr Gly Asn Lys Glu Val Ile Arg Phe
    450                 455                 460
Leu Leu Ser Asn Ala Arg Trp Trp Leu Glu Glu Tyr Lys Phe Asp Gly
465                 470                 475                 480
Phe Arg Phe Asp Gly Ala Thr Ser Met Met Tyr Thr His His Gly Leu
                485                 490                 495
Gln Val Thr Phe Thr Gly Ser Tyr His Glu Tyr Phe Gly Phe Ala Thr
                500                 505                 510
Asp Val Asp Ala Val Val Tyr Leu Met Leu Met Asn Asp Leu Ile His
                515                 520                 525
Gly Phe Tyr Pro Glu Ala Val Thr Ile Gly Glu Asp Val Ser Gly Met
    530                 535                 540
Pro Thr Phe Ala Leu Pro Val Gln Val Gly Gly Val Gly Phe Asp Tyr
545                 550                 555                 560
Arg Leu His Met Ala Val Ala Arg Lys Trp Ile Glu Leu Leu Lys Gly
                565                 570                 575
Asn Asp Glu Ala Trp Glu Met Gly Asn Ile Val His Thr Leu Thr Asn
                580                 585                 590
Arg Arg Trp Leu Glu Lys Cys Val Thr Tyr Ala Glu Ser His Asp Gln
                595                 600                 605
Ala Leu Val Gly Asp Lys Thr Ile Ala Phe Trp Leu Met Asp Lys Asp
    610                 615                 620
Met Tyr Asp Phe Met Ala Leu Asn Gly Pro Ser Thr Pro Asn Ile Asp
625                 630                 635                 640
Arg Gly Ile Ala Leu His Lys Met Ile Arg Leu Ile Thr Met Gly Leu
                645                 650                 655
Gly Gly Glu Gly Tyr Leu Asn Phe Met Gly Asn Glu Phe Gly His Pro
                660                 665                 670
Glu Trp Ile Asp Phe Pro Arg Gly Pro Gln Val Leu Pro Ser Gly Lys
    675                 680                 685
Phe Ile Pro Gly Asn Asn Asn Ser Tyr Asp Lys Cys Arg Arg Arg Phe
    690                 695                 700
Asp Leu Gly Asp Ala Glu Phe Leu Arg Tyr His Gly Met Gln Gln Phe
705                 710                 715                 720
Asp Gln Ala Met Gln His Leu Glu Glu Lys Tyr Gly Phe Met Thr Ser
                725                 730                 735
Asp His Gln Tyr Val Ser Arg Lys His Glu Glu Asp Lys Val Ile Val
                740                 745                 750
Phe Glu Lys Gly Asp Leu Val Phe Val Phe Asn Phe His Trp Ser Ser
    755                 760                 765
Ser Tyr Phe Asp Tyr Arg Val Gly Cys Leu Lys Pro Gly Lys Tyr Lys
770                 775                 780
```

Val Val Leu Asp Ser Asp Ala Gly Leu Phe Gly Gly Phe Gly Arg Ile
785                 790                 795                 800

His His Thr Ala Glu His Phe Thr Ser Asp Cys Gln His Asp Asn Arg
            805                 810                 815

Pro His Ser Phe Ser Val Tyr Thr Pro Ser Arg Thr Cys Val Val Tyr
            820                 825                 830

Ala Pro Met Asn
        835

<210> SEQ ID NO 21
<211> LENGTH: 5346
<212> TYPE: DNA
<213> ORGANISM: Triticum aestivum

<400> SEQUENCE: 21

```
cggcacgagg tttagtaggt tccgggaaat ggagatgtct ctctggccac ggagccccct      60
gtgccctcgg agcaggcagc cgctcgtcgt cgtccggccg ccggccgcg gcggcctcac     120
gcagccttt ttgatgaatg cagatttac tcgaagcagg acccttcgat gcatggtagc      180
aagttcagat cctcctaata ggaaatcaag aaggatggta ccacctcagg ttaaagtcat    240
ttcttctaga ggatatacga caagactcat tgttgaacca agcaacgaga atacagaaca    300
caataatcgg gatgaagaaa ctcttgatac atacaatgcg ctattaagta ccgagacagc    360
agaatggaca gataatagag aagccgagac tgctaaagcg gactcgtcgc aaaatgcttt    420
aagcagttct ataattgggg aagtggatgt ggcggatgaa gatatacttg cggctgatct    480
gacagtgtat tcattgagca gtgtaatgaa gaaggaagtg gatgcagcgg acaaagctag    540
agttaaagaa gacgcatttg agctggattt gccagcaact acattgagaa gtgtgatagt    600
agatgtgatg gatcataatg ggactgtaca agagacattg agaagtgtga tagtagatgt    660
gatggatcat aatgggactg tacaagagac attgagaagt gtgatagtag atgtgatgga    720
tgatgcggcg gacaaagcta gagttgaaga agacgtattt gagctggatt tgtcaggaaa    780
tatttcaagc agtgcgacga ccgtggaact agatgcggtt gacgaagtcg ggcctgttca    840
agacaaattt gaggcgacct catcaggaaa tgtttcaaac agtgcaacgg tacgggaagt    900
ggatgcaagt gatgaagctg ggaatgatca aggcatattt agagcagatt tgtcaggaaa    960
tgttttttca agcagtacaa cagtggaagt gggtgcagtg gatgaagctg ggtctataaa   1020
ggacaggttt gagacggatt cgtcaggaaa tgtttcaaca agtgcgccga tgtgggatgc   1080
aattgatgaa accgtggctg atcaagacac atttgaggcg gatttgtcgg gaaatgcttc   1140
aagctgcgca acatacagag aagtggatga tgtggtggat gaaactagat cagaagagga   1200
aacatttgca atggatttgt ttgcaagtga atcaggccat gagaaacata tggcagtgga   1260
ttatgtgggt gaagctaccg atgaagaaga gacttaccaa cagcaatatc cagtaccgtc   1320
ttcattctct atgtgggaca aggctattgc taaaacaggt gtaagtttga atcctgagct   1380
gcgacttgtc agggttgaag aacaaggcaa agtaaatttt agtgataaaa aagacctgtc   1440
aattgatgat ttaccaggac aaaaccaatc gatcattggt tcctataaac aagataaatc   1500
aattgctgat gttgcgggac cgacccaatc aatttttggt tctagtaaac aacaccggtc   1560
aattgttgct ttccccaaac aaaaccagtc aattgttagt gtcactgagc aaaagcagtc   1620
catagttgga ttccgtagtc aagatctttc ggctgttagt ctccctaaac aaaacgtacc   1680
aattgttggt acgtcgagag agggtcaaac aaagcaagtt cctgttgttg atagacagga   1740
tgcattgtat gtgaatggac tggaagctaa ggagggagat cacacatccg agaaaactga   1800
```

```
tgaggatgcg cttcatgtaa agtttaatgt tgacaatgtg ttgcggaagc atcaggcaga    1860
tagaacccaa gcagtggaaa agaaaacttg gaagaaagtt gatgaggaac atctttacat    1920
gactgaacat cagaaacgtg ctgccgaagg acagatggta gttaacgagg atgagctttc    1980
tataactgaa attggaatgg ggagaggtga taaaattcag catgtgcttt ctgaggaaga    2040
gctttcatgg tctgaagatg aagtgcagtt aattgaggat gatggacaat atgaagttga    2100
cgagacctct gtgtccgtta acgttgaaca agatatccag gggtcaccac aggatgttgt    2160
ggatccgcaa gcactaaagg tgatgctgca agaactcgct gagaaaaatt attcgatgag    2220
gaacaagctg tttgttttc cagaggtagt gaaagctgat tcagttattg atctttattt    2280
aaatcgtgac ctaacagctt tggcgaatga acccgatgtc gtcatcaaag gagcattcaa    2340
tggttggaaa tggaggcttt tcactgaaag attgcacaag agtgaccttg gaggggtttg    2400
gtggtcttgc aaactgtaca tacccaagga ggcctacaga ttagactttg tgttcttcaa    2460
cggtcgcacg gtctatgaga acaatggcaa caatgatttc tgtataggaa tagaaggcac    2520
tatgaatgaa gatctgtttg aggatttctt ggttaaagaa aagcaaaggg agcttgagaa    2580
acttgccatg gaagaagctg aaaggaggac acagactgaa gaacagcggc gaagaaagga    2640
agcaagggct gcagatgaag ctgtcagggc acaagcgaag gccgagatag agatcaagaa    2700
gaaaaaattg caaagtatgt tgagtttggc cagaacatgt gttgataatt tgtggtacat    2760
agaggctagc acagatacaa gaggagatac tatcaggtta tattataaca gaaactcgag    2820
gccacttgcg catagtactg agatttggat gcatggtggt tacaacaatt ggacagatgg    2880
actctctatt gttgaaagct tgtcaagtg caatgacaaa gacggcgatt ggtggtatgc    2940
agatgttatt ccacctgaaa aggcacttgt gttggactgg gttttttgctg atgggccagc    3000 tgggaatgca aggaactatg acaacaatgc tcgacaagat ttccatgcta ttcttccgaa    3060
caacaatgta accgaggaag gcttctgggc gcaagaggag caaaacatct atacaaggct    3120
tctgcaagaa aggagagaaa aggaagaaac catgaaaaga aaggctgaga gaagtgcaaa    3180
tatcaaagct gagatgaagg caaaaactat gcgaaggttt ctgctttccc agaaacacat    3240
tgtttatacc gaaccgcttg aaatacgtgc cggaaccaca gtggatgtgc tatacaatcc    3300
ctctaacaca gtgctaaatg aaagtcgga gggttggttt agatgctcct ttaacctttg    3360
gatgcattca agtggggcat tgccacccca gaagatggtg aaatcagggg atgggccgct    3420
cttaaaagca acagttgatg ttccaccgga tgcctatatg atggactttg ttttctccga    3480
gtgggaagaa gatgggatct atgacaacag gaatgggatg gactatcata ttcctgtttc    3540
tgattcaatt gaaacagaga attacatgcg tattatccac attgccgttg agatggcccc    3600
cgttgcaaag gttggaggtc ttgggggatgt tgttacaagt ctttcacgtg ccattcaaga    3660
tctaggacat actgtcgagg ttattctccc gaagtacgac tgtttgaacc aaagcagtgt    3720
caaggattta catttatatc aaagtttttc ttggggtggt acagaaataa agtatgggt    3780 tggacgagtc gaagacctga ccgtttactt cctggaacct caaaatggga tgtttggcgt    3840
tggatgtgta tatggaagga atgatgaccg cagatttggg ttcttctgtc attctgctct    3900
agagtttatc ctccagaatg aatttctctc acatataata cattgccatg attggtcaag    3960
tgctccggtc gcctggctat ataaggaaca ctattcccaa tccagaatgg caagcactcg    4020
ggttgtattt accatccaca atcttgaatt tggagcacat tatattggta aagcaatgac    4080
atactgtgat aaagccacaa ctgtttctcc tacatattca agggacgtgg caggccatgg    4140
```

```
cgccattgct cctcatcgtg agaaattcta cggcattctc aatggaattg atccagatat    4200
ctgggatccg tacactgaca attttatccc ggtcccttat acttgtgaga atgttgtcga    4260
aggcaagaga gctgcaaaaa gggccttgca gcagaagttt ggattacagc aaactgatgt    4320
ccctattgtc ggaatcatca cccgtctgac agcccagaag ggaatccacc tcatcaagca    4380
cgcaattcac cgaactctcg aaagcaacgg acatgtggtt ttgcttggtt cagctccaga    4440
tcatcgaata caaggcgatt tttgcagatt ggccgatgct cttcatggtg tttaccatgg    4500
tagggtgaag cttgttctaa cctatgatga gcctctttct cacctgatat acgctggctc    4560
ggacttcata attgttcctt caatcttcga accctgtggc ttaacacaac ttgttgccat    4620
gcgttatgga tcgatcccta tagttcggaa aactggagga cttcacgaca cagtcttcga    4680
cgtagacaat gataaggacc gggctcggtc tcttggtctt gaaccaaatg ggttcagttt    4740
cgacggagcc gacagcaatg cgtggatta tgccctcaac agagcaatcg gcgcttggtt    4800
cgatgcccgt gattggttcc actccctgtg taagagggtc atggagcaag actggtcgtg    4860
gaaccggccc gcactggact acattgaatt gtaccatgcc gctcgaaaat tctgacaccc    4920
aactgaacca atgacaagaa caagcgcatt gtgggatcga ctagtcatac agggctgtgc    4980
agatcgtctt gcttcagtta gtgccctctt cagttagttc caagcgcact acagtcgtac    5040
atagctgagg atcctcttgc ctcctaccag ggggaacaaa gcagaaatgc atgagtgcat    5100
tgggaagact tttatgtata ttgttaaaaa aatttccttt tcttttcctt ccctgcacct    5160
ggaaatggtt aagcgcatcg ccgagataag aaccgcagtg acattctgtg agtagctttg    5220
tatattctct catcttgtga aaactaatgt tcatgttagg ctgtctgatc atgtggaagc    5280
tttgttatat gttacttatg gtatacatca atgatattta catttgtgga aaaaaaaaaa    5340
aaaaaa                                                              5346
```

<210> SEQ ID NO 22
<211> LENGTH: 1628
<212> TYPE: PRT
<213> ORGANISM: Triticum aestivum

<400> SEQUENCE: 22

```
Met Glu Met Ser Leu Trp Pro Arg Ser Pro Leu Cys Pro Arg Ser Arg
1               5                   10                  15

Gln Pro Leu Val Val Arg Pro Ala Gly Arg Gly Gly Leu Thr Gln
            20                  25                  30

Pro Phe Leu Met Asn Gly Arg Phe Thr Arg Ser Arg Thr Leu Arg Cys
        35                  40                  45

Met Val Ala Ser Ser Asp Pro Pro Asn Arg Lys Ser Arg Arg Met Val
    50                  55                  60

Pro Pro Gln Val Lys Val Ile Ser Ser Arg Gly Tyr Thr Thr Arg Leu
65                  70                  75                  80

Ile Val Glu Pro Ser Asn Glu Asn Thr Glu His Asn Asn Arg Asp Glu
                85                  90                  95

Glu Thr Leu Asp Thr Tyr Asn Ala Leu Leu Ser Thr Glu Thr Ala Glu
            100                 105                 110

Trp Thr Asp Asn Arg Glu Ala Glu Thr Ala Lys Ala Asp Ser Ser Gln
        115                 120                 125

Asn Ala Leu Ser Ser Ser Ile Ile Gly Glu Val Asp Val Ala Asp Glu
    130                 135                 140

Asp Ile Leu Ala Ala Asp Leu Thr Val Tyr Ser Leu Ser Ser Val Met
145                 150                 155                 160
```

-continued

```
Lys Lys Glu Val Asp Ala Ala Asp Lys Ala Arg Val Lys Glu Asp Ala
            165                 170                 175
Phe Glu Leu Asp Leu Pro Ala Thr Thr Leu Arg Ser Val Ile Val Asp
            180                 185                 190
Val Met Asp His Asn Gly Thr Val Gln Glu Thr Leu Arg Ser Val Ile
            195                 200                 205
Val Asp Val Met Asp His Asn Gly Thr Val Gln Glu Thr Leu Arg Ser
            210                 215                 220
Val Ile Val Asp Val Met Asp Ala Ala Asp Lys Ala Arg Val Glu
225                 230                 235                 240
Glu Asp Val Phe Glu Leu Asp Leu Ser Gly Asn Ile Ser Ser Ser Ala
            245                 250                 255
Thr Thr Val Glu Leu Asp Ala Val Asp Glu Val Gly Pro Val Gln Asp
            260                 265                 270
Lys Phe Glu Ala Thr Ser Ser Gly Asn Val Ser Asn Ser Ala Thr Val
            275                 280                 285
Arg Glu Val Asp Ala Ser Asp Glu Ala Gly Asn Asp Gln Gly Ile Phe
            290                 295                 300
Arg Ala Asp Leu Ser Gly Asn Val Phe Ser Ser Thr Thr Val Glu
305                 310                 315                 320
Val Gly Ala Val Asp Glu Ala Gly Ser Ile Lys Asp Arg Phe Glu Thr
            325                 330                 335
Asp Ser Ser Gly Asn Val Ser Thr Ser Ala Pro Met Trp Asp Ala Ile
            340                 345                 350
Asp Glu Thr Val Ala Asp Gln Asp Thr Phe Glu Ala Asp Leu Ser Gly
            355                 360                 365
Asn Ala Ser Ser Cys Ala Thr Tyr Arg Glu Val Asp Asp Val Val Asp
            370                 375                 380
Glu Thr Arg Ser Glu Glu Thr Phe Ala Met Asp Leu Phe Ala Ser
385                 390                 395                 400
Glu Ser Gly His Glu Lys His Met Ala Val Asp Tyr Val Gly Glu Ala
            405                 410                 415
Thr Asp Glu Glu Glu Thr Tyr Gln Gln Gln Tyr Pro Val Pro Ser Ser
            420                 425                 430
Phe Ser Met Trp Asp Lys Ala Ile Ala Lys Thr Gly Val Ser Leu Asn
            435                 440                 445
Pro Glu Leu Arg Leu Val Arg Val Glu Glu Gln Gly Lys Val Asn Phe
450                 455                 460
Ser Asp Lys Lys Asp Leu Ser Ile Asp Asp Leu Pro Gly Gln Asn Gln
465                 470                 475                 480
Ser Ile Ile Gly Ser Tyr Lys Gln Asp Lys Ser Ile Ala Asp Val Ala
            485                 490                 495
Gly Pro Thr Gln Ser Ile Phe Gly Ser Ser Lys Gln His Arg Ser Ile
            500                 505                 510
Val Ala Phe Pro Lys Gln Asn Gln Ser Ile Val Ser Val Thr Glu Gln
            515                 520                 525
Lys Gln Ser Ile Val Gly Phe Arg Ser Gln Asp Leu Ser Ala Val Ser
            530                 535                 540
Leu Pro Lys Gln Asn Val Pro Ile Val Gly Thr Ser Arg Glu Gly Gln
545                 550                 555                 560
Thr Lys Gln Val Pro Val Val Asp Arg Gln Asp Ala Leu Tyr Val Asn
            565                 570                 575
```

-continued

```
Gly Leu Glu Ala Lys Glu Gly Asp His Thr Ser Glu Lys Thr Asp Glu
                580                 585                 590

Asp Ala Leu His Val Lys Phe Asn Val Asp Asn Val Leu Arg Lys His
            595                 600                 605

Gln Ala Asp Arg Thr Gln Ala Val Glu Lys Lys Thr Trp Lys Lys Val
        610                 615                 620

Asp Glu Glu His Leu Tyr Met Thr Glu His Gln Lys Arg Ala Ala Glu
625                 630                 635                 640

Gly Gln Met Val Val Asn Glu Asp Glu Leu Ser Ile Thr Glu Ile Gly
                645                 650                 655

Met Gly Arg Gly Asp Lys Ile Gln His Val Leu Ser Glu Glu Leu
                660                 665                 670

Ser Trp Ser Glu Asp Glu Val Gln Leu Ile Glu Asp Gly Gln Tyr
        675                 680                 685

Glu Val Asp Glu Thr Ser Val Ser Val Asn Val Glu Gln Asp Ile Gln
            690                 695                 700

Gly Ser Pro Gln Asp Val Val Asp Pro Gln Ala Leu Lys Val Met Leu
705                 710                 715                 720

Gln Glu Leu Ala Glu Lys Asn Tyr Ser Met Arg Asn Lys Leu Phe Val
                725                 730                 735

Phe Pro Glu Val Val Lys Ala Asp Ser Val Ile Asp Leu Tyr Leu Asn
            740                 745                 750

Arg Asp Leu Thr Ala Leu Ala Asn Glu Pro Asp Val Ile Lys Gly
        755                 760                 765

Ala Phe Asn Gly Trp Lys Trp Arg Leu Phe Thr Glu Arg Leu His Lys
770                 775                 780

Ser Asp Leu Gly Gly Val Trp Trp Ser Cys Lys Leu Tyr Ile Pro Lys
785                 790                 795                 800

Glu Ala Tyr Arg Leu Asp Phe Val Phe Phe Asn Gly Arg Thr Val Tyr
                805                 810                 815

Glu Asn Asn Gly Asn Asn Asp Phe Cys Ile Gly Ile Glu Gly Thr Met
            820                 825                 830

Asn Glu Asp Leu Phe Glu Asp Phe Leu Val Lys Glu Lys Gln Arg Glu
        835                 840                 845

Leu Glu Lys Leu Ala Met Glu Glu Ala Glu Arg Arg Thr Gln Thr Glu
850                 855                 860

Glu Gln Arg Arg Arg Lys Glu Ala Arg Ala Ala Asp Glu Ala Val Arg
865                 870                 875                 880

Ala Gln Ala Lys Ala Glu Ile Glu Ile Lys Lys Lys Leu Gln Ser
                885                 890                 895

Met Leu Ser Leu Ala Arg Thr Cys Val Asp Asn Leu Trp Tyr Ile Glu
            900                 905                 910

Ala Ser Thr Asp Thr Arg Gly Asp Thr Ile Arg Leu Tyr Tyr Asn Arg
        915                 920                 925

Asn Ser Arg Pro Leu Ala His Ser Thr Glu Ile Trp Met His Gly Gly
930                 935                 940

Tyr Asn Asn Trp Thr Asp Gly Leu Ser Ile Val Glu Ser Phe Val Lys
945                 950                 955                 960

Cys Asn Asp Lys Asp Gly Asp Trp Trp Tyr Ala Asp Val Ile Pro Pro
                965                 970                 975

Glu Lys Ala Leu Val Leu Asp Trp Val Phe Ala Asp Gly Pro Ala Gly
            980                 985                 990

Asn Ala Arg Asn Tyr Asp Asn Asn  Ala Arg Gln Asp Phe  His Ala Ile
```

-continued

```
            995                 1000                1005
Leu Pro Asn Asn Asn Val Thr Glu Glu Gly Phe Trp Ala Gln Glu
    1010                1015                1020

Glu Gln Asn Ile Tyr Thr Arg Leu Leu Gln Glu Arg Arg Glu Lys
    1025                1030                1035

Glu Glu Thr Met Lys Arg Lys Ala Glu Arg Ser Ala Asn Ile Lys
    1040                1045                1050

Ala Glu Met Lys Ala Lys Thr Met Arg Arg Phe Leu Leu Ser Gln
    1055                1060                1065

Lys His Ile Val Tyr Thr Glu Pro Leu Glu Ile Arg Ala Gly Thr
    1070                1075                1080

Thr Val Asp Val Leu Tyr Asn Pro Ser Asn Thr Val Leu Asn Gly
    1085                1090                1095

Lys Ser Glu Gly Trp Phe Arg Cys Ser Phe Asn Leu Trp Met His
    1100                1105                1110

Ser Ser Gly Ala Leu Pro Pro Gln Lys Met Val Lys Ser Gly Asp
    1115                1120                1125

Gly Pro Leu Leu Lys Ala Thr Val Asp Val Pro Asp Ala Tyr
    1130                1135                1140

Met Met Asp Phe Val Phe Ser Glu Trp Glu Glu Asp Gly Ile Tyr
    1145                1150                1155

Asp Asn Arg Asn Gly Met Asp Tyr His Ile Pro Val Ser Asp Ser
    1160                1165                1170

Ile Glu Thr Glu Asn Tyr Met Arg Ile Ile His Ile Ala Val Glu
    1175                1180                1185

Met Ala Pro Val Ala Lys Val Gly Gly Leu Gly Asp Val Val Thr
    1190                1195                1200

Ser Leu Ser Arg Ala Ile Gln Asp Leu Gly His Thr Val Glu Val
    1205                1210                1215

Ile Leu Pro Lys Tyr Asp Cys Leu Asn Gln Ser Ser Val Lys Asp
    1220                1225                1230

Leu His Leu Tyr Gln Ser Phe Ser Trp Gly Gly Thr Glu Ile Lys
    1235                1240                1245

Val Trp Val Gly Arg Val Glu Asp Leu Thr Val Tyr Phe Leu Glu
    1250                1255                1260

Pro Gln Asn Gly Met Phe Gly Val Gly Cys Val Tyr Gly Arg Asn
    1265                1270                1275

Asp Asp Arg Arg Phe Gly Phe Phe Cys His Ser Ala Leu Glu Phe
    1280                1285                1290

Ile Leu Gln Asn Glu Phe Ser Pro His Ile Ile His Cys His Asp
    1295                1300                1305

Trp Ser Ser Ala Pro Val Ala Trp Leu Tyr Lys Glu His Tyr Ser
    1310                1315                1320

Gln Ser Arg Met Ala Ser Thr Arg Val Val Phe Thr Ile His Asn
    1325                1330                1335

Leu Glu Phe Gly Ala His Tyr Ile Gly Lys Ala Met Thr Tyr Cys
    1340                1345                1350

Asp Lys Ala Thr Thr Val Ser Pro Thr Tyr Ser Arg Asp Val Ala
    1355                1360                1365

Gly His Gly Ala Ile Ala Pro His Arg Glu Lys Phe Tyr Gly Ile
    1370                1375                1380

Leu Asn Gly Ile Asp Pro Asp Ile Trp Asp Pro Tyr Thr Asp Asn
    1385                1390                1395
```

```
Phe Ile Pro Val Pro Tyr Thr Cys Glu Asn Val  Glu Gly Lys
    1400            1405            1410

Arg Ala Ala Lys Arg Ala Leu Gln Gln Lys Phe  Gly Leu Gln Gln
1415            1420            1425

Thr Asp Val Pro Ile Val Gly Ile Ile Thr Arg  Leu Thr Ala Gln
    1430            1435            1440

Lys Gly Ile His Leu Ile Lys His Ala Ile His  Arg Thr Leu Glu
1445            1450            1455

Ser Asn Gly His Val Val Leu Leu Gly Ser Ala  Pro Asp His Arg
    1460            1465            1470

Ile Gln Gly Asp Phe Cys Arg Leu Ala Asp Ala  Leu His Gly Val
1475            1480            1485

Tyr His Gly Arg Val Lys Leu Val Leu Thr Tyr  Asp Glu Pro Leu
    1490            1495            1500

Ser His Leu Ile Tyr Ala Gly Ser Asp Phe Ile  Ile Val Pro Ser
1505            1510            1515

Ile Phe Glu Pro Cys Gly Leu Thr Gln Leu Val  Ala Met Arg Tyr
    1520            1525            1530

Gly Ser Ile Pro Ile Val Arg Lys Thr Gly Gly  Leu His Asp Thr
1535            1540            1545

Val Phe Asp Val Asp Asn Asp Lys Asp Arg Ala  Arg Ser Leu Gly
    1550            1555            1560

Leu Glu Pro Asn Gly Phe Ser Phe Asp Gly Ala  Asp Ser Asn Gly
1565            1570            1575

Val Asp Tyr Ala Leu Asn Arg Ala Ile Gly Ala  Trp Phe Asp Ala
    1580            1585            1590

Arg Asp Trp Phe His Ser Leu Cys Lys Arg Val  Met Glu Gln Asp
1595            1600            1605

Trp Ser Trp Asn Arg Pro Ala Leu Asp Tyr Ile  Glu Leu Tyr His
    1610            1615            1620

Ala Ala Arg Lys Phe
1625

<210> SEQ ID NO 23
<211> LENGTH: 3386
<212> TYPE: DNA
<213> ORGANISM: Triticum aestivum

<400> SEQUENCE: 23
gccgtttgcc cgacgaatgg caccgtgcca cgcccacggc cctcctccgc ctccgccccc      60
gcctcgcccg cgcgcggagc acgagacacg ccacgcgctg gccccggcc accgccaccg     120 ccaccagtcc accaccacca gtccaccacc accactcttc agcccactc cactccccgc     180 cgctttccgg cccgccgccc gcttcaagct ccccctcgccc caccagtcgc cctgcctctc     240
cctattcccc atggcgtgct ccgcggcgg gggcgtcgag gcgaccgcc tcctgtcccc     300 gcgctgcccc gccccttccc cgcccgacgg ccgctcccgc cgccgcctcg ccctcgcttc     360
ccgcacgcgc caccgcagcc tcagggcggc cgcgcagcgc cctcacaaga gcgcaaccgg     420
cgccgacccc ctttataaca acagggccaa tgtgcggagc gacgaggcgt cggtttccgc     480
tgaaaaagaa cggcaaagga aatacaacga tggagatggc atatcaaacc ttaagctgga     540
agatttggta ggaatgatac agaacaccga gaagaatata cttcttttga atcaagcccg     600
tcttcaggca atggaacacg ctgataaagt tcttaaagaa aaggaagcct tgcagagaaa     660
```

```
gataaacatt ttagagacga ggttgtcaga aacagatgaa caacataagc tttcaagtga      720
agggaatttc agtgactctc cactagcatt ggagcttggt attctaaagg aagagaacat      780
tctactgaag gaggacatag aattttttcaa aacaaagctt atagaggttg ccgagataga     840
ggagggtata ttcaaattgg agaaggagca tgctctttta gatgcttccc ttagggagct      900
ggagtctagg tttatagccg cccaagcaga tacgatgaaa cttggtccta gggatgcctg      960
gtgggagaaa gtagaaaaat tggaagactt gcttgagacc acagcaaacc aagtagagca     1020
tgctgctgtg atattggacc acaatcatga tctgcaggat aggcttgaca atttagaggc     1080
atcactgcaa gcagcaaata tttcaaagtt ctcttgttct cttgttgatc ttttgcagca     1140
aaaggtcaaa ttggtagaag accgcttcca agcatgtaac agcgaaatgc attctcagat     1200
tgaactgtac gagcattcaa tagtggaatt tcatgatact cttagcaaac taatagagga     1260
aagtgagaaa agatcactgg agaattttac aggaaacatg ccttcggaac tatggagcaa     1320 aatttcccctt ttaattgatg gatggttact ggagaagaaa atatcttaca atgacgcaag    1380
tatgttgcga gaaatggttc agaaaaggga cagtcgtctt cgggaagcat acttgtcata     1440
cagaggtacc gaaaacaggg aagttatgga caacttactt aagatggcat taccaggaac     1500
cagttctggt ttgcacatcg ctcacatagc agcagagatg ctcctgtcg cgaaggttgg      1560 tggcctggca gatgtgatat ctggtcttgg gaaggcactt cagaaaaaag gccatctagt     1620
agagatcatt cttcccaaat acgactgcat gcaggttgac caagttagca atctaaaggt     1680
tttagatgtt cttgtgcagt cctactttga aggaaatatg ttcaacaaca aaatttggac     1740
cgggactgtt gaaggcctac ccgtgtactt tattgagcca cagcatccag cgatgttctt     1800
ttcgagggct cagtactatg gagagcatga tgacttcaaa cgttttttcat acttcagccg    1860 tgcggcacta gaattacttt atcaatctgg gaagaaagtt gatataatcc actgccatga    1920
ctggcaaact gcatttgttg cacctcttta ttgggatgta tatgcaaatc taggcttcaa    1980
ctcagctaga atttgcttca cctgtcataa ttttgaatac caaggaactg ctccagctcg    2040
tgatttagca tggtgtggtc ttgatgttga gcacctagac agaccagaca ggatgcggga    2100
caattcgcat ggcagaataa atgctgttaa gggagcagtt gtgtattcaa acatcgtgac    2160
aactgtctcg ccaacatatg cactagaggt tcgctcagag ggtgggcgtg gactccaaga    2220
tacacttaaa gtacattcca ggaaatttct tgggatactt aatggaatcg acacagatac    2280
atggaaccct tgcacagata ggtatctcaa ggtccagtat aatgctaagg atctccaggg    2340
aaaggcagcc aacaaagcag ccctcagaga gcaactaaac ctggcttctg catatccttc    2400
acaaccactg gttggttgca ttaccaggct ggttgctcag aagggtgtac atcttatcag    2460
gcatgcaata tacaaaacag ctgaattagg aggacagttt gtccttctgg gttcaagtcc    2520
agtaccagaa attcagaggg agtttgaagg tattgcagac cattttcaga acaacaacaa    2580
tatccggctg attttgaagt atgatgatgc gctgtctcat tgcatatatg ctgcgtctga    2640
catgttcatt gttccctcta tatttgagcc atgtggcctc actcagatga tagccatgag    2700
atatggttct gtgccaatcg ttcggaaaac tggtgggctg aatgacagtg tctttgactt    2760
cgatgacgaa acaatacccca tggaggtgcg gaacggcttt acatttgtca aggccgacga    2820
gcagggccta agcagcgcga tggagagggc gttcaactgc tacacgagga agcccgaggt    2880
gtggaaacag cttgtgcaga aagacatgac gatcgatttc agctgggaca cctcggcttc    2940
gcagtacgag gacatctacc agaaggcggt ggctcgagcg agggcagtgg cgtgagcaca    3000
cacacacacg gtagttggtt ccctgatgcc tctctcccct gccctgccct catgatacaa    3060
```

```
acggcactgg acgaaatcga gggatcatgg aaacagaatc atatagcaag ctccatgctc    3120
tcggcgcgca tttccggtaa gggtgtgacg gtgtatcgct ggttatatgc gctgtttatt    3180
gaaggcagaa cgcgagctaa aaatggagta gctaccgtga accctcaaga tcgtagtatg    3240
cgcgctgttg ttggcataat attggtgtaa attgtagtag gctgtatatt ttcttgaggg    3300
gttgcaacgg agctgtatgc gtgcagtgca ggctgcagag tcgcacgtat gtactgtatt    3360
atgcagaaaa aaaaaaaaaa aaaaaa                                         3386

<210> SEQ ID NO 24
<211> LENGTH: 914
<212> TYPE: PRT
<213> ORGANISM: Triticum aestivum

<400> SEQUENCE: 24
```

Met Ala Cys Ser Ala Ala Ala Gly Val Glu Ala Thr Ala Leu Leu Ser
1               5                   10                  15

Pro Arg Cys Pro Ala Pro Ser Pro Pro Asp Gly Arg Ser Arg Arg Arg
            20                  25                  30

Leu Ala Leu Ala Ser Arg Thr Arg His Arg Ser Leu Arg Ala Ala Ala
        35                  40                  45

Gln Arg Pro His Lys Ser Ala Thr Gly Ala Asp Pro Leu Tyr Asn Asn
    50                  55                  60

Arg Ala Asn Val Arg Ser Asp Glu Ala Ser Val Ser Ala Glu Lys Glu
65                  70                  75                  80

Arg Gln Arg Lys Tyr Asn Asp Gly Asp Gly Ile Ser Asn Leu Lys Leu
                85                  90                  95

Glu Asp Leu Val Gly Met Ile Gln Asn Thr Glu Lys Asn Ile Leu Leu
            100                 105                 110

Leu Asn Gln Ala Arg Leu Gln Ala Met Glu His Ala Asp Lys Val Leu
        115                 120                 125

Lys Glu Lys Glu Ala Leu Gln Arg Lys Ile Asn Ile Leu Glu Thr Arg
    130                 135                 140

Leu Ser Glu Thr Asp Glu Gln His Lys Leu Ser Ser Glu Gly Asn Phe
145                 150                 155                 160

Ser Asp Ser Pro Leu Ala Leu Glu Leu Gly Ile Leu Lys Glu Glu Asn
                165                 170                 175

Ile Leu Leu Lys Glu Asp Ile Glu Phe Phe Lys Thr Lys Leu Ile Glu
            180                 185                 190

Val Ala Glu Ile Glu Glu Gly Ile Phe Lys Leu Glu Lys Glu His Ala
        195                 200                 205

Leu Leu Asp Ala Ser Leu Arg Glu Leu Glu Ser Arg Phe Ile Ala Ala
    210                 215                 220

Gln Ala Asp Thr Met Lys Leu Gly Pro Arg Asp Ala Trp Trp Glu Lys
225                 230                 235                 240

Val Glu Lys Leu Glu Asp Leu Leu Glu Thr Thr Ala Asn Gln Val Glu
                245                 250                 255

His Ala Ala Val Ile Leu Asp His Asn His Asp Leu Gln Asp Arg Leu
            260                 265                 270

Asp Asn Leu Glu Ala Ser Leu Gln Ala Ala Asn Ile Ser Lys Phe Ser
        275                 280                 285

Cys Ser Leu Val Asp Leu Leu Gln Gln Lys Val Lys Leu Val Glu Asp
    290                 295                 300

Arg Phe Gln Ala Cys Asn Ser Glu Met His Ser Gln Ile Glu Leu Tyr

```
            305                 310                 315                 320
        Glu His Ser Ile Val Glu Phe His Asp Thr Leu Ser Lys Leu Ile Glu
                        325                 330                 335

Glu Ser Glu Lys Arg Ser Leu Glu Asn Phe Thr Gly Asn Met Pro Ser
                        340                 345                 350

Glu Leu Trp Ser Lys Ile Ser Leu Leu Ile Asp Gly Trp Leu Leu Glu
                        355                 360                 365

Lys Lys Ile Ser Tyr Asn Asp Ala Ser Met Leu Arg Glu Met Val Gln
                        370                 375                 380

Lys Arg Asp Ser Arg Leu Arg Glu Ala Tyr Leu Ser Tyr Arg Gly Thr
        385                 390                 395                 400

Glu Asn Arg Glu Val Met Asp Asn Leu Leu Lys Met Ala Leu Pro Gly
                        405                 410                 415

Thr Ser Ser Gly Leu His Ile Ala His Ile Ala Ala Glu Met Ala Pro
                        420                 425                 430

Val Ala Lys Val Gly Gly Leu Ala Asp Val Ile Ser Gly Leu Gly Lys
                        435                 440                 445

Ala Leu Gln Lys Lys Gly His Leu Val Glu Ile Ile Leu Pro Lys Tyr
                        450                 455                 460

Asp Cys Met Gln Val Asp Gln Val Ser Asn Leu Lys Val Leu Asp Val
        465                 470                 475                 480

Leu Val Gln Ser Tyr Phe Glu Gly Asn Met Phe Asn Asn Lys Ile Trp
                        485                 490                 495

Thr Gly Thr Val Glu Gly Leu Pro Val Tyr Phe Ile Glu Pro Gln His
                        500                 505                 510

Pro Ala Met Phe Phe Ser Arg Ala Gln Tyr Tyr Gly Glu His Asp Asp
                        515                 520                 525

Phe Lys Arg Phe Ser Tyr Phe Ser Arg Ala Ala Leu Glu Leu Leu Tyr
                        530                 535                 540

Gln Ser Gly Lys Lys Val Asp Ile Ile His Cys His Asp Trp Gln Thr
        545                 550                 555                 560

Ala Phe Val Ala Pro Leu Tyr Trp Asp Val Tyr Ala Asn Leu Gly Phe
                        565                 570                 575

Asn Ser Ala Arg Ile Cys Phe Thr Cys His Asn Phe Glu Tyr Gln Gly
                        580                 585                 590

Thr Ala Pro Ala Arg Asp Leu Ala Trp Cys Gly Leu Asp Val Glu His
                        595                 600                 605

Leu Asp Arg Pro Asp Arg Met Arg Asp Asn Ser His Gly Arg Ile Asn
                        610                 615                 620

Ala Val Lys Gly Ala Val Val Tyr Ser Asn Ile Val Thr Thr Val Ser
        625                 630                 635                 640

Pro Thr Tyr Ala Leu Glu Val Arg Ser Glu Gly Gly Arg Gly Leu Gln
                        645                 650                 655

Asp Thr Leu Lys Val His Ser Arg Lys Phe Leu Gly Ile Leu Asn Gly
                        660                 665                 670

Ile Asp Thr Asp Thr Trp Asn Pro Cys Thr Asp Arg Tyr Leu Lys Val
                        675                 680                 685

Gln Tyr Asn Ala Lys Asp Leu Gln Gly Lys Ala Ala Asn Lys Ala Ala
                        690                 695                 700
```

-continued

```
Leu Arg Glu Gln Leu Asn Leu Ala Ser Ala Tyr Pro Ser Gln Pro Leu
705                 710                 715                 720

Val Gly Cys Ile Thr Arg Leu Val Ala Gln Lys Gly Val His Leu Ile
                725                 730                 735

Arg His Ala Ile Tyr Lys Thr Ala Glu Leu Gly Gly Gln Phe Val Leu
                740                 745                 750

Leu Gly Ser Ser Pro Val Pro Glu Ile Gln Arg Glu Phe Glu Gly Ile
            755                 760                 765

Ala Asp His Phe Gln Asn Asn Asn Ile Arg Leu Ile Leu Lys Tyr
        770                 775                 780

Asp Asp Ala Leu Ser His Cys Ile Tyr Ala Ala Ser Asp Met Phe Ile
785                 790                 795                 800

Val Pro Ser Ile Phe Glu Pro Cys Gly Leu Thr Gln Met Ile Ala Met
                805                 810                 815

Arg Tyr Gly Ser Val Pro Ile Val Arg Lys Thr Gly Gly Leu Asn Asp
            820                 825                 830

Ser Val Phe Asp Phe Asp Glu Thr Ile Pro Met Glu Val Arg Asn
        835                 840                 845

Gly Phe Thr Phe Val Lys Ala Asp Glu Gln Gly Leu Ser Ser Ala Met
    850                 855                 860

Glu Arg Ala Phe Asn Cys Tyr Thr Arg Lys Pro Glu Val Trp Lys Gln
865                 870                 875                 880

Leu Val Gln Lys Asp Met Thr Ile Asp Phe Ser Trp Asp Thr Ser Ala
            885                 890                 895

Ser Gln Tyr Glu Asp Ile Tyr Gln Lys Ala Val Ala Arg Ala Arg Ala
            900                 905                 910

Val Ala
```

PRODUCTION OF HIGH QUALITY DURUM WHEAT HAVING INCREASED AMYLOSE CONTENT

CROSS-REFERENCE TO RELATED APPLICATIONS

The application claims the benefit of, and is a National Stage Entry of, International Patent Application No. PCT/US2013/066373, filed on Oct. 23, 2013, which claims priority to U.S. provisional application No. 61/736,136 filed on Dec. 12, 2012, and U.S. provisional application No. 61/717,357 filed on Oct. 23, 2012, all of which are hereby incorporated by reference in their entireties for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: MONT_135_01 WO_Seq_List.txt, date recorded: Oct. 10, 2013; file size: 136 kilobytes).

TECHNICAL FIELD

The invention generally relates to improving the end product quality characteristics of durum wheat. More specifically, the present invention relates to compositions and methods for improving one or more end product quality characteristics of wheat by modifying one or more starch synthesis genes.

BACKGROUND

Starch makes up approximately 70% of the dry weight of cereal grains and is composed of two forms of glucose polymers, straight chained amylose with α-1,4 linkages and branched amylopectin with α-1,4 linkages and α-1,6 branch points. In bread wheat, amylose accounts for approximately 25% of the starch with amylopectin the other 75% (reviewed in Tetlow 2006). The synthesis of starch granules is an intricate process that involves several enzymes which associate in complexes (Tetlow et al. 2008; Tetlow et al. 2004b). In bread wheat, the "waxy" proteins (granule bound starch synthase I) encoded by the genes Wx-A1a, Wx-B1a, and Wx-D1a are solely responsible for amylose synthesis after the production of ADP-glucose by ADP-glucose pyrophosphorylase (AGPase) (Denyer et al. 1995; Miura et al. 1994; Yamamori et al. 1994). In contrast, amylopectin synthesis involves a host of enzymes such as AGPase, starch synthases (SS) I, II, III, IV, starch branching enzymes (SBE) I and II, and starch de-branching enzymes (Tetlow et al. 2004a).

The majority of durum wheat is used for pasta and pasta products, but there is interest in investigating durum wheat for noodle production. There are several reasons for interest in durum noodle production. First, it would provide an additional market for durum wheat grain. Durum wheat is lower than bread wheat in polyphenol oxidase, an enzyme causing noodles to turn gray or brown with time. Finally, the high level of carotenoids present in durum wheat could produce enhanced yellow color for alkaline noodles. The proportion of amylose to amylopectin is an important factor in determining end product properties in durum wheat. Much attention has been devoted to determining the impacts of reduced amylose on Asian noodle quality in bread wheat. Information is lacking on the impacts of small increases in amylose on end product quality in durum wheat. Therefore, there is a great need in compositions and methods of modifying amylose in durum wheat. The present invention provides compositions and methods for producing improved durum wheat plants through conventional plant breeding and/or molecular methodologies.

SUMMARY OF INVENTION

The present invention provides for high amylose durum wheat grain. In some embodiments, the grain is produced from a durum wheat plant of the present invention. In some embodiments, the grain is produced from a durum wheat comprising one or more mutations of one or more starch synthesis genes. In some embodiments, the grain is produced from a durum wheat comprising one or more mutations of a durum starch granule protein-B1 (SGP-B1) gene. In some embodiments, the present invention is a high amylose grain produced from a durum wheat plant comprising one or more mutations of a durum starch granule protein-B1 (SGP-B1) gene of a wild type durum wheat plant, wherein the amylose content in said high amylose grain is increased when compared to grain of a wild type durum wheat plant grown at the same time under similar field conditions. In some embodiments, the wheat grain is produced from a durum wheat comprising one or more mutations of a durum starch granule protein-B1 (SGP-B1) gene, and one or more mutations of a durum starch granule protein-A1 (SGP-A1) gene. In some embodiments, the proportion of amylose content in the starch of the grain is at least 40% as measured by differential scanning calorimetry analysis. In other embodiments the amylose content of the starch grain is at least 50%. In some embodiments, the amylose content in the starch of said high amylose grain is increased when compared to the starch of a grain of an appropriate durum wheat check variety grown under similar field conditions. In some embodiments, the durum wheat check variety is grown at the same time as the high amylose durum wheat plant.

In some embodiments, the one or more mutations are selected from a group consisting of a mutation of a starch granule protein-A1 (SGP-A1) allele of a wild type durum wheat plant and/or a mutation of a starch granule protein-B1 (SGP-B1) allele of a wild type durum wheat plant. In some embodiments, the one or more mutations of the high amylose grain comprise a deletion in the first exon of the SGP-A1 gene. In some embodiments, the deletion is at nucleotide position 145-174 of the SGP-A1 gene. In some embodiments, the one or more mutations of the high amylose grain comprise a nucleotide substitution at nucleotide position 979 and/or position 1864 of the SGP-B1 gene. In some embodiments, the one or more genetic mutations comprise null mutations for at least one SGP-A1 gene and/or at least one SGP-B1 gene. In some embodiments, the SGP-B1 mutation leads to an amino acid substitution from aspartic acid to asparagines at amino acid position 327 of SGP-B1, and/or an amino acid substitution from aspartic acid to asparagines at amino acid position 622 of SGP-B1. In some embodiments, the mutation of the SGP-A1 allele or the SGP-B1 allele is caused by artificial mutagenesis or natural mutation. In some embodiments, the mutation is caused by nucleotide substitution, insertion, deletion, and/or genome re-arrangement.

The present invention also discloses the plant cells of high amylose wheat. In some embodiments, the plant cells include cells from any plant part such as plant protoplasts, plant cell tissue cultures from which wheat plants can be regenerated, plant calli, embryos, pollen, grain, ovules, fruit, flowers, leaves, seeds, roots, root tips and the like.

Other embodiments of the present invention include flour based products from durum wheat grain produced from a durum wheat comprising one or more mutations of a durum starch granule protein-B1 (SGP-B1) gene, and one or more mutations of a durum starch granule protein-A1 (SGP-A1) gene. In some embodiments, the high amylose grain can be used to produce flour based products. In some embodiments, milled products produced from the high amylose grain are flour, starch, semolina, among others. In some embodiments, flour based products produced from the high amylose grain are pasta, and noodles among others. The present invention teaches flour based products produced from the high amylose grain. In some embodiments, the invention teaches flour produced from the high amylose grain. In other embodiments the flour based product produced by the high amylose grain is dried pasta. In some embodiments, the flour based product has a protein content of at least 17%. In other embodiments the flour based product has a protein content of at least 20%. In some embodiments, the flour based product has a dietary fiber content of at least 3%. In other embodiments the flour based product has a dietary fiber content of at least 7%. In some embodiments, the flour based product has a resistant starch content of at least 2%. In other embodiments the flour based product has a resistant starch content of at least 3%. In other embodiments the protein, resistant starch and dietary fiber contents of the flour based product are increased when compared to a flour based product from an appropriate durum wheat check line grown under similar field conditions. In some embodiments, of the present invention, when the comparison is to an appropriate durum wheat check line grown under similar field conditions, the wheat lines of the present invention and then check lines are grown at the same time and/or location. For example, in some embodiments, the flour based product has an increased protein content that is at least 10% higher than a flour based product produced from the grain of an appropriate durum wheat check variety grown under similar field conditions. In other embodiments the flour based product has an increased protein content that is at least 20% higher than a flour based product produced from the grain of an appropriate durum wheat check variety grown under similar field conditions. In other embodiments the flour based product has an increased protein content that is at least 30% higher than a flour based product produced from the grain of an appropriate durum wheat check variety grown under similar field conditions. In some embodiments, the flour based product has an increased dietary fiber content that is at least 50% higher than a flour based product produced from the grain of an appropriate durum wheat check variety grown under similar field conditions. In other embodiments the flour based product has an increased dietary fiber content that is at least 100% higher than a flour based product produced from the grain of an appropriate durum wheat check variety grown under similar field conditions. In other embodiments the flour based product has an increased dietary fiber content that is at least 200% higher than a flour based product produced from the grain of an appropriate durum wheat check variety grown under similar field conditions. In some embodiments, the flour based product has an increased resistant starch content that is at least 50% higher than a flour based product produced from the grain of an appropriate durum wheat check variety grown under similar field conditions. In other embodiments the flour based product has an increased resistant starch content that is at least 100% higher than a flour based product produced from the grain of an appropriate durum wheat check variety grown under similar field conditions. In other embodiments the flour based product has an increased resistant starch content that is at least 200% higher than a flour based product produced from the grain of an appropriate durum wheat check variety grown under similar field conditions. In some embodiments, the flour based product has an increased amylose content that is at least 12% higher than a flour based product produced from the grain of an appropriate durum wheat check variety grown under similar field conditions. In other embodiments the flour based product has an increased amylose content that is at least 25% higher than a flour based product produced from the grain of an appropriate durum wheat check variety grown under similar field conditions. In other embodiments the flour based product has an increased amylose content that is at least 40% higher than a flour based product produced from the grain of an appropriate durum wheat check variety grown under similar field conditions. In some embodiments, the flour based product is dried pasta wherein the pasta has improved firmness after cooking compared to pasta produced from the grain of an appropriate durum wheat check variety grown under similar field conditions.

In some embodiments, the high amylose grain has a flour swelling power (FSP) of less than 8.4. In other embodiments the high amylose grain has an FSP of less than 7.5.

In some embodiments, the proportion of dietary fiber, resistant starch, and protein content that is increased in said high amylose grain is increased when compared to the grain of an appropriate durum wheat check variety grown under similar field conditions. In some embodiments, the amylose content of the starch made from the high amylose grain is at least 12% higher than the amylose content of the starch made from the grain of an appropriate wheat check variety grown under similar field conditions. In other embodiments, the amylose content of the starch made from the high amylose grain is at least 25% higher than the amylose content of the starch made from the grain of an appropriate wheat check variety grown under similar field conditions. In other embodiments, the amylose content of the starch made from the high amylose grain is at least 40% higher than the amylose content of the starch made from the grain of an appropriate wheat check variety grown under similar field conditions. In some embodiments, the appropriate durum wheat check variety is grown at the same time and/or location.

In some embodiments, the starch of the high amylose grain has altered gelatinization properties when compared to starch from the grain of an appropriate durum wheat check variety grown under similar field conditions.

In some embodiments, the pasta or noodles made from the high amylose grain have reduced glycemic index compared to pasta or noodles produced from the grain of an appropriate durum wheat check variety grown under similar field conditions.

In some embodiments, the pasta or noodles made from the high amylose grain have increased firmness compared to pasta or noodles made from grain of the appropriate durum wheat check variety grown under similar field conditions.

In some embodiments, the pasta or noodles made from the high amylose grain have increased tolerance to overcooking compared to pasta or noodles made from grain of the appropriate durum wheat check variety grown under similar field conditions.

In some embodiments, the pasta or noodles made from the high amylose grain have increased protein content compared to pasta or noodles made from grain of the appropriate durum wheat check variety grown under similar field conditions.

Pasta produced from the mutant grain also has increased proportion of dietary fiber, resistant starch and/or protein content when compared to pasta made from the grain of the wild type durum wheat plant.

In some embodiments, the grain has increased amylose content compared to the grain of the wild type durum wheat plant.

In some embodiments, the grain has increased dietary fiber and increased amylose content when compared to the grain of the wild type durum wheat plant.

In some embodiments, the grain has increased protein content and increased amylose content when compared to the grain of the wild type durum wheat plant.

In some embodiments, the grain has increased dietary fiber and decreased endosperm to bran ratio and/or reduced milling yield when compared to the grain of the wild type durum wheat plant.

In some embodiments, the grain has increased dietary fiber and increased ash when compared to the grain of the wild type durum wheat plant.

In some embodiments, the grain has increased protein and reduced starch content when compared to the grain of the wild type durum wheat plant.

In some embodiments, the mutant durum wheat starch has an increased amylose content when compared to the wild type durum wheat starch. In some embodiments, the amylose content of the mutant durum wheat is about 38% to about 50%.

In some embodiments, the starch of the present invention has an overall decrease in the amount of B-type starch granules when compared to starch the of an appropriate wheat check variety grown under similar field conditions.

In some embodiments, the starch of the present invention has an altered gelatinization property when compared to the wild type durum wheat starch.

In some embodiments, the grain produced imparts increased firmness to food, such as pasta or noodles produced from the durum wheat plant when compared to food, such as pasta or noodles produced from the wild type durum wheat plant.

In some embodiments, the grain of the present invention imparts reduced glycemic index to pasta or noodles produced from the durum wheat plant when compared to pasta or noodles produced from the wild type durum wheat plant.

In some embodiments, the grain of the present invention has increased tolerance to overcooking when compared to the wild type durum wheat starch.

The present invention also provides flour produced from the grain of the present invention.

The present invention also provides starch produced from the grain of the present invention.

The present invention also provides methods for producing a high amylose durum wheat plant. In some embodiments, the methods comprise performing mutagenesis on durum wheat plant that comprises a SGP-A1 mutation and/or a SGP-B1 mutation. In some embodiments, the durum wheat plant comprises a SGP-A1 with a 29 bp deletion in the first exon. In some embodiments, the durum wheat plant comprises a SGP-B1 with amino acid substitution from at amino acid position 327 of SGP-B1, e.g., from aspartic acid to asparagines, and/or an amino acid substitution at amino acid position 622 of SGP-B1, e.g., from aspartic acid to asparagines. The methods produce a durum wheat plant with an elevated amylose content when compared to a wild type durum wheat plant.

The present invention also provides methods for producing durum wheat with one or more mutations of a durum starch granule protein (SGP-B1). In some embodiments, the invention provides methods for producing durum wheat with one or more mutations of a durum starch granule protein (SGP-B1), and one or more mutations of a durum starch granule protein-A1 (SGP-A1) gene. In some embodiments, the method comprises mutagenizing a durum wheat grain containing one or more mutations of a durum starch granule protein-A1 (SGP-A1) gene to form a mutagenized population of grain; growing one or more durum wheat plants from said mutagenized durum wheat grain; screening the resulting plants to identify durum wheat plants with a durum SGP-B1 mutant gene; and, selecting one or more durum wheat plants containing the durum SGP-B1 mutant gene. In other embodiments the method comprises mutagenizing a durum wheat grain containing one or more mutations of a durum starch granule protein-B1 (SGP-B1) gene to form a mutagenized population of grain; growing one or more durum wheat plants from said mutagenized durum wheat grain; screening the resulting plants to identify durum wheat plants with a durum SGP-A1 mutant gene; and, selecting one or more durum wheat plants containing the durum SGP-A1 mutant gene. In some embodiments, the resulting durum wheat plant comprises one or more mutations of a durum starch granule protein-B1 (SGP-B1) gene, and one or more mutations of a durum starch granule protein-A1 (SGP-A1) gene, and wherein said plant produces high amylose grain. In other embodiments the method for producing the durum wheat plant with one or more mutations of a durum starch granule protein (SGP-B1), and one or more mutations of a durum starch granule protein-A1 (SGP-A1) gene comprises crossing a durum wheat plant containing one or more mutations on a durum SGP-A1 gene with a second durum wheat plant containing one or more mutations on a durum SGP-B1 gene; harvesting the resulting seed; and, growing the harvested seed. In some embodiments, the resulting durum wheat plant comprises one or more mutations of a durum starch granule protein-B1 (SGP-B1) gene, and one or more mutations of a durum starch granule protein-A1 (SGP-A1) gene, and wherein said plant produces high amylose grain.

The present invention also provides methods for culturing plant tissue. In some embodiments, the method of culturing and regenerating plant tissue comprises culturing at least part of the high amylose durum wheat plant in conditions conducive to plant regeneration, thereby regenerating said plant. The present invention also provides methods of producing hybrid seeds, the method comprising crossing the high amylose durum wheat with another plant, and harvesting the resultant seed. The present invention also provides methods of breeding durum wheat plants with high amylose grain comprising making a cross between a first high amylose durum plant with a second plant to produce a F1 plant; backcrossing the F1 plant to the second plant; and repeating the backcrossing step one or more times to generate a near isogenic or isogenic line. In some embodiments, the resulting plant has the SGP-A1 and SGP-B1 mutations integrated into the genome of the second plant and the near isogenic or isogenic line derived from the second plant with the SGP-A1 and/or SBP-B1 mutations.

The present invention also provides methods for increasing firmness in a food product produced from durum wheat grain. In some embodiments, the food product is noodle or pasta. In some embodiments, the methods comprise producing the noodle or pasta from a durum wheat plant wherein said durum wheat plant includes at least one mutation in the SGP-1 protein. The durum wheat plant produces grain with an elevated amylose content when compared to a wild type durum wheat plant. In some embodiments, the food product produced from such durum wheat plant is more resistant to overcooking compared to food product produced from grain of a wild-type durum wheat plant. In some embodiments, at least one mutation is selected from a group consisting of a mutation of a starch granule protein-A1 (SGP-A1) allele and a mutation of a starch granule protein-B1 (SGP-B1) allele.

SEQUENCES

Figure 1:
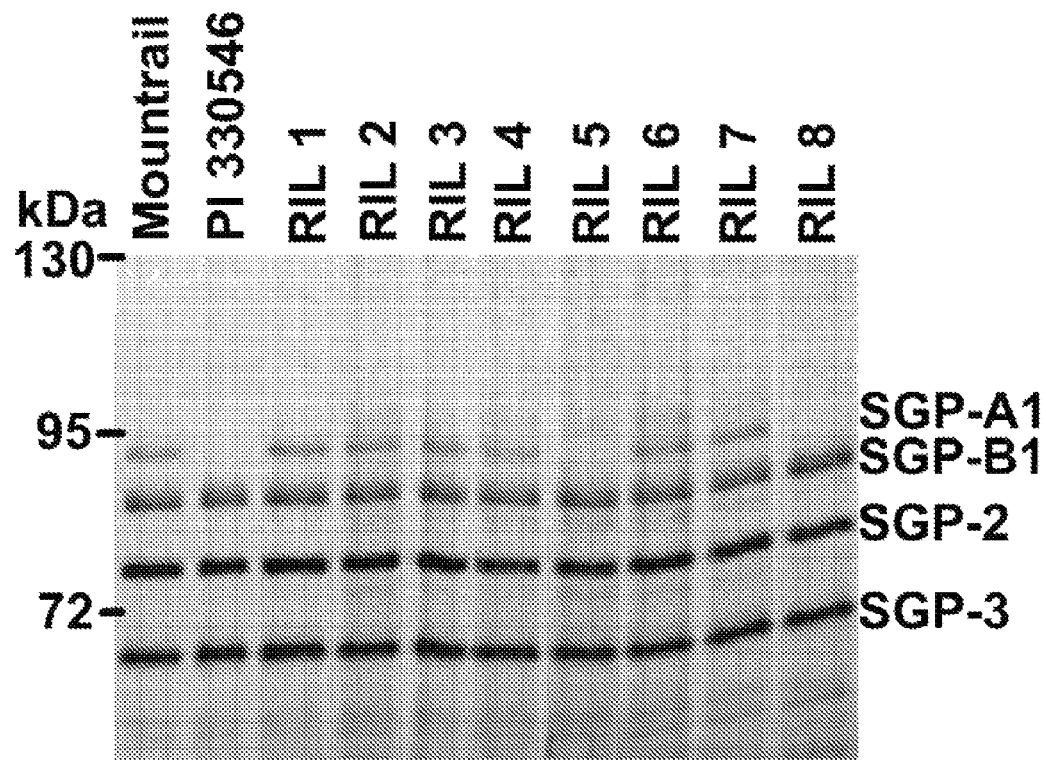
FIG. 1 depicts SDS-PAGE analysis of starch granule proteins from Mountrail (SSIIa-Aa) and PI 330546 (SSIIa-Ab) and segregating recombinant inbred lines from their cross.

Sequence listings for SEQ ID No: 1-SEQ ID No: 24 are part of this application and are incorporated by reference herein. Sequence listings are provided at the end of this document.

DETAILED DESCRIPTION

All publications, patents and patent applications, including any drawings and appendices, and all nucleic acid sequences and polypeptide sequences identified by GenBank Accession numbers, herein are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

Definitions

As used herein, the verb "comprise" as is used in this description and in the claims and its conjugations are used in its non-limiting sense to mean that items following the word are included, but items not specifically mentioned are not excluded.

The invention provides compositions and methods for improving the end product quality characteristics of plants. As used herein, the term "plant" refers to wheat (e.g., bread wheat or durum wheat), unless specified otherwise.

As used herein, the term "plant" also includes the whole plant or any parts or derivatives thereof, such as plant cells, plant protoplasts, plant cell tissue cultures from which wheat plants can be regenerated, plant calli, embryos, pollen, grain, ovules, fruit, flowers, leaves, seeds, roots, root tips and the like.

As used herein, the term "appropriate durum wheat check", is meant to represent a durum wheat plant which provides a basis for evaluation of the experimental plants of the present invention. An appropriate check is grown under the same environmental conditions, as is the experimental line, and is of approximately the same maturity as the experimental line. The term "appropriate durum wheat check" may actually reflect multiple appropriate varieties chosen to represent control lines for the modification or factor being tested in the experimental line. In some embodiments, the appropriate durum wheat check variety can be a wild type durum wheat variety without the experimental mutation. In some embodiments, durum wheat check lines can be 'Mountrail', 'Divide', 'Strongfield', or 'Alazda' wild type varieties.

The invention provides plant parts. As used herein, the term "plant part" refers to any part of a plant including but not limited to the shoot, root, stem, seeds, stipules, leaves, petals, flowers, ovules, bracts, branches, petioles, internodes, bark, pubescence, tillers, rhizomes, fronds, blades, pollen, stamen, plant cells, and the like.

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements are present, unless the context clearly requires that there is one and only one of the elements.

The invention provides selectable marker. As used herein, the phrase "plant selectable or screenable marker" refers to a genetic marker functional in a plant cell. A selectable marker allows cells containing and expressing that marker to grow under conditions unfavorable to growth of cells not expressing that marker. A screenable marker facilitates identification of cells which express that marker.

The invention provides inbred plants. As used herein, the terms "inbred" and "inbred plant" are used in the context of the present invention. This also includes any single gene conversions of that inbred.

The term "single allele converted plant" as used herein refers to those plants which are developed by a plant breeding technique called backcrossing wherein essentially all of the desired morphological and physiological characteristics of an inbred are recovered in addition to the single allele transferred into the inbred via the backcrossing technique.

The invention provides plant samples. As used herein, the term "sample" includes a sample from a plant, a plant part, a plant cell, or from a transmission vector, or a soil, water or air sample.

The invention provides plant offsprings. As used herein, the term "offspring" refers to any plant resulting as progeny from a vegetative or sexual reproduction from one or more parent plants or descendants thereof. For instance an offspring plant may be obtained by cloning or selfing of a parent plant or by crossing two parent plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

The invention provides methods for crossing a first plant comprising recombinant sequences with a second plant. As used herein, the term "cross", "crossing", "cross pollination" or "cross-breeding" refer to the process by which the pollen of one flower on one plant is applied (artificially or naturally) to the ovule (stigma) of a flower on another plant.

The invention provides plant cultivars. As used herein, the term "cultivar" refers to a variety, strain or race of plant that has been produced by horticultural or agronomic techniques and is not normally found in wild populations.

The invention provides plant genes. As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

The invention provides plant genotypes. As used herein, the term "genotype" refers to the genetic makeup of an individual cell, cell culture, tissue, organism (e.g., a plant), or group of organisms.

In some embodiments, the present invention provides homozygotes of plants. As used herein, the term "hemizygous" refers to a cell, tissue or organism in which a gene is present only once in a genotype, as a gene in a haploid cell or organism, a sex-linked gene in the heterogametic sex, or a gene in a segment of chromosome in a diploid cell or organism where its partner segment has been deleted.

In some embodiments, the present invention provides heterologous nucleic acids. As used herein, the terms "heterologous polynucleotide" or a "heterologous nucleic acid" or an "exogenous DNA segment" refer to a polynucleotide, nucleic acid or DNA segment that originates from a source foreign to the particular host cell, or, if from the same source, is modified from its original form. Thus, a heterologous gene in a host cell includes a gene that is endogenous to the particular host cell, but has been modified. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

In some embodiments, the present invention provides heterologous traits. As used herein, the term "heterologous trait" refers to a phenotype imparted to a transformed host cell or transgenic organism by an exogenous DNA segment, heterologous polynucleotide or heterologous nucleic acid.

In some embodiments, the present invention provides heterozygotes. As used herein, the term "heterozygote" refers to a diploid or polyploid individual cell or plant having different alleles (forms of a given gene) present at least at one locus.

In some embodiments, the present invention provides heterozygous traits. As used herein, the term "heterozygous" refers to the presence of different alleles (forms of a given gene) at a particular gene locus.

In some embodiments, the present invention provides homologs. As used herein, the terms "homolog" or "homologue" refer to a nucleic acid or peptide sequence which has a common origin and functions similarly to a nucleic acid or peptide sequence from another species.

In some embodiments, the present invention provides homozygotes. As used herein, the term "homozygote" refers to an individual cell or plant having the same alleles at one or more or all loci. When the term is used with reference to a specific locus or gene, it means at least that locus or gene has the same alleles.

In some embodiments, the present invention provides homozygous traits. As used herein, the terms "homozygous" or "HOMO" refer to the presence of identical alleles at one or more or all loci in homologous chromosomal segments. When the terms are used with reference to a specific locus or gene, it means at least that locus or gene has the same alleles.

In some embodiments, the present invention provides hybrids. As used herein, the term "hybrid" refers to any individual cell, tissue or plant resulting from a cross between parents that differ in one or more genes.

In some embodiments, the present invention provides mutants. As used herein, the terms "mutant" or "mutation" refer to a gene, cell, or organism with an abnormal genetic constitution that may result in a variant phenotype.

The invention provides open-pollinated populations. As used herein, the terms "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

The invention provides plant ovules and pollens. As used herein when discussing plants, the term "ovule" refers to the female gametophyte, whereas the term "pollen" means the male gametophyte.

The invention provides plant phenotypes. As used herein, the term "phenotype" refers to the observable characters of an individual cell, cell culture, organism (e.g., a plant), or group of organisms which results from the interaction between that individual's genetic makeup (i.e., genotype) and the environment.

The invention provides plant tissue. As used herein, the term "plant tissue" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

The invention provides self-pollination populations. As used herein, the term "self-crossing", "self pollinated" or "self-pollination" means the pollen of one flower on one plant is applied (artificially or naturally) to the ovule (stigma) of the same or a different flower on the same plant.

As used herein, the term "amylose content" refers to the amount of amylose in wheat starch. Amylose is a linear polymer of α-1,4 linked D-glucose with relatively few side chains. Amylose is digested more slowly than amylopectin which while also having linear polymers of α-1,4 linked D-glucose has many α-1,6 D-glucose side chains. Amylose absorbs less water upon heating than amylopectin and is digested more slowly. Amylose content can be measured by colormetric assays involving iodine-potassium iodide assays, by DSC, Con A, or estimated by measuring the water absorbing capacity of flour or starch after heating.

As used herein, the term "starch synthesis genes" refers to any genes that directly or indirectly contribute to, regulate, or affect starch synthesis in a plant. Such genes includes, but are not limited to genes encoding waxy protein (a.k.a., Granule bound starch synthases (GBSS), such as GBSSI, GBSSII). ADP-glucose pyrophosphorylases (AGPases), starch branching enzymes (a.k.a., SBE, such as SBE 1 and SBE II), starch de-branching enzymes (a.k.a., SDBE), and starch synthases I, II, III, and IV.

As used herein, the term "waxy protein", "Granule bound starch synthase", GBSS, or "ADP-glucose:(1→4)-alpha-D-glucan 4-alpha-D-glucosyltransferase" refers to a protein having E.C. number 2.4.1.21, which can catalyze the following reaction:

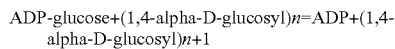

As used herein, the term "ADP-glucose pyrophosphorylase", AGPase, "adenosine diphosphate glucose pyrophosphorylase", or "adenosine-5'-diphosphoglucose pyrophosphorylase" refers to a protein having E.C. number 2.7.7.27, which can catalyze the following reaction:

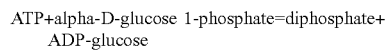

As used herein, the term "starch branching enzyme", SBE, "branching enzyme", BE, "glycogen branching enzyme", "1,4-alpha-glucan branching enzyme", "alpha-1,4-glucan:alpha-1,4-glucan 6-glycosyltransferase" or "(1→4)-alpha-D-glucan:(1→4)-alpha-D-glucan 6-alpha-D-[(1→4)-alpha-D-glucano]-transferase" refers to a protein having E.C. number 2.4.1.18, which can catalyze the following reaction:

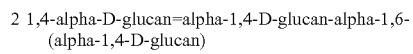

As used herein, the term "starch de-branching enzymes", SDBE, or isoamylase refers to a protein having the E.C. number 2.4.1.1, 2.4.1.25, 3.2.1.68 or 3.2.1.41, which can hydrolyse alpha-1,6 glucosidic bonds in glucans containing both alpha-1,4 and alpha-1,6 linkages.

As used herein, the term starch synthase I, II, III, or IV (SSI or SI, SSII or SII, SSIII or SOOO, and SSIV or SIV), refers to a protein of starch synthase class I, class II, class III, or class IV, respectively. Such as protein that is involved in amylopectin synthesis.

As used herein, the term starch granule protein-1 or SGP-1 refers to a protein belonging to starch synthase class II, contained in wheat starch granules (Yamamori and Endo, 1996).

As used herein, the term wheat refers to any wheat species within the genus of *Triticum*, or the tribe of Triticeae, which includes, but are not limited to, diploid, tetraploid, and hexaploid wheat species.

As used herein, the term "milled product" refers to a product produced from grinding grains (from wheat or other grain producing plants). Non-limiting examples of milled products include: flour, all purpose flour, starch, bread flour, cake flour, self-rising flour, pastry flour, semolina, durum flour, whole wheat flour, stone ground flour, gluten flour, and graham flour among others.

As used herein, the term "flour based product" refers to products made from flour including: pasta, noodles, bread products, cookies, and pastries among others.

As used herein, the term "high amylose grain" refers to a durum wheat grain with starch with high levels of amylose. In some embodiments, the high amylose levels are elevated compared to the amylose content of a wheat grain from a wild type or other appropriate durum wheat check variety grown at the same time under similar field conditions. In other embodiments the amylose levels are high in absolute percentage terms as measured by differential scanning calorimetry analysis.

As used herein, the term diploid wheat refers to wheat species that have two homologous copies of each chromosome, such as Einkorn wheat (*T. monococcum*), having the genome AA.

As used herein, the term tetraploid wheat refers to wheat species that have four homologous copies of each chromosome, such as emmer and durum wheat, which are derived from wild emmer (*T. dicoccoides*). Wild emmer is itself the result of a hybridization between two diploid wild grasses, *T. urartu* and a wild goatgrass such as *Aegilops searsii* or *Ae. speltoides*. The hybridization that formed wild emmer (having genome AABB) occurred in the wild, long before domestication, and was driven by natural selection.

As used herein, the term hexaploid wheat refers to wheat species that have six homologous copies of each chromosome, such as bread wheat. Either domesticated emmer or durum wheat hybridized with another wild diploid grass (*Aegilops tauschii*, having genome DD) to make the hexaploid wheats (having genome AABBDD).

As used herein, SSIIa-Aa refers to both wild type "aa" alleles being present but SSIIa-Ab refers to both "bb" alleles being present. SSIIa and SSIIb would be two different forms of the same enzyme.

As used herein, the term "gelatinization temperature" refers to the temperature at which starch is dissolved in water during heating. Gelatinization temperature is related to amylose content with increased amylose content associated with increased gelatinization temperature.

As used herein, the term "starch retrogradation" refers to the firmness of starch water gels with increased amylose associated with increased starch retrogradation and firmer starch based gels.

As used herein, the term "flour swelling power" or FSP refers to the weight of flour or starch based gel relative to the weight of the original sample after heating in the presence of excess water. Increased amylose is associated with decreased FSP.

As used herein, the term "grain hardness" refers to the pressure required to fracture grains and is related to particle size after milling, milling yield, and some end product quality traits. Increased grain hardness is associated with increased flour particle size, increased starch damage and decreased break flour yield.

As used herein, the term "semolina" refers to the coarse, purified wheat middlings of durum wheat.

As used herein, the term "resistant amylose" refers to amylose which resists digestion and thus serves a purpose in the manufacturing of reduced glycemic index food products.

As used herein, the term "resistant starch" refers to starch that resists digestion and behaves like dietary fiber. Increased amylose is believed to be associated with increased resistant starch.

As used herein, the term "allele" refers to any of several alternative forms of a gene.

As used herein, "starch" refers to starch in its natural or native form as well as also referring to starch modified by physical, chemical, enzymatic and biological processes.

As used herein, "amylose" refers to a starch polymer that is an essentially linear assemblage of D-anhydroglucose units which are linked by alpha 1,6-D-glucosidic bonds.

As used herein, "amylose content" refers to the percentage of the amylose type polymer in relation to other starch polymers such as amylopectin.

As used herein, the term "grain" refers to mature wheat kernels produced by commercial growers for purposes other than growing or reproducing the species.

As used herein, the term "kernel" refers to the wheat caryopsis comprising a mature embryo and endosperm which are products of double fertilization.

As used herein, the term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses effected such that a gene or a combination of genes, in heterozygous (hemizygous) or homozygous condition, imparts a desired trait to the plant.

As used herein, the term "locus" (plural: "loci") refers to any site that has been defined genetically. A locus may be a gene, or part of a gene, or a DNA sequence that has some regulatory role, and may be occupied by the same or different sequences.

The invention provides methods for obtaining plants or plant cells through transformation. As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell.

The invention provides plant and plant cell transformants. As used herein, the term "transformant" refers to a cell, tissue or organism that has undergone transformation. The original transformant is designated as "T0" or "$T_0$." Selfing the T0 produces a first transformed generation designated as "T1" or "$T_1$."

The invention provides plant transgenes. As used herein, the term "transgene" refers to a nucleic acid that is inserted into an organism, host cell or vector in a manner that ensures its function.

The invention provides plant transgenic plants, plant parts, and plant cells. As used herein, the term "transgenic" refers to cells, cell cultures, organisms (e.g., plants), and progeny which have received a foreign or modified gene by one of the various methods of transformation, wherein the foreign or modified gene is from the same or different species than the species of the organism receiving the foreign or modified gene.

The invention provides plant transposition events. As used herein, the term "transposition event" refers to the movement of a transposon from a donor site to a target site.

The invention provides plant varieties. As used herein, the term "variety" refers to a subdivision of a species, consisting of a group of individuals within the species that are distinct in form or function from other similar arrays of individuals.

The invention provides plant vectors, plasmids, or constructs. As used herein, the term "vector", "plasmid", or "construct" refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746).

The invention provides isolated, chimeric, recombinant or synthetic polynucleotide sequences. As used herein, the term "polynucleotide", "polynucleotide sequence", or "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The invention provides isolated, chimeric, recombinant or polypeptide sequences. As used herein, the terms "polypeptide," "peptide," and "protein" are used interchangeably herein to refer to polymers of amino acids of any length. These terms also include proteins that are post-translationally modified through reactions that include glycosylation, acetylation and phosphorylation.

The invention provides homologous and orthologous polynucleotides and polypeptides. As used herein, the term "homologous" or "homologue" or "ortholog" is known in the art and refers to related sequences that share a common ancestor or family member and are determined based on the degree of sequence identity. The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences. These terms describe the relationship between a gene found in one species, subspecies, variety, cultivar or strain and the corresponding or equivalent gene in another species, subspecies, variety, cultivar or strain. For purposes of this invention homologous sequences are compared. "Homologous sequences" or "homologues" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one embodiment, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in *Current Protocols in Molecular Biology* (F. M. Ausubel et al., eds., 1987) Supplement 30, section 7.718, Table 7.71. Some alignment programs are MacVector (Oxford Molecular Ltd. Oxford, U.K.), ALIGN Plus (Scientific and Educational Software, Pennsylvania) and AlignX (Vector NTI, Invitrogen, Carlsbad, Calif.). Another alignment program is Sequencher (Gene Codes, Ann Arbor, Mich.), using default parameters.

The invention provides polynucleotides with nucleotide change when compared to a wild-type reference sequence. As used herein, the term "nucleotide change" refers to, e.g., nucleotide substitution, deletion, and/or insertion, as is well understood in the art. For example, mutations contain alterations that produce silent substitutions, additions, or deletions, but do not alter the properties or activities of the encoded protein or how the proteins are made.

The invention provides polypeptides with protein modification when compared to a wild-type reference sequence. As used herein, the term "protein modification" refers to, e.g., amino acid substitution, amino acid modification, deletion, and/or insertion, as is well understood in the art.

The invention provides polynucleotides and polypeptides derived from wild-type reference sequences. As used herein, the term "derived from" refers to the origin or source, and may include naturally occurring, recombinant, unpurified, or purified molecules, and may also include cells whose origin is a plant or plant part. A nucleic acid or an amino acid derived from an origin or source may have all kinds of nucleotide changes or protein modification as defined elsewhere herein.

The invention provides portions or fragments of the nucleic acid sequences and polypeptide sequences of the present invention. As used herein, the term "at least a portion" or "fragment" of a nucleic acid or polypeptide means a portion having the minimal size characteristics of such sequences, or any larger fragment of the full length molecule, up to and including the full length molecule. For example, a portion of a nucleic acid may be 12 nucleotides, 13 nucleotides, 14 nucleotides, 15 nucleotides, 16 nucleotides, 17 nucleotides, 18 nucleotides, 19 nucleotides, 20 nucleotides, 22 nucleotides, 24 nucleotides, 26 nucleotides, 28 nucleotides, 30 nucleotides, 32 nucleotides, 34 nucleotides, 36 nucleotides, 38 nucleotides, 40 nucleotides, 45 nucleotides, 50 nucleotides, 55 nucleotides, and so on, going up to the full length nucleic acid. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as hybridization probe may be as short as 12 nucleotides; in one embodiment, it is 20 nucleotides. A portion of a polypeptide useful as an epitope may be as short as 4 amino acids. A portion of a polypeptide that performs the function of the full-length polypeptide would generally be longer than 4 amino acids.

The invention provides sequences having high similarity or identity to the nucleic acid sequences and polypeptide sequences of the present invention. As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988).

The invention provides sequences substantially complementary to the nucleic acid sequences of the present invention. As used herein, the term "substantially complementary" means that two nucleic acid sequences have at least about 65%, preferably about 70% or 75%, more preferably about 80% or 85%, even more preferably 90% or 95%, and most preferably about 98% or 99%, sequence complementarities to each other. This means that primers and probes must exhibit sufficient complementarity to their template and target nucleic acid, respectively, to hybridize under stringent conditions. Therefore, the primer and probe sequences need not reflect the exact complementary sequence of the binding region on the template and degenerate primers can be used. For example, a non-complementary nucleotide fragment may be attached to the 5'-end of the primer, with the remainder of the primer sequence being complementary to the strand. Alternatively, non-complementary bases or longer sequences can be interspersed into the primer, provided that the primer has sufficient complementarity with the sequence of one of the strands to be amplified to hybridize therewith, and to thereby form a duplex structure which can be extended by polymerizing means. The non-complementary nucleotide sequences of the primers may include restriction enzyme sites. Appending a restriction enzyme site to the end(s) of the target sequence would be particularly helpful for cloning of the target sequence. A substantially complementary primer sequence is one that has sufficient sequence complementarity to the amplification template to result in primer binding and second-strand synthesis. The skilled person is familiar with the requirements of primers to have sufficient sequence complementarity to the amplification template.

The invention provides biologically active variants or functional variants of the nucleic acid sequences and polypeptide sequences of the present invention. As used herein, the phrase "a biologically active variant" or "functional variant" with respect to a protein refers to an amino acid sequence that is altered by one or more amino acids with respect to a reference sequence, while still maintains substantial biological activity of the reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variations can also include amino acid deletion or insertion, or both. Guidance in determining which amino acid residues can be substituted, inserted, or deleted without eliminating biological or immunological activity can be found using computer programs well known in the art, for example, DNASTAR software. For polynucleotides, a variant comprises a polynucleotide having deletions (i.e., truncations) at the 5' and/or 3' end; deletion and/or addition of one or more nucleotides at one or more internal sites in the reference polynucleotide; and/or substitution of one or more nucleotides at one or more sites in the reference polynucleotide. As used herein, a "reference" polynucleotide comprises a nucleotide sequence produced by the methods disclosed herein. Variant polynucleotides also include synthetically derived polynucleotides, such as those generated, for example, by using site directed mutagenesis but which still comprise genetic regulatory element activity. Generally, variants of a particular polynucleotide or nucleic acid molecule of the invention will have at least about 60%, 65%, 70%, 75%, 80%, 85%, 90%, 91%, 91.5%, 92%, 92.5%, 93%, 93.5%, 94%, 94.5%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or more sequence identity to that particular polynucleotide as determined by sequence alignment programs and parameters as described elsewhere herein.

Variant polynucleotides also encompass sequences derived from a mutagenic and recombinogenic procedure such as DNA shuffling. Strategies for such DNA shuffling are known in the art. See, for example, Stemmer (1994) *PNAS* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *PNAS* 94:4504-4509; Crameri et al. (1998) *Nature* 391:288-291; and U.S. Pat. Nos. 5,605,793 and 5,837,458. For PCR amplifications of the polynucleotides disclosed herein, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2nd ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

The invention provides primers that are derived from the nucleic acid sequences and polypeptide sequences of the present invention. The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

The invention provides polynucleotide sequences that can hybridize with the nucleic acid sequences of the present invention. The terms "stringency" or "stringent hybridization conditions" refer to hybridization conditions that affect the stability of hybrids, e.g., temperature, salt concentration, pH, formamide concentration and the like. These conditions are empirically optimized to maximize specific binding and minimize non-specific binding of primer or probe to its target nucleic acid sequence. The terms as used include reference to conditions under which a probe or primer will hybridize to its target sequence, to a detectably greater degree than other sequences (e.g. at least 2-fold over background). Stringent conditions are sequence dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridizes to a perfectly matched probe or primer. Typically, stringent conditions will be those in which the salt concentration is less than about 1.0 M Na$^+$ ion, typically about 0.01 to 1.0 M Na+ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1M NaCl, 1% SDS at 37° C., and a wash in 0.1×SSC at 60° C. Hybridization procedures are well known in the art and are described by e.g. Ausubel et al., 1998 and Sambrook et al., 2001.

The invention provides coding sequences. As used herein, "coding sequence" refers to a DNA sequence that codes for a specific amino acid sequence.

The invention provides regulatory sequences. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence.

The invention provides promoter sequences. As used herein, "promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity.

In some embodiments, the invention provides plant promoters. As used herein, a "plant promoter" is a promoter capable of initiating transcription in plant cells whether or not its origin is a plant cell, e.g. it is well known that Agrobacterium promoters are functional in plant cells. Thus, plant promoters include promoter DNA obtained from plants, plant viruses and bacteria such as Agrobacterium and Bradyrhizobium bacteria. A plant promoter can be a constitutive promoter or a non-constitutive promoter.

The invention provides recombinant genes comprising 3' non-coding sequences or 3' untranslated regions. As used herein, the "3' non-coding sequences" or "3' untranslated regions" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. (1989) Plant Cell 1:671-680.

The invention provides RNA transcripts. As used herein, "RNA transcript" refers to the product resulting from RNA polymerase-catalyzed transcription of a DNA sequence. When the RNA transcript is a perfect complementary copy of the DNA sequence, it is referred to as the primary transcript. An RNA transcript is referred to as the mature RNA when it is an RNA sequence derived from post-transcriptional processing of the primary transcript. "Messenger RNA (mRNA)" refers to the RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The invention provides recombinant genes in which a gene of interest is operably linked to a promoter sequence. As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

The invention provides recombinant expression cassettes and recombinant constructs. As used herein, the term "recombinant" refers to an artificial combination of two otherwise separated segments of sequence, e.g., by chemical synthesis or by the manipulation of isolated segments of nucleic acids by genetic engineering techniques. As used herein, the phrases "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating.

In yet another embodiment, the present invention provides a tissue culture of regenerable cells of a durum wheat plant obtained from the durum wheat lines of the present invention, wherein the tissue regenerates plants having all or substantially all of the morphological and physiological characteristics of the durum wheat plants provided by the present invention. In one such embodiment, the tissue culture is derived from a plant part selected from the group consisting of leaves, roots, root tips, root hairs, anthers, pistils, stamens, pollen, ovules, flowers, seeds, embryos, stems, buds, cotyledons, hypocotyls, cells and protoplasts. In another such embodiment, the present invention includes a wheat plant regenerated from the above described tissue culture.

This invention provides the cells, cell culture, tissues, tissue culture, seed, whole plant and plant parts of durum wheat germplasm designated 'DHA175' or derived from 'DHA-175' or any of its offspring.

This invention provides the cells, cell culture, tissues, tissue culture, seed, whole plant and plant parts of durum wheat germplasm designated 'DHA55' or derived from DHA-55 or any of its offspring. For example methods of wheat tissue culture please see (Altpeter et al., 1996; Smidansky et al., 2002)

Wheat

Wheat is a plant species belonging to the genus of *Triticum*. Non-limiting examples of wheat species include, *T. aestivum* (a.k.a., common wheat, or bread wheat, hexaploid), *T. aethiopicum, T. araraticum, T. boeoticum, T. carthlicum, T. compactum, T. dicoccoides, T. dicoccum* (a.k.a., emmer wheat, tetraploid), *T. durum* (a.k.a., durum wheat, tetraploid), *T. ispahanicum, T. karamyschevii, T. macha, T. militinae, T. monococcum* (Einkorn wheat, diploid), *T. polonicum, T. spelta* (a.k.a. spelt, hexaploid), *T. sphaerococcum, T. timopheevii, T. turanicum, T. turgidum, T. urartu, T. vavilovii, T. zhukovskyi*, and any hybridization thereof.

Some wheat species are diploid, with two sets of chromosomes, but many are stable polyploids, with four sets (tetraploid) or six sets (hexaploid) of chromosomes.

Einkorn wheat (*T. monococcum*) is diploid (AA, two complements of seven chromosomes, 2n=14). Most tetraploid wheats (e.g. emmer and durum wheat) are derived from wild emmer, *T. dicoccoides*. Wild emmer is itself the result of a hybridization between two diploid wild grasses, *T. urartu* and a wild goatgrass such as *Aegilops searsii* or *Aegilops speltoides*. The hybridization that formed wild emmer (AABB) occurred in the wild, long before domestication, and was driven by natural selection (Hancock, James F. (2004) Plant Evolution and the Origin of Crop Species. CABI Publishing. ISBN 0-85199-685-X). Hexaploid wheats (AABBDD) evolved in farmers' fields. Either domesticated emmer or durum wheat hybridized with yet another wild diploid grass (*Aegilops tauschii*) to make the hexaploid wheats, spelt wheat and bread wheat. These have three sets of paired chromosomes.

Therefore, in hexaploid wheat, most genes exist in triplicated homoeologous sets, one from each genome (i.e., the A genome, the B genome, or the D genome), while in tetraploid wheat, most genes exist in doubled homologous sets, one from each genome (i.e., the A genome or the B genome). Due to random mutations that occur along genomes, the alleles isolated from different genomes are not necessarily identical.

The presence of certain alleles of wheat genes is important for crop phenotypes. Some alleles encode functional polypeptides with equal or substantially equal activity of a reference allele. Some alleles encode polypeptides having increased activity when compared to a reference allele. Some alleles are in disrupted versions which do not encode functional polypeptides, or only encode polypeptides having less activity compared to a reference allele. Each of the different alleles can be utilized depending on the specific goals of a breeding program.

Wheat Starch Synthesis Genes

Starch is the major reserve carbohydrate in plants. It is present in practically every type of tissue: leaf, fruit, root, shoot, stem, pollen, and seed. In cereal grains, starch is the primary source of stored energy. The amount of starch contained in cereal grains varies depending on species, and developmental stages.

Two types of starch granules are found in the wheat endosperm. The large (A-type) starch granules of wheat are disk-like or lenticular in shape, with an average diameter of 10-35 μm, whereas the small (B-type) starch granules are roughly spherical or polygonal in shape, ranging from 1 to 10 μm in diameter.

Bread wheat (*Triticum aestivum* L.) starch normally consists of roughly 25% amylose and 75% amylopectin (reviewed in Hannah and James, 2008). Amylose is a linear chain of glucose molecules linked by α-1,4 linkages. Amylopectin consists of glucose residues linked by α-1,4 linkages with α-1,6 branch points.

Starch synthesis is catalyzed by starch synthases. Amylose and amylopectin are synthesized by two pathways having a common substrate, ADP-glucose. AGPase catalyzes the initial step in starch synthesis in plants. Waxy proteins granule bound starch synthase I (GBSSI) is encoded by Wx genes which are responsible for amylose synthesis.

Soluble starch synthase, such as starch synthase I (SSI or SI), II (SSII or SII), and III (SSIII or SII), starch branching enzymes (e.g., SBEI, SBEIIa and SBEIIb), and starch debranching enzymes of isoamylase- and limit dextrinase-type (ISA and LD) are believed to play key roles in amylopectin synthesis.

SSI of wheat is partitioned between the granule and the soluble fraction (Li et al., 1999, Peng et al., 2001). Wheat SSII is predominantly granule-bound with only a small amount present in the soluble fraction (Gao and Chibbar, 2000). SSIII is exclusively found in the soluble fraction of wheat endosperm (Li et al., 2000).

SBEs can be separated into two major groups. SBE type I (or class B) comprises SBEI from maize (Baba et al, 1991), wheat (Morell et al, 1997, Repellin et al, 1997, Baga et al, 1999b), potato (Kossman et al, 1991), rice (Kawasaki et al, 1993), and cassava (Salehuzzaman et aL, 1992), and SBEII from pea (Burton et aL, 1995). The other group, SBE type II (or class A), comprises SBEII from maize (Gao et al, 1997), wheat (Nair et al, 1997), potato (Larsson et al, 1996), and Arabidopsis (Fisher et aL, 1996), SBEIII from rice (Mizuno et al, 1993), and SBEI from pea (Bhattacharyya et al, 1990). SBEI and SBEII are generally immunologically unrelated but have distinct catalytic activities. SBEI transfers long glucan chains and prefers amylose as a substrate, while SBEII acts primarily on amylopectin (Guan and Preiss, 1993). SBEII is further subclassified into SBEIIa and SBEIIb, each of which differs slightly in catalytic properties. The two SBEII forms are encoded by different genes and expressed in a tissue-specific manner (Gao et al., 1997, Fisher et al., 1996). Expression patterns of SBEIIa and SBEIIb in a particular tissue are specific to plant species. For example, the endosperm-specific SBEII in rice is SBEIIa (Yamanouchi and Nakamura, 1992), while that in barley is SBEIIb (Sun et al., 1998).

SDBE can be either alpha-1,4-targeting enzymes, such as amylases, starch phosphorylase (EC 2.4.1.1), disproportionating enzyme (EC 2.4.1.25), or alpha-1,6-targeting enzymes, such as direct debranching enzymes (e.g., limit dextrinase, EC 3.2.1.41, or isoamylase. EC 3.2.2.68), indirect debranching enzymes (e.g., alpha-1,4- and alpha-4,6-targeting enzymes).

Several starch biosynthetic proteins can be found bound to the interior of starch granules. A subset of these proteins has been designated the starch granule proteins (SGPs). Bread wheat starch granule proteins (SGPs) at least include SGP-1, SGP-2 and SGP-3 all with molecular masses >80 kd and the waxy protein (GBSS). The SGP-1 fraction of bread wheat was resolved into SGP-A1, SGP-B1, and SGP-D1, and genes encoding these proteins were localized to homoeologous group 7 chromosomes (Yamamori and Endo, 1996). Increased Amylose is observed by about 8% in the SGP-1 null line compared to the wild type inferring that SGP-1 is involved in amylopectin synthesis (Yamamori et al. (2000). The SGP-1 null line also shows deformed starch granules, lower overall starch content, altered amylopectin content, and reduced binding of SGP-2 and SGP-3 to starch granules. SGP-1 proteins are starch synthase class II enzymes and genes encoding these enzymes are designated SSII-A1, SSII-B1, and SSII-D1 (Li et al., 1999).

Durum wheat (Triticum turgidum L. var. durum) being tetraploid lacks the D genome of bread wheat but homoalleles for genes encoding the SGP-1 proteins are present on the A and B genomes (Lafiandra et al., 2010). The hexaploid SGP-A1 and SGP-B1 mutants from Yamamori and Endo (1996) were crossed into to durum cultivar Svevo. The SGP-A1/B1 null progeny exhibited 20% higher amylose content than Svevo wild type wheat, and had reduced binding of SGP-2 and SGP-3 to starch granules. These crosses between hexaploid bread wheat and tetraploid durum however are not considered commercially viable products.

Progeny of durum x hexaploid crosses are highly variable due to the variable incorporation of A and B genome loci with parental choice having a large impact upon cross success rates (Lanning et al. 2008; Martin et al. 2011). Moreover, the agronomic yield of lines from tetraploid x hexaploid wheat crosses would be expected to be lower than the adapted parents due to break up of adapted gene complexes. The disadvantages of hexaploid x durum crosses are well known in the art and to the present inventor's knowledge, no commonly grown durum varieties have resulted from crosses between durum and hexaploid wheat varieties. Therefore, the creation of high amylose durum wheat by specifically selecting for mutations in the durum starch synthase II genes is preferable to integration of hexaploid wheat starch synthase II mutations by crossing with durum wheat.

SGP-1 mutations are thought to alter the interactions of other granule bound enzymes by reducing their entrapment in starch granules. Similarly, barley SSIIa sex6 locus mutations have seeds with decreased starch content, increased amylose content (+45%) (70.3% for two SGP-1 mutants vs. 25.4% wild-type), deformed starch granules, and decreased binding of other SGPs (Morell et al. 2003). These barley ssIIa mutants had normal expression of SSI, SBEIIa, and SBEIIb based on western blot analysis of the soluble protein fraction demonstrating that there was not a global down regulation of starch synthesis genes. In SGP-1 triple mutant in bread wheat, SSI, SBEIIa, and SBEIIb proteins were stably expressed in developing seeds even though they are not present in the starch granule fraction (Kosar-Hashemi et al. 2007). Similar results relating the loss of SSII and increased amylose have been observed in both maize (Zhang et al. 2004) and pea (Craig et al. 1998).

Elimination of another important gene for amylopectin synthesis, SbeIIa, in durum wheat through RNA interference resulted in amylose increases ranging from +8% to +50% (24% wild-type vs. 31-75% SbeIIa RNAi lines), although protein content was found to be similar or, in some cases, lower than wild type. (Sestili et al. 2010b). It was determined through qRT-PCR that the silencing of SbeIIa resulted in elevated expression of the Waxy genes, SSIII, limit dextrinase (Ld1), and isoamylase-1 (Iso1). The very high amylose results observed by Sestili et al. (2010b) in some of their transgenic lines may not have been due solely to reduction of SbeIIa expression since SbeIIa mutagenesis resulted in amylose levels increases more similar to those of SSIIa mutations (28% sbeIIa double mutant versus 23% wild-type) (Hazard et al. 2012). To date a detailed expression profile of starch synthesis genes in a SGP-1 null background has not been reported. RNA-Seq is an emerging method that employs next-generation sequencing technologies that allow for gene expression analysis at the transcript level. RNA-Seq offers single-nucleotide resolution that is highly reproducible (Marioni et al. 2008) and compared to other methods has a greater sequencing sensitivity, a large dynamic range, and the ability to distinguish between differing alleles or isoforms of an expressed gene. RNA-Seq is therefore an ideal method to use to determine the effect a null SGP-1 genotype has on expression of other starch synthesis genes.

Cereals with high amylose content are desirable because they have more resistant starch. Resistant starch is starch that resists break down in the intestines of humans and animals and thus acts more like dietary fiber while promoting microbial fermentation (reviewed in Nugent 2005). Products that have high resistant starch levels are viewed as healthy as they increase overall colon health and decrease sugar release during food digestion. Rats fed whole seed meal from SbeIIa RNAi silenced bread wheat with an amylose content of 80% showed significant improvements in bowel health indices and increases in short-chained fatty acids (SCFAs), the end products of microbial fermentation (Regina et al. 2006). Similarly, when null ssIIa barley was fed to humans there was significant improvement in several bowel health indices and increases in SCFAs (Bird et al. 2008). An extruded cereal made from the ssIIa null barley also resulted in a lower glycemic index and lower plasma insulin response when fed to humans (King et al. 2008). The Yamamori et al. (2000) SGP-1 single mutants were crossed and backcrossed to an Italian breeding line then interbred to produce a triple null line from which whole grain bread was prepared. The resultant bread with the addition of lactic acid had increased resistant starch and a decreased glycemic index, but did not impact insulin levels (Hallstrom et al. 2011). Recently a high amylose corn was shown to alter insulin sensitivity in overweight men making them less likely to have insulin resistance, the pathophysiologic feature of diabetes (Maki et al. 2012).

In addition to the positive impact of increased amylose upon glycemic index, higher amylose could result in enhanced durum product quality. Pasta that is firmer when cooked is preferred as it resists overcooking and it is expected that high amylose should result in increased noodle firmness. Resistance to overcooking is positively correlated with pasta firmness. Current high amylose wheat based foods are prepared using standard amylose content wheat flour with the addition of high amylose maize starch (Thompson, 2000). To test the impact of high amylose upon durum quality Soh et al. (2006) varied durum flour amylose content by reconstituting durum flour with the addition of high amylose maize starch and wheat gluten. The increased amylose flours had weaker less extensible dough but resulted in firmer pasta. Pastas are a popular food item globally and are primarily made from durum semolina which is also utilized in a host of other culturally important foods. In some embodiments, the present invention develops a high-amylose durum line through the creation of mutations in SSIIa and to examine the effect a SGP-1 null genotype has on the expression of other genes involved in starch synthesis using RNA-Seq. These lines are tested for their end product quality and potential health benefits.

The ratio of amylose to amylopectin can be changed by selecting for alternate forms of the Wx loci or other starch synthase loci. Bread wheats carrying the null allele at all three Wx loci (Nakamura, et al., 1995) and durum wheat (Lafiandra et al., 2010 and Vignaux et at., 2004) with null alleles at both Wx loci are nearly devoid of amylose. On the other hand, bread wheat lines null at the three SGP-1 loci had 37.5% amylose compared to 24.9% amylose for the wild type genotype, determined by differential scanning calorimetry (Morita et al., 2005). Durum wheat lines with null alleles for both SGP-1 loci had 43.6% amylose compared to 23.0% for the wild type genotype (Lafiandra et al., 2010). Genotypes with a null allele at only one of the Wx loci (partial waxy) show only small reductions in amylose content. For example, Martin et al. (2004) showed a 2.4% difference in amylose between the wild type and null alleles in a recombinant inbred population segregating for Wx-B1. Vignaux et at., (2004) showed partial waxy durum genotypes reduced amylose by 1% but that difference was not significant.

High Fiber and Amylose Flour and Resulting Products

In Europe and in North America, pasta is traditionally prepared using 100% durum flour (Fuad and Prabhasanker 2010). In fact, the properties inherent in durum wheat flour make it ideally suited for pasta production since it imparts excellent color due to relatively high yellow pigments levels and good mixing properties inherent in native glutenin proteins (Dexter and Matson 1979; Fuad and Prabhasanker 2010). Recently, there has been a movement towards the production of flour products with improved nutritional properties including increased fiber and amylose content, as well as flour products having increased protein content.

Flour with increased dietary fiber is associated with better gastrointestinal health, and lower risk of diabetes and heart disease. Flour with high amylose content is also desirable as it has a higher content of resistant starch that is not absorbed during digestion and thus produces health benefits similar to those of dietary fiber. The increased amylose content of flour also influences the gelatinization and pasting properties of starch. Peak viscosity, final viscosity, break down, set back and peak time measured by Rapid Visco Analyzer (RVA) all declined with increasing amylose content for durum wheat (Lafiandra et al., 2010). The altered starch properties translate into changes in end product properties such as increased firmness and resistance to overcooking.

Increasing the dietary fiber, amylose, and/or protein content of wheat flour products can be achieved by incorporating various protein or dietary fiber enriched fractions such as pea flour, cereal-soluble or insoluble fiber. These types of mixed enriched flour blends however can lead to consumer acceptance issues. For example, blending barley flour into durum wheat to increase dietary fiber in pasta led to a dark colored product (Casiraghi et al., 2013). Fortification of pasta with pea flour deteriorated dough handling characteristics, and increased pasta cooking losses and led to lower tolerance to overcooking (Nielsen et al., 1980). Modifying durum wheat to increase amylose, protein, and dietary fiber is preferable to durum flour additives since it would result in a pasta having the improved nutrition while also retaining many of the desirable properties of durum flour. The final product then would match the North American and European preference for 100% durum pasta. Durum wheat flour with increased amylose, protein, and dietary fiber used in the preparation of pasta would likely be preferable even to that of standard whole grain durum pasta which is much darker in appearance and has reduced cooked firmness leading to reduced consumer acceptability (Manthey and Schorno 2002).

There has been recent interest in flours with higher amylose for food products. The main reason being that starch high in amylose has a higher fraction of resistant starch. Resistant starch is that fraction not absorbed in the small intestine during digestion (reviewed in Nugent 2005). Resistant starch is believed to provide health benefits similar to dietary fiber. Commercial high amylose food products have traditionally been developed using high amylose maize starch (Thompson, 2000). The development of high amylose bread wheat genotypes has made it possible to test the impact of high amylose wheat starch on end product quality. High amylose wheat flour produced harder textured dough and more viscous, and bread loaves that were smaller than normal flour (Morita et al., 2002). Substituting up to 50% high amylose wheat flour with the remainder being normal wheat flour gave bread quality that was not significantly different from the 100% normal wheat flour control (Hung et al., 2005). Durum wheat flours varying in amylose content can be made by reconstituting them with high amylose maize starch (Soh et al., 2006). The high amylose durum wheat flours had dough that was weaker and less extensible. The pasta produced from these flours tended to be firmer with more cooking loss with increasing amylose content.

Even small, incremental increases in amylose may impact end product quality. Consumers prefer pasta that is firm and is tolerant to over cooking. Reduced amylose produces noodles that are softer in texture (Oda et al 1980; Miura and Tanii 1994; Zhao et al 1998). The impact of small increases in amylose content on durum product quality is not known. For example, attention has been devoted to Asian noodle quality from partial waxy flours. Partial waxy soft wheat cultivars, due to a mutation at one of the Wx loci, are preferred for udon noodles as they confer softer texture to the noodles (Oda et al 1980; Miura and Tanii 1994; Zhao et al 1998). Partial waxy genotype did not differ from wild type for white salted noodle firmness in a hard wheat recombinant inbred population (Martin et al., 2004). However, partial waxy genotype conferred greater loaf volume and bread was softer textured than that from the wild type.

Waxy durum isolines produced pasta that was softer with more cooking loss and which was less resistant to over cooking than pasta from normal lines. However, the partial waxy isolines produced pasta with properties not statistically different from the wild type lines (Vignaux et al., 2005).

The present inventors surveyed world durum wheat germplasm and identified two genotypes that lacked the SGP-A1 protein. These genotypes were crossed to an adapted durum genotype to create populations segregating for the SSIIa-Ab null allele. Influence of allelic variation at the SSI-A41 locus on semolina properties and end product quality using noodles as a test product were investigated.

Identification and Creation of Mutant Starch Synthesis Genes in Durum

Durum wheat with one or more mutant alleles of one or more starch synthesis genes can be created and identified. In some embodiments, such mutant alleles happen naturally during evolution. In some embodiments, such mutant alleles are created by artificial methods, such as mutagenesis (e.g., chemical mutagenesis, radiation mutagenesis, transposon mutagenesis, insertional mutagenesis, signature tagged mutagenesis, site-directed mutagenesis, and natural mutagenesis), antisense, knock-outs, and/or RNA interference.

Various types of mutagenesis can be used to produce and/or isolate variant nucleic acids that encode for protein molecules and/or to further modify/mutate the proteins of a starch synthesis gene. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like. For more information of mutagenesis in plants, such as agents, protocols, see Acquaah et al. (Principles of plant genetics and breeding, Wiley-Blackwell, 2007, ISBN 1405136464, 9781405136464, which is herein incorporated by reference in its entirety). Methods of disrupting plant genes using RNA interference is described later in the specification.

Gene function can also be interrupted and/or altered by RNA interference (RNAi). RNAi is the process of sequence-specific, post-transcriptional gene silencing or transcriptional gene silencing in animals and plants, initiated by double-stranded RNA (dsRNA) that is homologous in sequence to the silenced gene. The preferred RNA effector molecules useful in this invention must be sufficiently distinct in sequence from any host polynucleotide sequences for which function is intended to be undisturbed after any of the methods of this invention are performed. Computer algorithms may be used to define the essential lack of homology between the RNA molecule polynucleotide sequence and host, essential, normal sequences.

The term "dsRNA" or "dsRNA molecule" or "double-strand RNA effector molecule" refers to an at least partially double-strand ribonucleic acid molecule containing a region of at least about 19 or more nucleotides that are in a double-strand conformation. The double-stranded RNA effector molecule may be a duplex double-stranded RNA formed from two separate RNA strands or it may be a single RNA strand with regions of self-complementarity capable of assuming an at least partially double-stranded hairpin conformation (i.e., a hairpin dsRNA or stem-loop dsRNA). In various embodiments, the dsRNA consists entirely of ribonucleotides or consists of a mixture of ribonucleotides and deoxynucleotides, such as RNA/DNA hybrids. The dsRNA may be a single molecule with regions of self-complementarity such that nucleotides in one segment of the molecule base pair with nucleotides in another segment of the molecule. In one aspect, the regions of self-complementarity are linked by a region of at least about 3-4 nucleotides, or about 5, 6, 7, 9 to 15 nucleotides or more, which lacks complementarity to another part of the molecule and thus remains single-stranded (i.e., the "loop region"). Such a molecule will assume a partially double-stranded stem-loop structure, optionally, with short single stranded 5' and/or 3' ends. In one aspect the regions of self-complementarity of the hairpin dsRNA or the double-stranded region of a duplex dsRNA will comprise an Effector Sequence and an Effector Complement (e.g., linked by a single-stranded loop region in a hairpin dsRNA). The Effector Sequence or Effector Strand is that strand of the double-stranded region or duplex which is incorporated in or associates with RISC. In one aspect the double-stranded RNA effector molecule will comprise an at least 19 contiguous nucleotide effector sequence, preferably 19 to 29, 19 to 27, or 19 to 21 nucleotides, which is a reverse complement to a starch synthesis gene.

In some embodiments, the dsRNA effector molecule of the invention is a "hairpin dsRNA", a "dsRNA hairpin", "short-hairpin RNA" or "shRNA", i.e., an RNA molecule of less than approximately 400 to 500 nucleotides (nt), or less than 100 to 200 nt, in which at least one stretch of at least 15 to 100 nucleotides (e.g., 17 to 50 nt, 19 to 29 nt) is based paired with a complementary sequence located on the same RNA molecule (single RNA strand), and where said sequence and complementary sequence are separated by an unpaired region of at least about 4 to 7 nucleotides (or about 9 to about 15 nt, about 15 to about 100 nt, about 100 to about 1000 nt) which forms a single-stranded loop above the stem structure created by the two regions of base complementarity. The shRNA molecules comprise at least one stem-loop structure comprising a double-stranded stem region of about 17 to about 500 bp; about 17 to about 50 bp; about 40 to about 100 bp; about 18 to about 40 bp; or from about 19 to about 29 bp; homologous and complementary to a target sequence to be inhibited; and an unpaired loop region of at least about 4 to 7 nucleotides, or about 9 to about 15 nucleotides, about 15 to about 100 nt, about 250-500 bp, about 100 to about 1000 nt, which forms a single-stranded loop above the stem structure created by the two regions of base complementarity. It will be recognized, however, that it is not strictly necessary to include a "loop region" or "loop sequence" because an RNA molecule comprising a sequence followed immediately by its reverse complement will tend to assume a stem-loop conformation even when not separated by an irrelevant "stuffer" sequence.

The expression construct of the present invention comprising DNA sequence which can be transcribed into one or more double-stranded RNA effector molecules can be transformed into a wheat plant, wherein the transformed plant produces different starch compositions than the untransformed plant. The target sequence to be inhibited by the dsRNA effector molecule include, but are not limited to, coding region, 5' UTR region, 3' UTR region of fatty acids synthesis genes.

The effects of RNAi can be both systemic and heritable in plants. In plants, RNAi is thought to propagate by the transfer of siRNAs between cells through plasmodesmata. The heritability comes from methylation of promoters targeted by RNAi; the new methylation pattern is copied in each new generation of the cell. A broad general distinction between plants and animals lies in the targeting of endogenously produced miRNAs; in plants, miRNAs are usually perfectly or nearly perfectly complementary to their target genes and induce direct mRNA cleavage by RISC, while animals' miRNAs tend to be more divergent in sequence and induce translational repression. Detailed methods for RNAi in plants are described in David Allis et al (Epigenetics, CSHL Press, 2007, ISBN 0879697245, 9780879697242), Sohail et al (Gene silencing by RNA interference: technology and application, CRC Press, 2005, ISBN 0849321417, 9780849321412), Engelke et al. (RAN Interference, Academic Press, 2005, ISBN 0121827976, 9780121827977), and Doran et al. (RNA Interference: Methods for Plants and Animals, CABI, 2009, ISBN 1845934105, 9781845934101), which are all herein incorporated by reference in their entireties for all purposes.

In some embodiments, mutant starch synthesis genes in durum wheat can be identified by screening durum wheat populations based on one or more phenotypes. In some embodiments, the phenotype is changes in flour swelling power.

In some embodiments, mutant starch synthesis genes in durum wheat can be identified by screening durum wheat populations based on PCT amplification and sequencing of one or more starch synthesis genes in durum wheat.

In some embodiments, mutant starch synthesis genes in durum wheat can be identified by TILLING®. Detailed description on methods and compositions on TILLING® can be found in U.S. Pat. No. 5,994,075, US 2004/0053236 A1, WO 2005/055704, and WO 2005/048692, each of which is hereby incorporated by reference for all purposes.

TILLING® (Targeting Induced Local Lesions in Genomes) is a method in molecular biology that allows directed identification of mutations in a specific gene. TILLING® was introduced in 2000, using the model plant *Arabidopsis thaliana*. TILLING® has since been used as a reverse genetics method in other organisms such as zebrafish, corn, wheat, rice, soybean, tomato and lettuce. The method combines a standard and efficient technique of mutagenesis with a chemical mutagen (e.g., Ethyl methanesulfonate (EMS)) with a sensitive DNA screening-technique that identifies single base mutations (also called point mutations) in a target gene. EcoTILLING is a method that uses TILLING® techniques to look for natural mutations in individuals, usually for population genetics analysis. See Comai, et al., 2003, Efficient discovery of DNA polymorphisms in natural populations by EcoTILLING. The Plant Journal 37, 778-786. Gilchrist et al. 2006. Use of EcoTILLING as an efficient SNP discovery tool to survey genetic variation in wild populations of *Populus trichocarpa*. Mol. Ecol. 15, 1367-1378. Mejlhede et al. 2006. EcoTILLING for the identification of allelic variation within the powdery mildew resistance genes mlo and Mla of barley. Plant Breeding 125, 461-467. Nieto et al. 2007, EcoTILLING for the identification of allelic variants of melon eIF4E, a factor that controls virus susceptibility. BMC Plant Biology 7, 34-42, each of which is incorporated by reference hereby for all purposes. DEcoTILLING is a modification of TILLING® and EcoTILLING which uses an inexpensive method to identify fragments (Garvin et al., 2007, DEco-TILLING: An inexpensive method for SNP discovery that reduces ascertainment bias. Molecular Ecology Notes 7, 735-746).

The invention also encompasses mutants of a starch synthesis gene. In some embodiments, the starch synthesis gene is selected from the group consisting of genes encoding GBSS, waxy proteins, SBE I and II, starch de-branching enzymes, and SSI, SSII, SSIII, and SSIV. In some embodiments, the starch synthesis gene is SSII. The mutant may contain alterations in the amino acid sequences of the constituent proteins. The term "mutant" with respect to a polypeptide refers to an amino acid sequence that is altered by one or more amino acids with respect to a reference sequence. The mutant can have "conservative" changes, or "nonconservative" changes, e.g., analogous minor variations can also include amino acid deletions or insertions, or both.

The mutations in a starch synthesis gene can be in the coding region or the non-coding region of the starch synthesis genes. The mutations can either lead to, or not lead to amino acid changes in the encoded starch synthesis gene. In some embodiments, the mutations can be missense, severe missense, silent, nonsense mutations. For example, the mutation can be nucleotide substitution, insertion, deletion, or genome re-arrangement, which in turn may lead to reading frame shift, amino acid substitution, insertion, deletion, and/or polypeptides truncation. As a result, the mutant starch synthesis gene encodes a starch synthesis polypeptide having modified activity on compared to a polypeptide encoded by a reference allele.

As used herein, a nonsense mutation is a point mutation, e.g., a single-nucleotide polymorphism (SNP), in a sequence of DNA that results in a premature stop codon, or a nonsense codon in the transcribed mRNA, and in a truncated, incomplete, and usually nonfunctional protein product. A missense mutation (a type of nonsynonymous mutation) is a point mutation in which a single nucleotide is changed, resulting in a codon that codes for a different amino acid (mutations that change an amino acid to a stop codon are considered nonsense mutations, rather than missense mutations). This can render the resulting protein nonfunctional. Silent mutations are DNA mutations that do not result in a change to the amino acid sequence of a protein. They may occur in a non-coding region (outside of a gene or within an intron), or they may occur within an exon in a manner that does not alter the final amino acid sequence. A severe missense mutation changes the amino acid, which lead to dramatic changes in conformation, charge status etc.

The mutations can be located at any portion of a starch synthesis gene, for example, at the 5', the middle, or the 3' of a starch synthesis gene, resulting mutations in any portions of the encoded starch synthesis protein.

Mutant starch synthesis protein of the present invention can have one or more modifications to the reference allele, or biologically active variant, or fragment thereof. Particularly suitable modifications include amino acid substitutions, insertions, deletions, or truncation. In some embodiments, at least one non-conservative amino acid substitution, insertion, or deletion in the protein is made to disrupt or modify the protein activity. The substitutions may be single, where only one amino acid in the molecule has been substituted, or they may be multiple, where two or more amino acids have been substituted in the same molecule. Insertional mutants are those with one or more amino acids inserted immediately adjacent to an amino acid at a particular position in the reference protein molecule, biologically active variant, or fragment thereof. The insertion can be one or more amino acids. The insertion can consist, e.g., of one or two conservative amino acids. Amino acids similar in charge and/or structure to the amino acids adjacent to the site of insertion are defined as conservative. Alternatively, mutant starch synthesis protein includes the insertion of an amino acid with a charge and/or structure that is substantially different from the amino acids adjacent to the site of insertion. In some other embodiments, the mutant starch synthesis protein is a truncated protein losing one or more domains compared to a reference protein.

In some examples, mutants can have at least 1, 2, 3, 4, 5, 10, 15, 20, 25, 30, 40, 50, or 100 amino acid changes. In some embodiments, at least one amino acid change is a conserved substitution. In some embodiments, at least one amino acid change is a non-conserved substitution. In some embodiments, the mutant protein has a modified enzymatic activity when compared to a wild type allele. In some embodiments, the mutant protein has a decreased or increased enzymatic activity when compared to a wild type allele. In some embodiments, the decreased or increased enzymatic activity when compared to a wild type allele leads to amylose content change in the durum wheat.

Conservative amino acid substitutions are those substitutions that, when made, least interfere with the properties of the original protein, that is, the structure and especially the function of the protein is conserved and not significantly changed by such substitutions. Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain. Further information about conservative substitutions can be found, for instance, in Ben Bassat et al. (*J. Bacteriol.*, 169:751-757, 1987), O'Regan et al. (*Gene*, 77:237-251, 1989), Sahin-Toth et al. (*Protein Sci.*, 3:240-247, 1994), Hochuli et al. (*Bio/Technology*, 6:1321-1325, 1988) and in widely used textbooks of genetics and molecular biology. The Blosum matrices are commonly used for determining the relatedness of polypeptide sequences. The Blosum matrices were created using a large database of trusted alignments (the BLOCKS database), in which pair-wise sequence alignments related by less than some threshold percentage identity were counted (Henikoff et al., *Proc. Natl. Acad. Sci. USA*, 89:10915-10919, 1992). A threshold of 90% identity was used for the highly conserved target frequencies of the BLOSUM90 matrix. A threshold of 65% identity was used for the BLOSUM65 matrix. Scores of zero and above in the Blosum matrices are considered "conservative substitutions" at the percentage identity selected. The following table shows exemplary conservative amino acid substitutions.

| Original Residue | Very Highly-Conserved Substitutions | Highly Conserved Substitutions (from the Blosum90 Matrix) | Conserved Substitutions (from the Blosum65 Matrix) |
|---|---|---|---|
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

In some embodiments, the mutant durum wheat comprises mutations associated with a starch synthesis gene of the same genome that can be traced back to one common ancestor, such as the "A" type genome of durum wheat or the "B" type genome of durum wheat. For example, a mutant durum wheat having a mutated SSIIa-A or a mutated SSIIa-B is included. In some embodiments, one or both alleles of the starch synthesis gene within a given type of genome are mutated.

In some embodiments, the mutant durum wheat comprise mutations associated with the same starch synthesis gene of different genomes that can be traced back to two common ancestors, such as the "A" type genome and the "B" type genome of durum wheat. For example, a mutant durum wheat having a mutated SSIIa-A and a mutated SSIIa-B is included. In some embodiments, one or both alleles of the starch synthesis gene within the two types of genomes are mutated.

Methods of Modifying Durum Phenotypes

The present invention further provides methods of modifying/altering/improving durum phenotypes. As used herein, the term "modifying" or "altering" refers to any change of phenotypes when compared to a reference variety, e.g., changes associated with starch properties. The term "improving" refers to any change that makes the durum wheat better in one or more qualities for industrial or nutritional applications. Such improvement includes, but is not limited to, improved quality as meal, improved quality as raw material to produce a wide range of end products.

In some embodiments, the modified/altered/improved phenotypes are related to starch. Starch is the most common carbohydrate in the human diet and is contained in many foods. The major sources of starch intake worldwide are the cereals (rice, wheat, and maize) and the root vegetables (potatoes and cassava). Widely used prepared foods containing starch are bread, pancakes, cereals, noodles, pasta, porridge and tortilla. The starch industry extracts and refines starches from seeds, roots and tubers, by wet grinding, washing, sieving and drying. Today, the main commercial refined starches are cornstarch, tapioca, wheat and potato starch.

Starch can be hydrolyzed into simpler carbohydrates by acids, various enzymes, or a combination of the two. The resulting fragments are known as dextrins. The extent of conversion is typically quantified by dextrose equivalent (DE), which is roughly the fraction of the glycosidic bonds in starch that have been broken.

Some starch sugars are by far the most common starch based food ingredient and are used as sweetener in many drinks and foods. They include, but are not limited to, maltodextrin, various glucose syrup, dextrose, high fructose syrup, and sugar alcohols.

A modified starch is a starch that has been chemically modified to allow the starch to function properly under conditions frequently encountered during processing or storage, such as high heat, high shear, low pH, freeze/thaw and cooling. Typical modified starches for technical applications are cationic starches, hydroxyethyl starch and carboxymethylated starches.

As an additive for food processing, food starches are typically used as thickeners and stabilizers in foods such as puddings, custards, soups, sauces, gravies, pie fillings, and salad dressings, and to make noodles and pastas.

In the pharmaceutical industry, starch is also used as an excipient, as tablet disintegrant or as binder.

Starch can also be used for industrial applications, such as papermaking, corrugated board adhesives, clothing starch, construction industry, manufacture of various adhesives or glues for book-binding, wallpaper adhesives, paper sack production, tube winding, gummed paper, envelope adhesives, school glues and bottle labeling. Starch derivatives, such as yellow dextrins, can be modified by addition of some chemicals to form a hard glue for paper work; some of those forms use borax or soda ash, which are mixed with the starch solution at 50-70° C. to create a very good adhesive.

Starch is also used to make some packing peanuts, and some drop ceiling tiles. Textile chemicals from starch are used to reduce breaking of yarns during weaving; the warp yarns are sized. Starch is mainly used to size cotton based yarns. Modified starch is also used as textile printing thickener. In the printing industry, food grade starch is used in the manufacture of anti-set-off spray powder used to separate printed sheets of paper to avoid wet ink being set off. Starch is used to produce various bioplastics, synthetic polymers that are biodegradable. An example is polylactic acid. For body powder, powdered starch is used as a substitute for talcum powder, and similarly in other health and beauty products. In oil exploration, starch is used to adjust the viscosity of drilling fluid, which is used to lubricate the drill head and suspend the grinding residue in petroleum extraction. Glucose from starch can be further fermented to biofuel corn ethanol using the so called wet milling process. Today most bioethanol production plants use the dry milling process to ferment corn or other feedstock directly to ethanol. Hydrogen production can use starch as the raw material, using enzymes.

Resistant starch is starch that escapes digestion in the small intestine of healthy individuals. High amylose starch from corn has a higher gelatinization temperature than other types of starch and retains its resistant starch content through baking, mild extrusion and other food processing techniques. It is used as an insoluble dietary fiber in processed foods such as bread, pasta, cookies, crackers, pretzels and other low moisture foods. It is also utilized as a dietary supplement for its health benefits. Published studies have shown that Type 2 resistant corn helps to improve insulin sensitivity, increases satiety and improves markers of colonic function. It has been suggested that resistant starch contributes to the health benefits of intact whole grains.

Resistant starch can be produced from the durum wheat plants of the present invention. The resistant starch may have one or more the following features:

Fiber fortification: the resistant starch is good or excellent fiber source. The United States Department of Agriculture and the health organizations of other foreign countries set the standards for what constitutes a good or excellent source of dietary fiber.

Low caloric contribution: the starch may contain less than about 10 kcal/g, 5 kcal/g, 1 kcal/g, or 0.5 kcal/g, which results in about 90% calorie reduction compared to typical starch.

Low glycemic/insulin response

Good flour replacement, because it is (1) easy to be incorporated into formulations with minimum or no formulation changes necessary, (2) natural fit for wheat-based products, and (3) potential to reduce retrogradation and staling. Staling is a chemical and physical process in bread and other foods that reduces their palatability.

Low water binding capacity: the starch possesses lower water holding capacity than most other fiber sources, including other types of resistant starches. It reduces water in the formula, ideal for targeting crispiness, and improves shelf life regarding micro-activity and retrogradation.

Process tolerant: the starch is stable against energy intensive procedures, such as extrusion, pressure cooking, etc.

Sensory attributes: such as smooth, non-gritty texture, white, "invisible" fiber source, and neutral in flavor.

Therefore, flour or starch produced from the durum wheat of the present invention can be used to replace bread wheat flour or starch, to produce wheat bread, muffins, buns, pasta, noodles, tortillas, pizza dough, breakfast cereals, cookies, waffles, bagels, biscuits, snack foods, brownies, pretzels, rolls, cakes, and crackers, wherein the food products may have one or more desired features.

In some embodiments, the mutant durum wheat has one or more phenotypes when compared to a wild-type durum wheat of the same species, which includes, but are not limited to, modified gelatinization temperature (e.g., a modified amylopectin gelatinization peaks, and/or a modified enthalpy), modified amylose content, modified resistant amylose content, modified starch quality, modified flour swelling power, modified protein content (e.g., higher protein content), modified kernel weight, modified kernel hardness, and modified semolina yield.

Figure 5:
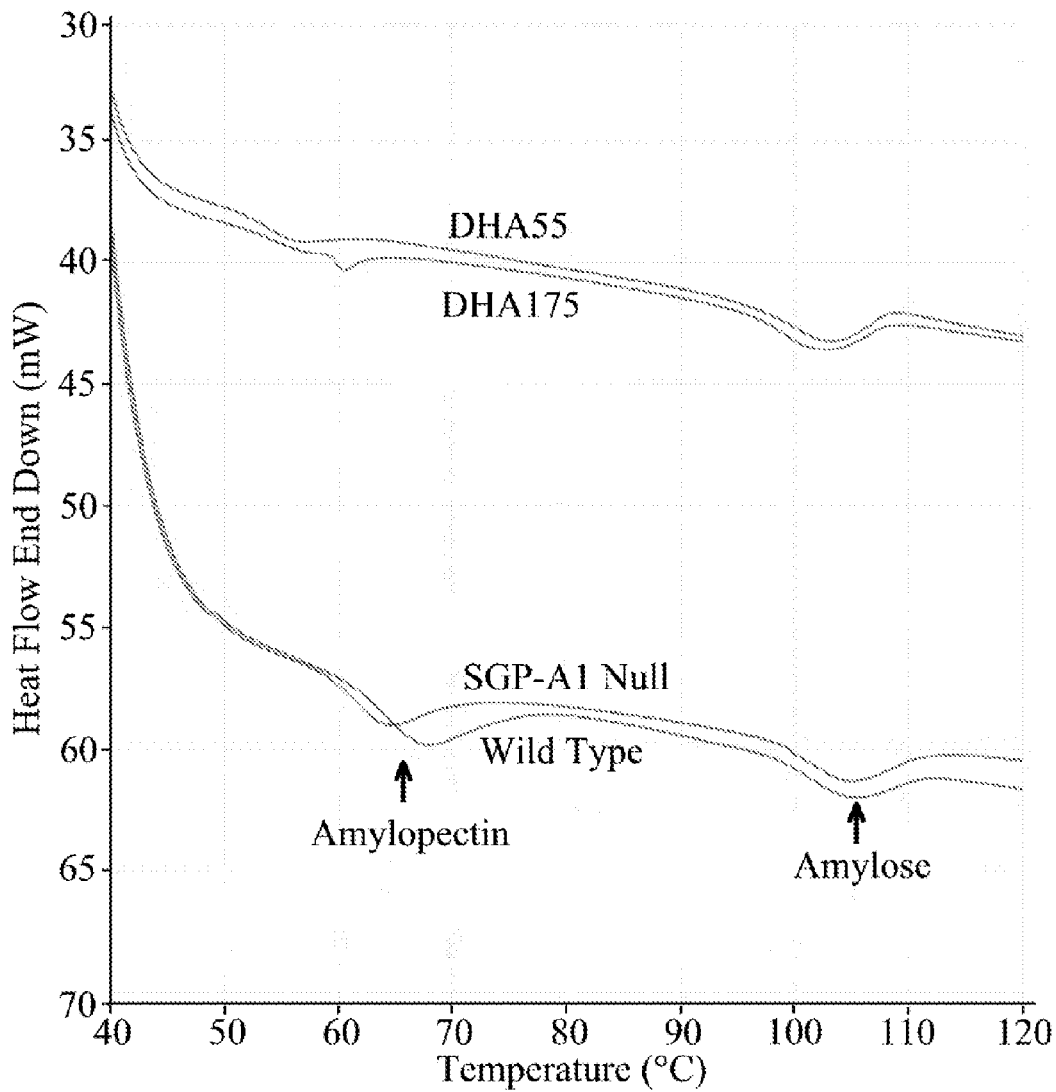
FIG. 5 depicts DSC thermogram of starches from Mountrail/PI-330546 $F_5$ SGP-1 wild-type, Mountrail/PI-330546 $F_5$ SGP-A1 null and SGP-1 double null genotypes DHA175 and DHA55. Approximately 10 mg of starch (actual weight was recorded) per sample was placed in a high-pressure stainless steel pan along with 55 μL of ddH2O. The pan was sealed with an O-ring and cover and the starch was left to hydrate overnight at room temperature. Samples were re-weighed the next day then placed at 25° C. for two min to equilibrate before they were heated to 120° C. at 10° C./min. Heat transfer in the samples was compared to an empty stainless steel pan as a reference. The Pyris software was used to generate thermograms and calculate transition temperatures and heat of physical transition. Amylose was determined via DSC using the methods described in Polaske et al. (2005). Statistical analysis on amylose content was carried out using PROC GLM and t-tests with an alpha of 0.05 in SAS 9.0 (SAS Institute, Cary, N.C.). SGP-1 double null lines show an altered amylopectin gelatinization profile that occurs at cooler temperatures and has decreased enthalpy compared to the wild-type and SGP-A1 null controls.

In some embodiments, the methods relate to modifying gelatinization temperature of durum wheat, such as modifying amylopectin gelatinization peaks and/or modifying enthalpy. Modified gelatinization temperature results in altered temperatures required for cooking starch based products. Different degrees of starch gelatinization impact the level of resistant starch. For example, endothermic peaks I and II of FIG. 5 are due to the resolved gelatinization and the melting of the fat/amylose complex, respectively. In some embodiments, the amylopectin gelatinization profile of the durum wheat of the present invention is changed compared to reference durum wheat, such as a wild-type durum wheat. In some embodiments, the amylopectin gelatinization temperature of the durum wheat of the present invention is significantly lower than that of a wild-type control. For example, the amylopectin gelatinization temperature of the durum wheat of the present invention is about 1° C., 2° C., 3° C., 4° C., 5° C., 6° C., 7° C., 8° C., 9° C., 10° C., 15° C., 20° C., 25° C. or more lower than that of a wild-type control based on peak height on a Differential Scanning Calorimetry (DSC) thermogram, under the same heating rate. Starches having reduced gelatinization are associated with those starches having increased amylose and reduced glycemic index. They are also associated with having firmer starch based gels upon retrogradation as in cooked and cooled pasta.

In some embodiments, the change in enthalpy of the durum wheat starch of the present invention is dramatically smaller compared to that of a wild type control. For example, as measured by DSC thermogram, the heat flow transfer in the durum wheat starch of the present invention is only about ½, ⅓, or ¼ of that of a wild-type control.

Starch gelatinization is a process that breaks down the intermolecular bonds of starch molecules in the presence of water and heat, allowing the hydrogen bonding sites (the hydroxyl hydrogen and oxygen) to engage more water. This irreversibly dissolves the starch granule. Penetration of water increases randomness in the general starch granule structure and decreases the number and size of crystalline regions. Crystalline regions do not allow water entry. Heat causes such regions to become diffuse, so that the chains begin to separate into an amorphous form. Under the microscope in polarized light starch loses its birefringence and its extinction cross. This process is used in cooking to make roux sauce. The gelatinization temperature of starch depends upon plant type and the amount of water present, pH, types and concentration of salt, sugar, fat and protein in the recipe, as well as derivatisation technology used. The gelatinization temperature depends on the degree of cross-linking of the amylopectin, and can be modified by genetic manipulation of starch synthase genes.

In one embodiment, the methods relate to modifying amylose content of durum wheat, such as resistant amylose content. Flour with increased resistant amylose content can be used to make firmer pasta with greater resistance to overcooking as well as reduced glycemic index and increased dietary fiber and resistant starch. In some embodiments, the amylose content and/or the resistant amylose content of the durum wheat of the present invention and the products produced from said wheat, is modified (e.g., increased) by about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 79%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 300%, 400%, 500%, 600%, 700%, 800%, 900%, 1000% or more compared to that of a wild-type durum wheat.

In some embodiments, the amylose content and/or resistant amylose content of the durum wheat of the present invention and products produced from said wheat is about 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 79%, 79%, 80%, 81%, 82%, 83%, 84%, 85%, 86%, 87%, 88%, 89%, 90%, 91%, 92%, 93%, 94%, 95%, 96%, 97%, 98%, or 99%. Thus, wild type durum wheat analyzed by exemplary methods described herein, was found to have an amylose content of about 38% as compared to a high amylose durum wheat of the invention which was found to have significantly more than 38% amylose content including, e.g., about 53% amylose.

In some embodiments, the methods relate to modifying starch quality of durum wheat.

In some embodiments, the methods relate to modifying flour swelling power (FSP) of durum wheat. Reduced FSP should reduced weight of the noodles and increase firmness. In some embodiments, based on the methods described in Mukasa et al. (Comparison of flour swelling power and water-soluble protein content between self-pollinating and cross-pollinating buckwheat, Fagopyrum 22:45-50 (2005), the FSP of the durum wheat of the present invention is modified (e.g., decreased) by about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 79%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 300%, 400%, 500%, 600%, 700%, 800%, 900%, 1000% or more compared to that of a wild-type durum wheat. Flour swelling power may be negatively correlated with noodle firmness but positively correlated with cook weight meaning that as FSP declined noodles were firmer and not as heavy.

In some embodiments, the FSP of the durum wheat of the present invention and products produced from said wheat is 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 (g/g). Thus, wild type durum wheat analyzed by exemplary methods described herein, was found to have an FSP of about 8.4 as compared to a high amylose durum wheat of the invention which was found to have significantly less than 8.4 FSP, including, e.g., about 5.8 FSP.

In some embodiments, the methods relate to modifying amylopectin content of durum wheat. Amylose and amylopectin are interrelated so decreasing amylopectin is the same benefit as increased amylose. Decreasing amylose (and/or increasing amylopectin) is associated with increased FSP, reduced retrogradation and softer baked products and noodles. Increasing amylopectin is also associated with reduced rate of staling. In some embodiments, the amylopectin content of the durum wheat of the present invention is modified (e.g., decreased) by about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 79%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 300%, 400%, 500%, 600%, 700%, 800%, 900%, 1000% or more compared to that of a wild-type durum wheat.

In some embodiments, the amylopectin content of the durum wheat of the present invention and products produced from said wheat is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 79%, 79%, 80%, 81%, 82%, 83%, 84%, 85%, 86%, 87%, 88%, 89%, 90%, 91%, 92%, 93%, 94%, 95%, 96%, 97%, 98%, or 99%.

In some embodiments, the methods relate to modifying protein content of durum wheat. In some embodiments, the protein content of the durum wheat of the present invention and the products produced from said durum wheat, is modified (e.g., increased) by about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 79%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 300%, 400%, 500%, 600%, 700%, 800%, 900%, 1000% or more compared to that of a wild-type durum wheat.

In some embodiments, the protein content of the durum wheat of the present invention and products produced from said wheat is about 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 79%, 79%, 80%, 81%, 82%, 83%, 84%, 85%, 86%, 87%, 88%, 89%, 90%, 91%, 92%, 93%, 94%, 95%, 96%, 97%, 98%, or 99%.

Thus, wild type durum wheat products analyzed by exemplary methods described herein, was found to have a protein content of about 16.8% as compared to a high amylose durum wheat product of the invention which was found to have significantly more than 16.8% protein content, including, e.g., about 22.8% protein. Increased protein content means greater nutritional value (reduced glycemic index) as well as greater functionality. In terms of pasta quality, increased protein content would be associated with reduced FSP and increased pasta firmness.

In some embodiments, the methods relate to modifying dietary fiber content in the durum wheat grain. In some embodiments, the dietary fiber content in the durum wheat grain of the present invention and the products produced from said durum wheat, is modified (e.g., increased) by about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 79%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 300%, 400%, 500%, 600%, 700%, 800%, 900%, 1000% or more compared to that of a wild-type durum wheat.

In some embodiments, the dietary content of the durum wheat of the present invention and products produced from said wheat is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 79%, 79%, 80%, 81%, 82%, 83%, 84%, 85%, 86%, 87%, 88%, 89%, 90%, 91%, 92%, 93%, 94%, 95%, 96%, 97%, 98%, or 99%.

Thus, wild type durum wheat products analyzed by exemplary methods described herein, was found to have a dietary fiber content of about 3% as compared to a high amylose durum wheat product of the invention which was found to have significantly more than 3% dietary fiber, including, e.g., about 8.6% dietary fiber. Advantages of consuming products made from grain with increased dietary fiber include, but are not limited to the production of healthful compounds during the fermentation of the fiber, and increased bulk, softened stool, and shortened transit time through the intestinal tract.

In some embodiments, the methods relate to modifying fat content in the durum wheat grain. In some embodiments, the fat content in the durum wheat grain of the present invention is modified (e.g., increased) by about 1%, 2%, 3%, 4%, 5%, 6%, 7%, 8%, 9%, 100%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 79%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 300%, 400%, 500%, 600%, 700%, 800%, 900%, 1000% or more compared to that of a wild-type durum wheat.

In some embodiments, the fat content of the durum wheat of the present invention and products produced from said wheat is about 00%, 0.1%, 0.2%, 0.3%, 0.4%, 0.5%, 0.6%, 0.7%, 0.8%, 0.9%, 1%, 1.2%, 1.3%, 1.4%, 1.5%, 1.6%, 1.7%, 1.8%, 1.9%, 2%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40%.

Thus, wild type durum wheat products analyzed by exemplary methods described herein, was found to have a fat content of about 1.9% as compared to a high amylose durum wheat product of the invention which was found to have significantly more than 1.9% fat content, including, e.g., about 3.5% fat.

In some embodiments, the methods relate to modifying resistant starch content in the durum wheat grain. In some embodiments, the resistant starch content in the durum wheat grain of the present invention is modified (e.g., increased) by about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 79%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 300%, 400%, 500%, 600%, 700%, 800%, 900%, 1000% or more compared to that of a wild-type durum wheat.

In some embodiments, the resistant starch content of the durum wheat of the present invention and products produced from said wheat is about 0.1%, 0.2%, 0.3%, 0.4%, 0.5%, 0.6%, 0.7%, 0.8%, 0.9%, 1%, 1.2%, 1.3%, 1.4%, 1.5%, 1.6%, 1.7%, 1.8%, 1.9%, 2%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, 5%, 5.1%, 5.2%, 5.3%, 5.4%, 5.5%, 5.6%, 5.7%, 5.8%, 5.9%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 79%, 79%, 80%, 81%, 82%, 83%, 84%, 85%, 86%, 87%, 88%, 89%, 90%, 91%, 92%, 93%, 94%, 95%, 96%, 97%, 98%, or 99%.

Thus, wild type durum wheat products analyzed by exemplary methods described herein, was found to have a resistant starch content of about <2% as compared to a high amylose durum wheat product of the invention which was found to have significantly more than <2% resistant starch, including, e.g., about 3.8% resistant starch.

In some embodiments, the methods relate to modifying ash content in the durum wheat grain. In some embodiments, the ash content in the durum wheat grain of the present invention is modified (e.g., increased) by about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 79%, 79%, 80%, 81%, 82%, 83%, 84%, 85%, 86%, 87%, 88%, 89%, 90%, 91%, 92%, 93%, 94%, 95%, 96%, 95%, 98%, 9996%, 97%98%, 99%, 00%, 110%, 120, 130%, 140%, 150%, 160%, 170%, 180%, 190%, 200%, 300%, 400%, 500%, 600%, 700%, 800%, 900%, 1000% or more compared to that of a wild-type durum wheat.

In some embodiments, the ash content of the durum wheat of the present invention and products produced from said wheat is about 0.1%, 0.2%, 0.3%, 0.4%, 0.5%, 0.6%, 0.7%, 0.8%, 0.9%, 1%, 1.2%, 1.3%, 1.4%, 1.5%, 1.6%, 1.7%, 1.8%, 1.9%, 2%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, 5%, 5.1%, 5.2%, 5.3%, 5.4%, 5.5%, 5.6%, 5.7%, 5.8%, 5.9%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40%.

Thus, wild type durum wheat products analyzed by exemplary methods described herein, was found to have an ash content of about 0.7% as compared to a high amylose durum wheat product of the invention which was found to have significantly more than 0.7% ash content, including, e.g., about 1.2% ash.

In some embodiments, the methods relate to modifying kernel weight of durum wheat. In some embodiments, the kernel weight of the durum wheat of the present invention is modified (e.g., decreased) by about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 79%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 1500%, 160%, 170%, 180%, 190%, 200%, 300%, 400%, 500%, 600%, 700%, 800%, 900%, 1000% or more compared to that of a wild-type durum wheat. For example, the SGP1 null of the present invention may have reduced kernel weight. Reduced kernel weight is often associated with increased protein content and its associated benefits as described above. Increased seed weight without impacting seed number leads to increased yield and generally increased starch content.

In some embodiments, the kernel weight of the durum wheat grain of the present invention is about 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, or 50 mg.

Thus, wild type durum wheat analyzed by exemplary methods described herein, was found to have a kernel weight of about 40.3 mg as compared to a high amylose durum wheat product of the invention which was found to have significantly less than 40.3 mg kernel weight, including, e.g., about 34.8 mg.

In some embodiments, the methods relate to modifying kernel hardness of durum wheat. In some embodiments, the kernel hardness of the durum wheat of the present invention is modified (e.g., increased or decreased) for about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 79%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 300%, 400%, 500%, 600%, 700%, 800%, 900%, 1000% or more compared to that of a wild-type durum wheat.

In some embodiments, the kernel hardness of the durum wheat grain of the present invention is about 50, 51, 52, 53, 54, 55, 56, 57, 58, 59, 60, 61, 62, 63, 64, 65, 66, 67, 68, 69, 70, 71, 72, 73, 74, 75, 76, 77, 79, 79, 80, 81, 82, 83, 84, 85, 86, 87, 88, 89, 90, 91, 92, 93, 94, 95, 96, 97, 98, 99, or 100.

Thus, wild type durum wheat analyzed by exemplary methods described herein, was found to have a kernel hardness of about 79 as compared to a high amylose durum wheat product of the invention which was found to have significantly more than 79 kernel hardness, including, e.g., about 89.8.

In some embodiments, the kernel hardness is measure by the methods described in Osborne, B. G., Z. Kotwal, et al. (1997). "Application of the Single-Kernel Characterization System to Wheat Receiving Testing and Quality Prediction." Cereal Chemistry Journal 74(4): 467-470, which is incorporated herein by reference in its entirety. Kernel hardness impacts milling properties of wheat. For example, the SGP1 null of the present invention may have reduced kernel hardness. Reducing kernel hardness is associated with increased break flour yield and reduced flour ash and starch damage. Milling energy would also be reduced. Increased kernel hardness is associated with increased milling energy, increased starch damage after milling and increased flour particle size.

In some embodiments, the methods relate to modifying semolina yield of durum wheat. In some embodiments, the semolina yield of the durum wheat of the present invention is modified (e.g., increased or decreased) for about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 79%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 300%, 400%, 500%, 600%, 700%, 800%, 900%, 1000% or more compared to that of a wild-type durum wheat.

In some embodiments, the semolina yield of the durum wheat of the present invention and products produced from said wheat is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 79%, 79%, 80%, 81%, 82%, 83%, 84%, 85%, 86%, 87%, 88%, 89%, 90%, 91%, 92%, 93%, 94%, 95%, 96%, 97%, 98%, or 99%.

Thus, wild type durum wheat analyzed by exemplary methods described herein, was found to have a semolina yield of about 57.9 as compared to a high amylose durum wheat product of the invention which was found to have significantly less semolina yield, including, e.g., about 56.7% semolina yield.

In some embodiments, mutations in one or more copies of one or more starch synthesis genes are integrated together to create mutant plants with double, triple, quadruple etc. mutations. Such mutants can be created by classic breeding methods.

In some embodiments, mutations described herein can be integrated into wheat species other than durum wheat by classic breeding methods, with or without the help of marker-facilitated gene transfer methods, such as *T. aestivum, T. aethiopicum, T. araraticum, T. boeoticum, T. carthlicum, T. compactum, T. dicoccoides, T. dicoccum, T. ispahanicum, T. karamyschevii, T. macha, T. militinae, T. monococcum, T. polonicum, T. spelta, T. sphaerococcum, T. timopheevii, T. turanicum, T. turgidum, T. urartu, T. vavilovii,* and *T. zhukovskyi.*

In one embodiment, mutants of a starch synthesis gene having mutations in evolutionarily conserved regions or sites can be used to produce durum wheat plants with improved or altered phenotypes. In one embodiment, mutants due to nonsense mutation (premature stop codon), can be used to produce durum wheat plants with improved or altered phenotypes. In one embodiment, mutants not in evolutionarily conserved regions or sites, can also be used to produce durum wheat plants with improved or altered phenotypes.

In some other embodiments, mutant starch synthesis genes can be integrated with other mutant genes and/or transgenes. Based on the teaching of the present invention, one skilled in the art will be able to pick preferred target genes and decide when disruption or overexpression is needed to achieve certain goals, such as mutants and/or transgenes which can generally improve plant health, plant biomass, plant resistance to biotic and abiotic factors, plant yields, wherein the final preferred fatty acid production is increased. Such mutants and/or transgenes include, but are not limited to pathogen resistance genes and genes controlling plant traits related to seed yield.

Genes encoding polypeptides that can ultimately affect starch synthesis can be modulated to achieve a desired starch production. Such polypeptides include but are not limited to, soluble starch synthases (SSS), Granule bound starch synthases (GBSS), such as GBSSI, GBSSII, ADP-glucose pyrophosphorylases (AGPases), starch branching enzymes (a.k.a., SBE, such as SBE I and SBE II), starch de-branching enzymes (a.k.a., SDBE), and starch synthases I, II, III, and IV.

The modulation can achieved through breeding methods which integrate desired alleles into a single wheat plant. The desired alleles can be either naturally occurring ones or created through mutagenesis. In some embodiments, the desired alleles result in increased activity of the encoded polypeptide in a plant cell when compared to a reference allele. For example, the desired alleles can lead to increased polypeptide concentration in a plant cell, and/or polypeptides having increased enzymatic activity and/or increased stability compared to a reference allele. In some embodiments, the desired alleles result in decreased activity of the encoded polypeptide in a plant cell when compared to a reference allele. For example, the desired alleles can be either null-mutation, or encode polypeptides having decreased activity, decreased stability, and/or being wrongfully targeted in a plant cell compared to a reference allele.

The modulation can also be achieved through introducing a transgene into a wheat variety, wherein the transgene can either overexpress a gene of interest or negatively regulate a gene of interest.

In some embodiments, one or more alleles which result in increased amylose synthesis are introduced to a wheat plant, such as alleles resulting in modified soluble starch synthase activity or modified granule-bound starch synthase activity. In some embodiments, said alleles locate in the A genome and/or the B genome of a durum wheat.

In some embodiments, one or more alleles which result in decreased amylose synthesis are introduced to a wheat plant, such as alleles resulting in modified soluble starch synthase activity or modified granule-bound starch synthase activity. In some embodiments, said alleles locate in the A genome and/or the B genome of a durum wheat.

In some embodiments, one or more alleles which result in increased amylopectin synthesis are introduced to a wheat plant, such as alleles resulting in modified SSI, SSII, and/or SSIII activity, modified starch branching enzyme (e.g., SBEI, SBEIIa and SBEIIb) activity, or modified starch debranching enzyme activity. In some embodiments, said alleles locate in the A genome and/or the B genome of a durum wheat.

In some embodiments, one or more alleles which result in decreased amylopectin synthesis are introduced to a wheat plant, such as alleles resulting in modified SSI, SSII, and/or SSIII activity, modified starch branching enzyme (e.g., SBEI, SBEIIa and SBEIIb) activity, or modified starch debranching enzyme activity. In some embodiments, said alleles locate in the A genome and/or the B genome of a durum wheat.

Methods of disrupting and/or altering a target gene have been known to one skilled in the art. These methods include, but are not limited to, mutagenesis (e.g., chemical mutagenesis, radiation mutagenesis, transposon mutagenesis, insertional mutagenesis, signature tagged mutagenesis, site-directed mutagenesis, and natural mutagenesis), knock-outs/knock-ins, antisense and RNA interference.

The present invention also provides methods of breeding wheat species producing altered levels of fatty acids in the seed oil and/or meal. In one embodiment, such methods comprise
i) making a cross between the mutant durum wheat of the present invention to a second wheat species to make F1 plants;
ii) backcrossing said F1 plants to said second wheat species;
iii) repeating backcrossing step until said mutations are integrated into the genome of said second wheat species. Optionally, such method can be facilitated by molecular markers.

The present invention provides methods of breeding species close to durum wheat, wherein said species produces altered/improved starch. In one embodiment, such methods comprise
i) making a cross between the wheat mutants of the present invention to a species close to durum wheat to make F1 plants;
ii) backcrossing said F1 plants to said species that is close to durum wheat:
iii) repeating backcrossing step until said mutations are integrated into the genome of said species that is close to durum wheat. Special techniques (e.g., somatic hybridization) may be necessary in order to successfully transfer a gene from durum wheat to another species and/or genus. Optionally, such method can be facilitated by molecular markers.

The present invention also provides unique starch compositions.

In some embodiments, provided are durum wheat starch compositions having modified starch quality compared to the starch compositions derived from a reference durum wheat species, such as a wild-type durum wheat species.

In some embodiments, provided are durum wheat starch compositions having modified gelatinization temperature compared to the starch compositions derived from a reference durum wheat species, such as a wild-type durum wheat species. In some embodiments, the durum wheat starch compositions of the present invention has modified amylopectin gelatinization peaks and/or modified enthalpy. In some embodiments, the amylopectin gelatinization temperature of the durum wheat starch of the present invention is about 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C. or more higher or lower than that of a wild-type control based on peak height on a Differential Scanning Calorimetry (DSC) thermogram, under the same heat rate, or based on a Rapid Visco Analyzer test. Increased amylose would result in increased gelatinization temperature, the temperature of amylopectin gelatinization.

Using the methods of the present application, durum wheat grains with beneficial features can be produced. Such features include but are not limited to, modified dietary fiber content, modified protein content, modified fat content, modified resistant starch content, modified ash content; and modified amylose content. In some embodiments, durum wheat grains with one or more of the following features compared to the grain made from a control durum wheat plant are created: (1) increased dietary fiber content; (2) increased protein content; (3) increased fat content; (4) increased resistance starch content; (5) increased ash content; and (6) increased amylose content. The durum wheat grain with said beneficial features can be used to produce food products, such as noodle and pasta.

Plant Transformation

The present provides transgenic wheat plants with one or more modified starch synthesis genes. The modification can be either disruption or overexpression.

Binary vector suitable for wheat transformation includes, but are not limited to the vectors described by Zhang et al., 2000 (An efficient wheat transformation procedure: transformed calli with long-term morphogenic potential for plant regeneration, Plant Cell Reports (2000) 19: 241-250), Cheng et al., 1997 (Genetic Transformation of Wheat Mediated by *Agrobacterium tumefaciens*, Plant Physiol. (1997) 115: 971-980), Abdul et al., (Genetic Transformation of Wheat (*Triticum aestivum* L): A Review, TGG 2010, Vol. 1, No. 2, pp 1-7), Pastori et al., 2000 (Age dependent transformation frequency in elite wheat varieties, J. Exp. Bot. (2001) 52 (357): 857-863), Jones 2005 (Wheat transformation: current technology and applications to grain development and composition, Journal of Cereal Science Volume 41, Issue 2, March 2005, Pages 137-147), Galovic et al., 2010 (MATURE EMBRYO-DERIVED WHEAT TRANSFORMA- TION WITH MAJOR STRESS MODULATED ANTIOXIDANT TARGET GENE, Arch. Biol. Sci., Belgrade, 62 (3), 539-546), or similar ones. Wheat plants are transformed by using any method described in the above references.

To construct the transformation vector, the region between the left and right T-DNA borders of a backbone vector is replaced with an expression cassette consisting of a constitutively expressed selection marker gene (e.g., the NptII kanamycin resistance gene) followed by one or more of the expression elements listed in Table 8 operably linked to a reporter gene (e.g., GUS or GFP). The final constructs are transferred to *Agrobacterium* for transformation into wheat plants by any of the methods described in Zhang et al., 2000, Cheng et al., 1997, Abdul et al., Pastori et al., 2000, Jones 2005, Galovic et al., 2010, U.S. Pat. No. 7,197,964 or similar ones to generate polynucleotide::GFP fusions in transgenic plants.

For efficient plant transformation, a selection method must be employed such that whole plants are regenerated from a single transformed cell and every cell of the transformed plant carries the DNA of interest. These methods can employ positive selection, whereby a foreign gene is supplied to a plant cell that allows it to utilize a substrate present in the medium that it otherwise could not use, such as mannose or xylose (for example, refer U.S. Pat. No. 5,767, 378; U.S. Pat. No. 5,994,629). More typically, however, negative selection is used because it is more efficient, utilizing selective agents such as herbicides or antibiotics that either kill or inhibit the growth of nontransformed plant cells and reducing the possibility of chimeras. Resistance genes that are effective against negative selective agents are provided on the introduced foreign DNA used for the plant transformation. For example, one of the most popular selective agents used is the antibiotic kanamycin, together with the resistance gene neomycin phosphotransferase (nptII), which confers resistance to kanamycin and related antibiotics (see, for example, Messing & Vierra, Gene 19: 259-268 (1982); Bevan et al., Nature 304:184-187 (1983)). However, many different antibiotics and antibiotic resistance genes can be used for transformation purposes (refer U.S. Pat. No. 5,034,322, U.S. Pat. No. 6,174,724 and U.S. Pat. No. 6,255,560). In addition, several herbicides and herbicide resistance genes have been used for transformation purposes, including the bar gene, which confers resistance to the herbicide phosphinothricin (White et al., Nucl Acids Res 18: 1062 (1990), Spencer et al., Theor Appl Genet 79: 625-631 (1990), U.S. Pat. No. 4,795,855, U.S. Pat. No. 5,378,824 and U.S. Pat. No. 6,107,549). In addition, the dhfr gene, which confers resistance to the anticancer agent methotrexate, has been used for selection (Bourouis et al., EMBO J. 2(7): 1099-1104 (1983).

The expression control elements used to regulate the expression of a given protein can either be the expression control element that is normally found associated with the coding sequence (homologous expression element) or can be a heterologous expression control element. A variety of homologous and heterologous expression control elements are known in the art and can readily be used to make expression units for use in the present invention. Transcription initiation regions, for example, can include any of the various opine initiation regions, such as octopine, mannopine, nopaline and the like that are found in the Ti plasmids of *Agrobacterium tumefaciens*. Alternatively, plant viral promoters can also be used, such as the cauliflower mosaic virus 19S and 35S promoters (CaMV 19S and CaMV 35S promoters, respectively) to control gene expression in a plant (U.S. Pat. Nos. 5,352,605; 5,530,196 and 5,858,742 for example). Enhancer sequences derived from the CaMV can also be utilized (U.S. Pat. Nos. 5,164,316; 5,196,525; 5,322, 938; 5,530,196; 5,352,605; 5,359,142; and 5,858,742 for example). Lastly, plant promoters such as prolifera promoter, fruit specific promoters, Ap3 promoter, heat shock promoters, seed specific promoters, etc. can also be used.

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and *Agrobacterium*-mediated transformation. See, for example, U.S. Pat. Nos. 5,405,765; 5,472,869; 5,538,877; 5,538,880; 5,550,318; 5,641,664; 5,736,369 and 5,736369; International Patent Application Publication Nos. WO2002/038779 and WO/2009/117555; Lu et al., (Plant Cell Reports, 2008, 27:273-278); Watson et al., Recombinant DNA, Scientific American Books (1992); Hinchee et al., Bio/Tech. 6:915-922 (1988); McCabe et al., Bio/Tech. 6:923-926 (1988); Toriyama et al., Bio/Tech. 6:1072-1074 (1988); Fromm et al., Bio/Tech. 8:833-839 (1990); Mullins et al., Bio/Tech. 8:833-839 (1990); Hiei et al., Plant Molecular Biology 35:205-218 (1997); Ishida et al., Nature Biotechnology 14:745-750 (1996); Zhang et al., Molecular Biotechnology 8:223-231 (1997); Ku et al., Nature Biotechnology 17:76-80 (1999); and, Raineri et al., Bio/Tech. 8:33-38 (1990)), each of which is expressly incorporated herein by reference in their entirety.

Breeding Methods

Classic breeding methods can be included in the present invention to introduce one or more mutants of the present invention into other plant varieties, or other close-related species that are compatible to be crossed with the transgenic plant of the present invention.

Open-Pollinated Populations.

The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes to flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

Mass Selection.

In mass selection, desirable individual plants are chosen, harvested, and the seed composited without progeny testing to produce the following generation. Since selection is based on the maternal parent only, and there is no control over pollination, mass selection amounts to a form of random mating with selection. As stated herein, the purpose of mass selection is to increase the proportion of superior genotypes in the population.

Synthetics.

A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (Vicia) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enter a synthetic varies widely. In practice, numbers of parental lines range from 10 to several hundred, with 100-200 being the average. Broad based synthetics formed from 100 or more clones would be expected to be more stable during seed multiplication than narrow based synthetics.

Pedigreed Varieties.

A pedigreed variety is a superior genotype developed from selection of individual plants out of a segregating population followed by propagation and seed increase of self pollinated offspring and careful testing of the genotype over several generations. This is an open pollinated method that works well with naturally self pollinating species. This method can be used in combination with mass selection in variety development. Variations in pedigree and mass selection in combination are the most common methods for generating varieties in self pollinated crops.

Hybrids.

A hybrid is an individual plant resulting from a cross between parents of differing genotypes. Commercial hybrids are now used extensively in many crops, including corn (maize), sorghum, sugarbeet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, *Commercial Hybrid Seed Production* 8:161-176, In Hybridization of Crop Plants.

Differential Scanning Calorimetry

Differential scanning calorimetry or DSC is a thermoanalytical technique in which the difference in the amount of heat required to increase the temperature of a sample and reference is measured as a function of temperature. Both the sample and reference are maintained at nearly the same temperature throughout the experiment. Generally, the temperature program for a DSC analysis is designed such that the sample holder temperature increases linearly as a function of time. The reference sample should have a well-defined heat capacity over the range of temperatures to be scanned. DSC can be used to analyze Thermal Phase Change, Thermal Glass Transition Temperature (Tg), Crystalline Melt Temperature, Endothermic Effects, Exothermic Effects, Thermal Stability, Thermal Formulation Stability, Oxidative Stability Studies, Transition Phenomena, Solid State Structure, and Diverse Range of Materials. The DSC thermogram can be used to determine Tg Glass Transition Temperature, Tm Melting point, $\Delta$ Hm Energy Absorbed (joules/gram), Tc Crystallization Point, and $\Delta$Hc Energy Released (joules/gram).

DSC can be used to measure the gelatinization of starch. See Application Brief. TA No. 6, SII Nanotechnology Inc., "Measurements of gelatinization of starch by DSC", 1980; Donovan 1979 Phase transitions of the starch-water system. Bio-polymers, 18, 263-275; Donovan, J. W., & Mapes, C. J. (1980). Multiple phase transitions of starches and Nageli amylodextrins. Starch, 32, 190-193. Eliasson, A.-C. (1980). Effect of water content on the gelatinization of wheat starch. Starch, 32, 270-272. Lund, D. B. (1984). Influence of time, temperature, moisture, ingredients and processing conditions on starch gelatinization. CRC Critical Reviews in Food Science and Nutrition, 20 (4), 249-257. Shogren. R. L. (1992). Effect of moisture content on the melting and subsequent physical aging of cornstarch. Carbohydrate Polymers, 19, 83-90. Stevens, D. J., & Elton, G. A. H. (1971). Thermal properties of the starch water system. Staerke, 23, 8-11. Wootton, M., & Bamunuarachchi, A. (1980). Application of differential scanning calorimetry to starch gelatinization. Starch, 32, 126-129. Zobel, H. F., & Gelation, X. (1984). Gelation. Gelatinization of starch and mechanical properties of starch pastes. In R. Whistler, J. N. Bemiller & E. F. Paschall, Starch: chemistry and technology (pp. 285-309). Orlando, Fla.: Academic Press. Gelatinization profile is dependent on heating rates and water contents. Unless specifically defined, the comparison in DSC between the starch from the durum wheat of the present application and the starch from a wild-type reference durum wheat is under the same heating rates and/or same water content. In some embodiments, the present application provides starch compositions having modified gelatinization temperature as measured by DSC.

DSC can be used to measure the glass transition temperature of starch. See Chinachoti, P. (1996). Characterization of thermomechanical properties in starch and cereal products. Journal of Thermal Analysis, 47, 195-213. Maurice et al. 1985 Polysaccharide-water interactions—thermal behavior of rice starch. In D. Simatos & S. L. Multon, Properties of water in foods (pp. 211-227). Dordrecht: Nilhoff; Slade, L., & Levine, H. (1987). Recent advances in starch retrogradation. In S. S. Stivala, V. Crescenzi & I. C. Dea, Industrial polysaccharides (pp. 387-430). New York: Gordon and Breach. Stepto, R. F. T., & Tomka, I. (1987). Chimia, 41 (3), 76-81. Zeleznak. K. L., & Hoseney, R. C. (1997). The glass transition in starch. Cereal Chemistry, 64 (2), 121-124. In some embodiments, the present application provides starch compositions having modified glass transition temperature as measured by DSC.

DSC can be used to measure the crystallization of starch. See Biliaderis, C. G., Page, C. M., Slade, L., & Sirett, R. R. (1985). Thermal behavior of amylose-lipid complexes. Carbohydrate Polymers, 5, 367-389. Ring, S. G., Colinna, P., I'Anson, K. J., Kalichevsky. M. T., Miles, M. J., Morris, V. J., & Orford. P. D. (1987). Carbohydrate Research, 162, 277-293. In some embodiments, the present application provides starch compositions having modified crystallization temperature as measured by DSC.

DSC can also be used to calculate the heat capacity change between the starch made from the durum wheat plants of the present application and a wild-type durum wheat plant. The heat capacity of a sample is calculated from the shift in the baseline at the starting transient:

$$Cp=dH/dt \times dt/dT$$

wherein dH/dt is the shift in the baseline of the thermogram and dt/dT is the inverse of the heating rate. The unit of the heat flow is mW or mcal/second, and the unit of heating rate can be °C./min or °C./second. In some embodiments, at the heating rate of 10° C./min, the heat capacity of the starch made from the durum wheat of the present application as measured by DSC is modified (e.g., increased or decreased) for about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 79%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 100%, 120%, 130%, 140%, 150%, 160%, 170%, 180%, 190%, 200%, 300%, 400%, 500%, 600%, 700%, 800%, 900%, 1000% or more compared to that of the starch made from a wild-type durum wheat.

This invention is further illustrated by the following examples which should not be construed as limiting. The contents of all references, patents and published patent applications cited throughout this application, as well as the Figures and the Sequence Listing, are incorporated herein by reference.

EXAMPLES

Example 1

Impacts of SSII-A Null Allele on Durum Wheat Noodle Quality

Materials and Methods

A sample of 200 durum wheat accessions was obtained from the National Small Grains Collection, Aberdeen, Id., and 55 durum wheat accessions were obtained from the International Center for Agricultural Research in the Dry Areas (ICARDA). These accessions were screened to identify accessions that exhibited a null phenotype for SGP-A1 and/or SGP-B1 using SDS-PAGE of starch granule bound proteins.

Starch Extraction

Seeds from a single genotype were ground in a Braun coffee mill (Proctor Gamble, Cincinnati. Ohio) for 10 s and then placed in a 2 ml microcentrifuge tube along with two 6.5 mm yttria stabilized zirconia ceramic balls (Stanford Materials, Irvine, Calif.) which were then agitated for 30 s in a Mini-beadbeater-96 (Biospec Products, Bartlesville, Okla.) with an oscillation distance of 3.2 cm and a shaking speed of 36 oscillations/s. The zirconia balls were removed from the tubes and 1.0 ml of 0.1 M NaCl was added to the whole grain flour which was then left to steep for 30 min. at room temperature. After 30 min., a dough ball was made by mixing the wet flour using a plastic Kontes Pellet Pestle (Kimble Chase, Vineland, N.J.) and the gluten ball was removed from the samples after pressing out the starch. The liquid starch suspension was then transferred to a new pre-weighed 2.0 ml tube and 0.5 ml ddH$_2$O was added to the remnant starch pellet in the first tube. The first tube was vortexed, left to settle for 1 min. and the liquid starch suspension transferred to the second tube. The starch suspension containing tubes were centrifuged at 5,000 g and the liquid was aspirated off. To the starch pellets, 0.5 ml of SDS extraction buffer (55 mM Tris-Cl pH 6.8, 2.3% SDS, 5% BME, 10% glycerol) was added, the samples were vortexed until suspended, and then centrifuged at 5,000 g. The SDS buffer was aspirated off and the SDS buffer extraction was repeated once more. Next, 0.5 ml of 80% CsCl was added to the starch pellets, samples were vortexed until suspended, and then centrifuged at 7,500 g. The CsCl was aspirated off and the starch pellets were washed twice with 0.5 ml ddH$_2$O, and once in acetone with centrifugation speeds of 10,000 g. After aspirating off the acetone the pellets were left to dry overnight in a fume hood.

SDS-PAGE of Starch Granule Proteins

To purified starch, 7.5 µl of SDS loading buffer (SDS extraction buffer plus bromophenol blue) was added per milligram of starch. Samples were heated for 15 min. at 70° C., centrifuged for 1 min at 10,000 g, and then 40 µl of sample was loaded on a 10% (w/v) acrylamide gel prepared using a 30% acrylamide/0.8% piperazine diacrylamide w/v stock solution. The gel had a standard 4% w/v acrylamide stacking gel prepared using a 30% acrylamide/0.8% piperazine diacrylamide w/v stock solution. Gels (for the mA to be relevant, need the gel length width and height, Andy's paper lacked that as well) were run (25 mA/gel for 45 min. and then 35 mA/gel for three hrs), silver stained following standard procedures, and photographed on a light box with a digital camera. Each line was genotyped for the presence or absence of the SGP-A1 and/or SGP-B1 protein.

Evaluation of Segregating Populations

Two accessions, PI 330546 from NSGC and IG 86304 from ICARDA lacked the SGP-A1 protein. These were both crossed to the adapted durum wheat cultivar 'Mountrail' (PVP 990266) (Elias and Miller, 2000). The populations were advanced via single seed descent to the $F_5$ generation. All lines were genotyped for the presence or absence of the SGP-A1 protein using the SDS-PAGE methods described above (FIG. 1). Following a generation of seed increase, the lines plus parents were evaluated in a randomized block split plot design with two replications. The populations were main plots and the lines within each population were subplots. Each plot was four 3 m rows spaced 30 cm apart. Plots were harvested with a plot combine. The trial was grown in separate, adjacent rain fed and irrigated experiments in 2009 and 2010 at the Arthur H. Post Field Research Laboratory near Bozeman, Mont.

Measurement of Grain, Flour and Noodle Characteristics

Flour swelling power (FSP) was measured using seeds from a field grown plot from four replications (two from rain fed and two from irrigated environments) in 2009 and a single replication in 2010. Seeds were ground in a Braun coffee mill (Proctor Gamble, Cincinnati, Ohio) for 10 s and then placed in a 2 ml tube along with two 6.5 mm zirconia balls and then agitated for 30 s in a Mini-beadbeater-96 (Biospec Products, Bartlesville, Okla.) with an oscillation distance of 3.2 cm and a shaking speed of 36 oscillations/s. Next, 30 mg of the whole wheat flour was weighed out into a 2 ml tube, and 1.5 ml of $ddH_2O$ was added. Samples were heated in a Thermomixer® (Eppendorf, Hamburg, Germany) for 30 min. at 92° C. with continuous mixing at 800 rpm. Samples were then cooled on the bench for 2 min. followed by centrifugation at 4° C./1,000 g for 10 min. after which the water was aspirated off. Tubes were then re-weighed and the flour swelling power calculated by dividing the final flour weight by the initial flour weight.

Grain, semolina, and noodle quality characteristics were determined at the Durum Wheat Quality and Pasta Processing Laboratory, Fargo, N. Dak. Kernel hardness and weight was determined using the Single Kernel Characterization System (SKCS). Kernel protein content and moisture content was determined using a Foss Infratec 1241 grain analyzer (Foss North America, Eden Prairie, Minn.). Kernel weight, grain hardness and grain protein were measured on all field grown replications from both 2009 and 2010.

For the semolina and noodle quality traits, all four field replications were measured for the 2010 trial, while grain from the two rain-fed and the two irrigated replications were composited to form two replications for the 2009 trial. Grain samples were tempered to 15.5% for 24 h and milled into semolina on a Brabender Quadrumat Jr. mill that is set up to mill durum into semolina. Semolina samples were stored in glass jars at 4° C. until used. Semolina protein content and moisture content was determined using a Foss Infratec 1241 grain analyzer. Semolina color was determined by placing semolina in a black holding cell with a quartz glass window, and color was measured with the CIE L, a, b color scale using a Minolta CR310 chromameter). L-values measure black to white (0-100); a-values measure redness when positive and greenness when negative; and b values measure yellowness when positive.

Semolina (75 g) was hydrated to 38% moisture using distilled water heated to 40° C. Hydration was done in three steps. First, semolina was mixed for 30 s at low speed using a Kitchen Aid Mixer (model, manufacturer, city, state) while the distilled water was added; second, the mixer was turned off and the hydrated semolina was stirred with a spatula for 30 s, scraping sides of the mixing bowl; and third, the hydrated semolina was mixed with the Kitchen Aid Mixer for 30 s at high speed. This resulted in crumbly dough that was rounded into a ball, placed in a plastic bag, and rested at room temperature for 20 min. The rested dough was sheeted using the sheeting attachment to the Kitchen Aid mixer. Three sheeting steps were used, always passing the dough sheet through the machine in the same direction. The sheet was passed through the widest roll gap three times, medium roll gap twice, and narrow roll gap twice. Then the sheet was passed through a fettuccini cutter and laid on trays for drying. The noodles were dried using a low temperature (40° C.) drying cycle). During the drying period, relative humidity of the dryer was decreased from 95% to 50%. The temperature was held at 40° C. for the first 12 hours, then decreased to 25° C. during the last 6 hours of the cycle.

Dried noodles had an average width of 6 mm and thickness of 1.7 mm. Color of dried noodles was measured with a Minolta CR310 chromameter. Noodles were gathered together and measured using a black plastic background. Color readings were expressed by Hunter values for L, a, and b. L-values measure black to white (0-100); a-values measure redness when positive and greenness when negative; and b values measure yellowness when positive.

Noodles (10 g, 5 cm long) were cooked in boiling distilled water (300 mL) for 18 min. Noodles were drained into a Büchner funnel, rinsed with distilled water (50 mL), and noodles were weighed. Cooking loss (% total solids weight) was measured by evaporating cooking water to dryness in a forced-air oven at 110° C. Cooked firmness was determined by measuring the work (g·cm) required to shear four cooked noodles using a TX-XT2 texture analyzer (Texture Technologies Corp., Scarsdale, N.Y.) equipped with a pasta blade. The firmness results are an average of four measurements taken for each cooked sample.

Data Analysis

Because of ample rain fall in both years, the rain-fed and irrigated trials were very similar. Therefore, the environment (rain-fed and irrigated) x block combinations were treated as blocks for each year. Analyses of variance combined across years were performed for all measured traits using a model for a randomized block split plot combined over years where the populations were main plots and lines within populations were subplots. Least squares means for each line were obtained. The subplot and subplot x population sources were partitioned into SSIIa-A class, line within SSIIa-A class and all possible interactions of these sources and with year. Blocks and the lines within a SSIIa-A class were considered random, while all other factors were considered fixed effects. Analyses were performed using the PROC MIXED procedure with the SAS/STAT software version 9.3 of the SAS System for Windows (SAS Institute Inc., Cary, N.C.). Differences between SSII-A class means for each population were estimated using the ESTIMATE statement. The lone exception was flour swelling power where the year effect was not included in the model. Linear correlations among selected traits were obtained using the line means using the PROC CORR procedure with the SAS/STAT software. The heterogeneity of relationship (slopes) between SSIIa-A allelic classes for specific pairs of variables was tested using methods outlined in Littell et al. p 240 (2002).

Results

Two genotypes were identified that lacked the SGP-A1 protein. These null genotype were designated SSIIa-Ab with the wild type designated as SSIIa-Aa. The null genotypes were crossed to Mountrail to create segregating populations. These segregating populations were evaluated in replicated trials for two years. The mean grain protein was 14.1% and 15.0% for Year 1 and Year 2. Interactions with year were in general not important, and data are presented averaged over the two years. The SSIIa-Ab class had lower FSP than the SSIIa-Ala class (Table I). That difference was larger for the PI 330546 cross than for the IG 86304 cross. The SSIIa-Ab class had harder kernels ($P<0.05$) for both crosses. Kernel weight was lower for the SSIIa-Ab class compared to the SSIIa-Aa class for the IG 86304 cross. However this difference in kernel weight was not observed for the PI 330546 cross.

The SSIIa-Ab class had significantly lower semolina yield than SSIIa-Aa class for the IG 86304 cross (Table 1). Semolina color, measured only in 2010, was not significantly affected by SSIIa-A allelic class differences. The IG 86304 and PI 330546 parents had lower FSP, higher protein, lower kernel weight, harder kernels, and lower semolina yield than the Mountrail parent (Table 1).

The relative differences between SSIIa-A allelic classes for noodle color were similar for the Hunter and CIE color scales (Table 2). The SSIIa-A allelic difference had negligible effects on noodle color traits. There was no difference between SSIIa-A allelic classes for residue or cook weight. The SSIIa-Ab class produced noodles that were more firm than the SSIIa-Aa class for the PI 330546 cross, but not for the IG 86304 cross. The result was consistent in both years (data not shown). The IG 86304 and PI 330546 parents produced noodles that were darker (Lower L) and less yellow (lower b) than the adapted Mountrail parent, both considered undesirable characteristics by consumers. These two unadapted parents with the SSII-Ab null allele produced noodles that were less firm than Mountrail.

Kernel weight was inversely related to grain hardness in both crosses and positively related with semolina yield and noodle firmness for the IG 86304 cross (Table 3). Grain protein was negatively correlated with semolina yield and FSP in both crosses. Flour swelling power was not statistically related to any of the noodle quality traits (loss, cook weight or firmness) for the IG 86304 cross, while in the PI 330546 cross FSP was negatively correlated with noodle firmness but positively correlated with cook weight meaning that as FSP declined noodles were more firm and heavier. The three noodle quality traits, noodle firmness, loss, and cook weight were highly interrelated (Table 3), with loss and cook weight being negatively correlated with firmness and cook weight and cook weight and loss being positively correlated. These relationships were consistent between the two crosses.

TABLE 1

Means for grain and semolina traits for two durum wheat recombinant inbred populations segregating for SSIIa-Aa and SSIIa-Ab alleles.

| Population | SSIIa-A genotype | No lines | Flour swelling power (g/g) | Grain protein % | Kernel weight mg | Grain hardness[a] | Semolina Yield % | Semolina L | Semolina a | Semolina b |
|---|---|---|---|---|---|---|---|---|---|---|
| Mountrail/IG 86304 | | | | | | | | | | |
| | SSIIa-Aa | 25 | 9.27 | 14.5 | 37.1 | 83.7 | 57.8 | 82.5 | −0.3967 | 18.85 |
| | SSIIa-Ab | 10 | 8.72 | 14.6 | 34.8 | 89.8 | 56.7 | 81.7 | −0.1469 | 19.37 |
| P value[b] | | | 0.02 | 0.64 | 0.02 | <0.01 | 0.03 | 0.09 | 0.2000 | 0.52 |
| Parents | | | | | | | | | | |
| Mountrail | | | 9.70 | 13.6 | 40.3 | 79.0 | 57.9 | 84.1 | −1.7225 | 23.73 |
| IG 86304 | | | 8.29 | 15.0 | 32.6 | 94.1 | 55.7 | 81.1 | 0.3211 | 17.88 |
| Mountrail/PI 330546 | | | | | | | | | | |
| | SSIIa-Aa | 22 | 9.24 | 14.5 | 36.5 | 86.2 | 57.7 | 82.0 | −0.2194 | 19.08 |
| | SSIIa-Ab | 24 | 8.26 | 14.6 | 36.6 | 87.4 | 57.3 | 81.6 | −0.1596 | 19.74 |
| P value | | | <0.01 | 0.93 | 0.86 | 0.38 | 0.34 | 0.41 | 0.6900 | 0.29 |
| Parents | | | | | | | | | | |
| Mountrail | | | 9.36 | 13.4 | 40.8 | 79.5 | 58.2 | 83.5 | −1.4525 | 23.51 |
| PI 330546 | | | 7.89 | 15.2 | 32.9 | 95.5 | 56.1 | 81.0 | 0.3900 | 17.99 |
| LSD(0.05)[c] | | | 0.66 | 0.3 | 1.7 | 2.8 | 1.3 | 1.5 | 0.4640 | 1.25 |

[a]measured with the Single Kernel Characterization System,
[b]P value for comparing SSIIa-Aa vs SSIIa-Ab null class means.
[c]Compares parent means within a cross.

TABLE 2

Means for noodle color and texture traits for two durum wheat recombinant inbred populations segregating for SSIIa-Aa and SSIIa-Ab alleles.

| Population | SSIIa-A genotype | No lines | Hunter L | Hunter a | Hunter b | CIE L | CIE a | CIE b | Residue g | Cooked Wt. g | Firmness g/g |
|---|---|---|---|---|---|---|---|---|---|---|---|
| Mountrail /IG 86304 | | | | | | | | | | | |
| | SSIIa-Aa | 25 | 59.1 | 2.4343 | 17.85 | 65.7 | 2.8088 | 25.43 | 3,83 | 256.1 | 22.61 |
| | SSIIa-Ab | 10 | 57.9 | 2.9510 | 17.59 | 64.6 | 3.4154 | 25.29 | 3.99 | 251.5 | 22.71 |
| P value[a] | | | 0.13 | 0.09 | 0.46 | 0.13 | 0.09 | 0.87 | 0.10 | 0.19 | 0.95 |

TABLE 2-continued

Means for noodle color and texture traits for two durum wheat recombinant inbred populations segregating for SSIIa-Aa and SSIIa-Ab alleles.

| Population | SSIIa-A genotype | No lines | Hunter L | Hunter a | Hunter b | CIE L | CIE a | CIE b | Residue g | Cooked Wt. g | Firmness g/g |
|---|---|---|---|---|---|---|---|---|---|---|---|
| Parents | | | | | | | | | | | |
| Mountrail | | | 62.0 | 0.8867 | 21.99 | 68.3 | 1.0268 | 32.17 | 3.90 | 251.1 | 24.64 |
| IG 86304 | | | 55.6 | 3.8948 | 16.03 | 62.4 | 4.5371 | 23.04 | 3.96 | 252.3 | 21.18 |
| Mountrail/PI 330546 | | | | | | | | | | | |
| | SSIIa-Aa | 22 | 59.4 | 2.4166 | 17.64 | 66.0 | 2.7851 | 24.99 | 3.86 | 248.9 | 23.75 |
| | SSIIa-Ab | 24 | 58.8 | 2.5055 | 17.97 | 65.8 | 2.8919 | 25.71 | 3.90 | 245.2 | 26.47 |
| P value[a] | | | 0.33 | 0.71 | 0.72 | 0.33 | 0.7 | 0.27 | 0.52 | 0.18 | 0.04 |
| Parents | | | | | | | | | | | |
| Mountrail | | | 62.5 | 0.9294 | 22.21 | 68.8 | 1.0651 | 32.41 | 3.80 | 247.7 | 25.30 |
| PI 330546 | | | 56.1 | 3.6300 | 16.11 | 62.9 | 4.2313 | 23.07 | 4.16 | 247.9 | 21.67 |
| LSD(0.05)[b] | | | 1.7 | 0.3447 | 0.54 | 1.6 | 0.4085 | 0.87 | 0.32 | 17.3 | 3.15 |

[a]P value for comparing SSIIa-Aa vs. SSIIa-Ab null class means.
[b]Compares parent means within a cross.

TABLE 3

Correlations between grain, semolina and noodles quality traits for IG86304/Mountrail (upper diagonal) and PI 330546/Mountrail (lower diagonal) durum wheat recombinant inbred populations where each is segregating for SSII-Aa and SSIIa-Ab alleles.

| | Kernel weight | Grain hardness | Protein | Flour swelling | Noodle firmness | Residue | Cooked Wt. | Semolina yield |
|---|---|---|---|---|---|---|---|---|
| Kernel weight | 1.00 | −0.75[a] | −0.20 | −0.13 | 0.37 | −0.17 | −0.10 | 0.41 |
| | | <0.01[b] | 0.25 | 0.45 | 0.03 | 0.32 | 0.59 | 0.02 |
| Grain hardness | −0.84 | 1.00 | 0.21 | −0.26 | −0.34 | 0.36 | 0.04 | −0.46 |
| | <0.01 | | 0.23 | 0.13 | 0.04 | 0.03 | 0.81 | 0.01 |
| Protein | −0.13 | 0.22 | 1.00 | −0.42 | −0.04 | 0.06 | 0.21 | −0.69 |
| | 0.40 | 0.14 | | 0.01 | 0.84 | 0.75 | 0.24 | <0.01 |
| Flour swelling | −0.02 | −0.18 | −0.39 | 1.00 | −0.24 | −0.07 | 0.19 | 0.30 |
| | 0.89 | 0.23 | 0.01 | | 0.17 | 0.70 | 0.28 | 0.09 |
| Noodle firmness | −0.11 | 0.27 | 0.47 | −0.53 | 1.00 | −0.82 | −0.79 | 0.11 |
| | 0.48 | 0.07 | 0.00 | 0.00 | | <0.01 | <0.01 | 0.55 |
| Residue | 0.29 | −0.25 | −0.25 | 0.09 | −0.66 | 1.00 | 0.67 | −0.23 |
| | 0.05 | 0.09 | 0.10 | 0.55 | <0.01 | | <0.01 | 0.18 |
| Cooked Wt. | 0.13 | −0.26 | −0.33 | 0.57 | −0.94 | 0.67 | 1.00 | −0.04 |
| | 0.39 | 0.08 | 0.02 | 0.00 | <0.01 | <0.01 | | 0.82 |
| Semolina yield | 0.07 | −0.36 | −0.67 | 0.39 | −0.38 | −0.03 | 0.29 | 1.00 |
| | 0.66 | 0.01 | <0.01 | 0.01 | 0.01 | 0.85 | 0.05 | |

[a]correlation values are in upper portion of box
[b]P value for t test of null hypothesis that correlation = 0 are in lower portions of box.

Figure 2:
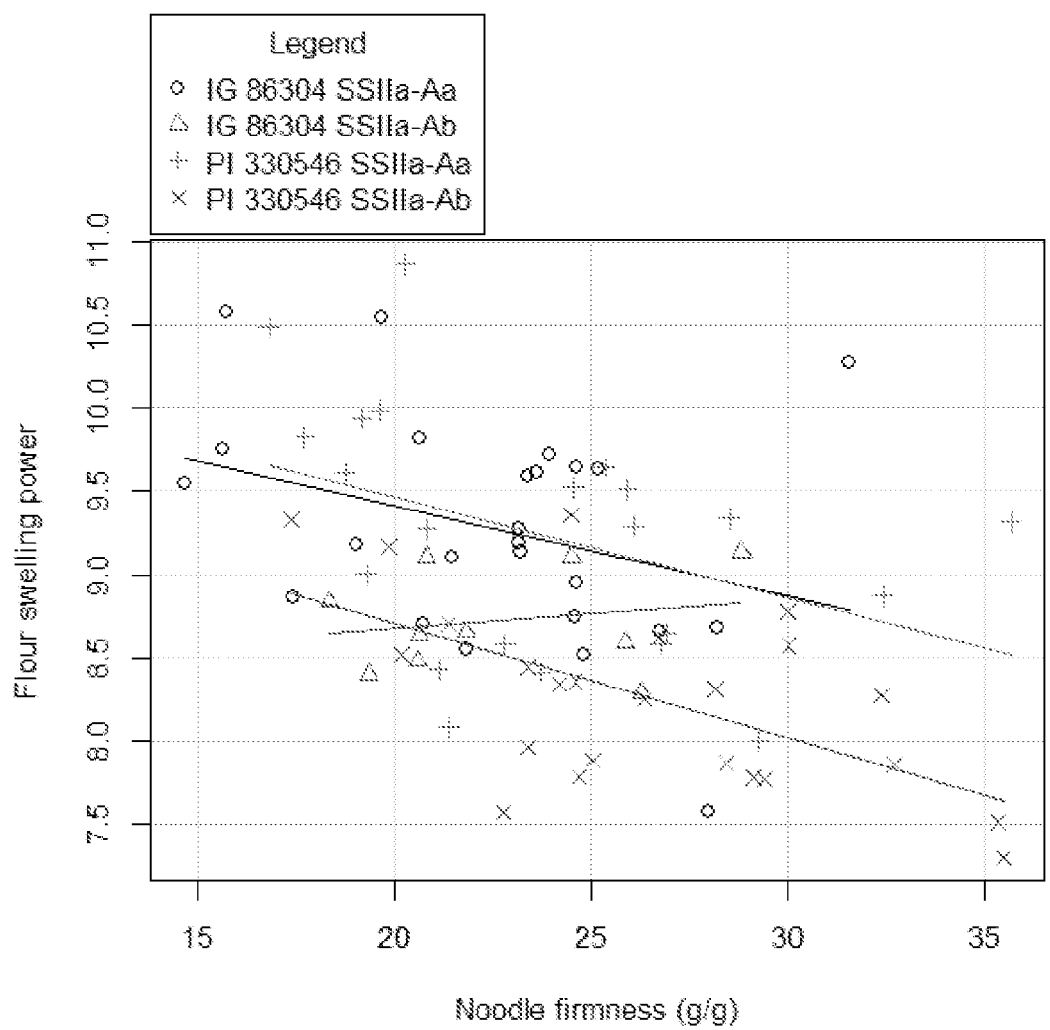
FIG. 2 depicts the relationship between flour swelling power and noodle firmness for recombinant inbred lines from Mountrail/PI 330546 and Mountrail/IG 86304 where both crosses are segregating for SSIIa-Aa versus SSIIa-Ab. Response equations are: IG 86304 SSIIa-Aa $\hat{y}$=10.489-0.054x±0.029; IG 86304 SSIIa-Ab $\hat{y}$=8.324+0.018x±0.057; PI 330546 SSIIa-Aa $\hat{y}$=10.671-0.060x±0.026; and PI 330546 SSIIa-Ab $\hat{y}$=10.080-0.069x±0.026.

The relationship between FSP and noodle firmness was also examined to determine if that relationship might differ between SSIIa-A allelic classes (FIG. 2). The FSP versus noodle firmness relation is homogeneous (slopes are not different) for the PI 330546 cross (P=0.82). The responses for the two SSIIa-A classes was also not different for the IG 86304 cross (P=0.28). The response equation for FSP versus noodle firmness for both SSIIa-A classes was $\hat{y}$=10.916−0.087x±0.021 ($r^2$=0.28) for PI 330546 cross and $\hat{y}$=10.010−0.039x±0.028 ($r^2$=0.06) for the IG 86304 cross.

Flour swelling power is measured as an indirect measure of amylose content in the segregating populations. Flour swelling tests measure the uptake of water during starch gelatinization. There is an inverse relation between flour swelling and amylose content (Crosbie et al., 1992) because of the increased water absorption of amylopectin compared to amylose (Tester & Morrison, 1990). For example Martin et al. (2004) found negative correlations of r=−0.57 in a bread wheat recombinant inbred population and r=−0.85 in a survey of bread wheat cultivars between amylose content and flour swelling power. Results showed the SSIIa-Ab class had lower swelling power than the SSIIa-Aa class in both crosses (Table I). Amylose was not determined in this study. Hogg et al. (2012) determined amylose using differential scanning calorimetry from a random SSIIa-Aa and SSIIa-Ab null line from the Mountrail/PI 330546 cross. They found amylose content was 39.22% for the SSIIa-Ab null versus 38.02% for the SSIIa-Aa wild type though the difference was not statistically different (P<0.05). They did find peak amylopectin gelatinization temperatures were significantly reduced for the SSIIa-Ab null genotype.

The SSIIa-Ab allele gave lower kernel weight and harder kernels compared to the SSIIa-Aa allele in the IG 86304 cross (Table I). Kernel weight was negatively correlated with grain hardness in both crosses meaning smaller kernels tend to be harder (Table III). The reason for the differing results for kernel weight and grain hardness between the two crosses is not clear. The IG 86304 and PI 330546 parents had similar kernel weights and both were significantly less than the Mountrail parent. The PI 330546 cross illustrated that the SSIIa-Ab1 class noodles were more firm than their SSII-Aa counterparts (Table II). However there was no difference in noodle firmness between allele classes for the IG 86304 cross even though both crosses had significant difference between the allelic classes in flour swelling. The FSP versus noodle firmness relation could not be detected as being different between the SSIIa-A classes even though the SSIIa-Ab class for the IG 86304 cross appears to respond differently than the SSIIa-Aa class and the two allelic classes from the PI 330546 cross (FIG. 2). One possible explanation might be sampling variability resulting from the small number of lines in the SSIIa-Ab null class (10) for the IG 86304 cross. Aside from starch characteristics, flour protein may influence noodle texture. In bread wheat increased flour protein leads to firmer noodles (Martin et al., 2010). Protein content does not appear to be a factor in the differing response between the two crosses as protein content was nearly the same between allelic classes for both crosses.

The SSIIa-A allelic difference was not associated with other changes in noodle quality. This indicates incorporation of the SSIIa-Ab null allele into adapted cultivars would not have detrimental effects on noodle quality. One possible advantage of the SSIIa-A4b null allele could be that the increased noodle firmness from the SSIIa-Ab allele observed in the PI 330546 may confer increased tolerance to over-cooking. Consumers may prefer products (noodles or pasta) that are firmer and more tolerant to over-cooking.

Example 2

Creation of a High-Amylose Durum Wheat Through Mutagenesis of Starch Synthase II Starch type in cereal seeds is controlled by various starch synthases. The granule bound starch synthase I "Waxy" controls amylose biosynthesis while numerous soluble starch synthases are involved in amylopectin biosynthesis. Mutations in one or more non-granule bound or "soluble" starch synthases lead to decreased amylopectin and increased amylose content. Increased amylose in turn is important as it can lower glycemic index and increase durum (*Triticum durum*) pasta quality by increasing firmness. Here we set out to determine the impact of starch synthase IIa (SSIIa or SGP-1) mutations upon durum starch. As described in Example 1, a screen of durum accessions identified two lines lacking SGP-A1, the A genome copy of SGP-1. The two lines were determined to carry the same SGP-A1 mutation, a 29 bp deletion in the first exon. The SGP-A1 nulls were each crossed with the durum variety 'Mountrail' and $F_5$ derived SGP-A1 null progeny lines were treated with EMS. From each EMS population, one SGP-B1 null mutation was recovered with each being a missense mutation. Each of the SGP-1 double nulls was found to have large increases in amylose content and reduced binding of SGP-2 and SGP-3 to the interior of starch granules. RNA-Seq was used to examine what impact the loss of SGP-1 has upon other starch biosynthetic genes. Significant increases in transcript levels of several starch biosynthetic genes were observed in SGP-1 double nulls relative to Mountrail. The resultant high amylose durums may prove useful in the creation of value added pasta with increased firmness and reduced glycemic index.

Materials and Methods
Creation and Screening of a Mutagenized Durum Wheat Population Durum wheat accessions obtained from the USDA National Small Grains Collection (NSGC, Aberdeen, Id.) and ICARDA were screened for those that were null for SGP-A1 and/or SGP-B1 using SDS-PAGE of starch granule bound proteins (see below). From the 200 NSGC *Triticum durum* core collection accessions screened, one line, PI-330546, lacked SGP-A1 and none lacked SGP-B1. From the 55 ICARDA *Triticum durum* accessions screened, one line. IG-86304, lacked SGP-A1 and none lacked SGP-B1. These two lines were crossed independently with the cultivar "Mountrail" (PVP 9900266) (Elias and Miller, 2000) and advanced via single seed decent to the $F_5$ generation. Lines homozygous for the SGP-A1 null trait that had seed and plant characteristics similar to Mountrail from each cross were then treated with ethyl methane sulfonate (EMS) as described in Feiz et al. (2009) with the exception that 0.5% EMS was used and plants were advanced two generations in the greenhouse to the $M_1:M_2$ generation. Seed from 294 Mountrail/PI-330546 Mt lines and 196 Mountrail/IG-86304 M, lines were pre-screened for potential SSIIa-B mutations using a flour swelling power test. For each line, four seeds from a single head were ground in a Braun coffee mill (Proctor Gamble, Cincinnati, Ohio) for 10 s and then placed in a 2 ml microcentrifuge tube along with two 6.5 mm yttria stabilized zirconia ceramic balls (Stanford Materials, Irvine, Calif.) and agitated for 30 s in a Mini-beadbeater-96 (Biospec Products, Bartlesville, Okla.) with an oscillation distance of 3.2 cm and a shaking speed of 36 oscillations/s. Next, 30 mg of the whole wheat flour was weighed out into a 2 ml tube and 1.5 ml of ddH$_2$O was added. Samples were heated in a Thermomixer® (Eppendorf, Hamburg, Germany) for 30 min. at 92° C. with continuous mixing at 800 rpm. Samples were then cooled at room temperature for 2 min. followed by centrifugation at 4° C./1,000 g for 10 min. after which the water was aspirated off. Tubes were then re-weighed and the flour swelling power calculated by dividing the final flour weight by the initial flour weight.

Starch Extraction

For each selected low FSP genotype along with parental controls four seeds were ground in a Braun coffee mill (Proctor Gamble, Cincinnati, Ohio) for 10 s and then placed in a 2 ml microcentrifuge tube along with two 6.5 mm zirconia balls and agitated for 30 s in a Mini-beadbeater-96. The zirconia balls were removed from the microcentrifuge tubes and 1.0 ml of 0.1 M NaCl was added to the whole grain flour which was then left to steep for 30 min. at room temperature. After 30 min., a dough ball was made by mixing the wet flour using a plastic Kontes Pellet Pestle (Kimble Chase, Vineland, N.J.) and the gluten ball was removed from the samples after pressing out the starch. The liquid starch suspension was then transferred to a new pre-weighed 2.0 ml tube and 0.5 ml ddH$_2$O was added to the remnant starch pellet in the first tube. The first tube was vortexed, left to settle for 1 min. and the liquid starch suspension transferred to the second tube. The starch suspension containing tubes were centrifuged at 5,000 g and the liquid was aspirated off. Next, 0.5 ml of SDS extraction buffer (55 mM Tris-Cl pH 6.8, 2.3% SDS, 5% BME, 10% glycerol) was added, the samples were vortexed till suspended, and then centrifuged at 5,000 g. The SDS buffer was aspirated off and the SDS buffer extraction was repeated once more. Then, 0.5 ml of 80% CsCl was added to the starch pellets, samples were vortexed till suspended, and centrifuged at 7,500 g. The CsCl was aspirated off and the starch pellets were washed twice with 0.5 ml ddH$_2$O, and once in acetone with centrifugation speeds of 10,000 g. After supernatant aspiration the starch pellets were left to dry overnight in a fume hood.

SDS-PAGE of Starch Granule Proteins

To purified starch, 7.5 μl of SDS loading buffer (SDS extraction buffer plus bromophenol blue) was added per mg of starch. Samples were heated for 15 min. at 70° C., centrifuged for 1 min at 10,000 g, and then 40 μl of sample was loaded on a 10% (w/v) acrylamide gel prepared using a 30% acrylamide/0.8% piperazine diacrylamide w/v stock solution. The gel had a standard 4% w/v acrylamide stacking gel prepared using a 30% acrylamide/0.8% piperazine diacrylamide w/v stock solution. Gels were run (25 mA/gel for 45 min. and then 35 mA/gel for three hrs), silver stained following standard procedures, and photographed on a light box with a digital camera.

PCR Screening for Mutations in SSIIa-A and SSIIa-B.

Leaf tissue from $M_2$ plants suspected of having ssIIa-B mutations and parental lines was collected at Feekes growth stage 1.3, stored at −80° C. and DNA was extracted following Riede and Anderson (1996). Coding regions of SSIIa-A and SSIIa-B were amplified from duplicate DNA samples using previously described primers and PCR conditions (Chibbar et al. 2005, Shimbata et al. 2005, Sestili et al. 2010a). Amplicons were sequenced at the University of California Berkeley Sequencing Facility and resultant DNA sequences were analyzed for single nucleotide polymorphisms using Seqman Pro in the Lasergene 10.1 Suite (DNASTAR, Madison, Wis.). The two durum high amylose (DHA) SGP-1 double mutants discovered were DHA175, from the Mountrail/PI-330546 cross and DHA55, from the Mountrail/IG-86304 cross.

Differential Scanning Calorimetry

For Mountrail, Mountrail/PI 330546 (SGP-A1 null), DHA175 and DHA55 differential scanning calorimeter (DSC) analysis was carried out using a Pyris 7 Diamond DSC (Perkin Elmer. Norwalk Conn., USA) following the methods described in Hansen et al. (2010). Three biological replicates were run in triplicate for each genotype. Approximately 10 mg of starch (actual weight was recorded) per sample was placed in a high-pressure stainless steel pan along with 55 μL of $ddH_2O$. The pan was sealed with an O-ring and cover and the starch was left to hydrate overnight at room temperature. Samples were re-weighed the next day then placed at 25° C. for two min to equilibrate before they were heated to 120° C. at 10° C./min. Heat transfer in the samples was compared to an empty stainless steel pan as a reference. The Pyris software was used to generate thermograms and calculate transition temperatures and heat of physical transition. Amylose was determined via DSC using the methods described in Polaske et al. (2005). Statistical analysis on amylose content was carried out using PROC GLM and t-tests with an alpha of 0.05 in SAS 9.0 (SAS Institute, Cary, N.C.).

Microscopic Analysis of Starch Granules.

Purified starch granules from Mountrail, Mountrail/PI 330546 (SGP-A1 null), DHA175 and DHA55 were obtained from three biological replicates per sample using the methods described above. Individual starch samples were placed on carbon tape which was then sputtered with iridium (20 mA for 30 s). Starch granules were then observed and photographed using a Zeiss Supra 55VP field emission gun-SEM (Carl Zeiss Microscopy, Peabody, Mass.).

Starch Synthesis Gene Expression Analysis Via RNA-Seq

To analyze expression levels of starch synthesis genes, developing seeds 14 days post anthesis were collected from Mountrail, DHA55, and DHA175 and stored at −80° C. For each genotype, developing seeds were collected from three separate plants, with each plant sample composed of four seeds from the middle of three different spikes (12 seeds total). Seeds were then ground to a fine powder in liquid $N_2$ using a pre-chilled mortar and pestle. Total RNA was extracted from immature kernels using an RNeasy Plant Mini Kit (Qiagen. Valencia, Calif.) after first pre-extracting each sample to remove excess starch. To accomplish this, one hundred mg of seed powder was transferred to a pre-chilled 1.5 mL tube and 0.5 mL of RNA extraction buffer (100 mM Tris pH 8.0, 150 mM LiCl, 50 mM EDTA, 1.5% (w/v) SDS, 0.15% (v/v) BME) was added and vortexed until homogenous. Next, 0.25 mL of 1:1 (v/v) phenol-chloroform (pH 4.7) was added and samples were mixed by inversion followed by a centrifugation at 13,000×g for 15 min at room temperature. The supernatant was transferred to a QIAshredder spin column and total RNA was extracted per the manufacturer's instructions. Total RNA was quantified and its quality assessed using a Bioanalyzer (Agilent Technologies, Santa Clara, Calif.). For RNA-Seq analysis, one μg of total RNA was used for the creation of cDNA libraries using TruSeq RNA-Seq library kits (Illumina, San Diego, Calif.) per the manufacturer's instructions. Amplicons from cDNA libraries were sequenced as single 50 bp reads using a LifeTech SOLiD 5500×1 (Life Technologies, Carlsbad, Calif.). RNA-Seq data was analyzed using Q-Seq in ArrayStar v5.0 (DNASTAR, Madison, Wis.). Genes of interest were selected from the NCBI database for analysis with the match settings in QSeq set to 100% for at least 40 bp with mer minimization turned off. All other settings were left to default and sequences were normalized using Reads Per Kilobase of exon model per Million mapped reads (RPKM) method. Resultant linear counts were then further normalized to the expression levels of the house keeping gene glyceraldehyde-3-phosphate dehydrogenase (Ga3pd). Student's t-tests were used to compare expression levels between Mountrail and the two ssIIa null genotypes, DHA55 and DHA175.

Results

Screening of EMS Mutagenized Durum Lines

Figure 3:
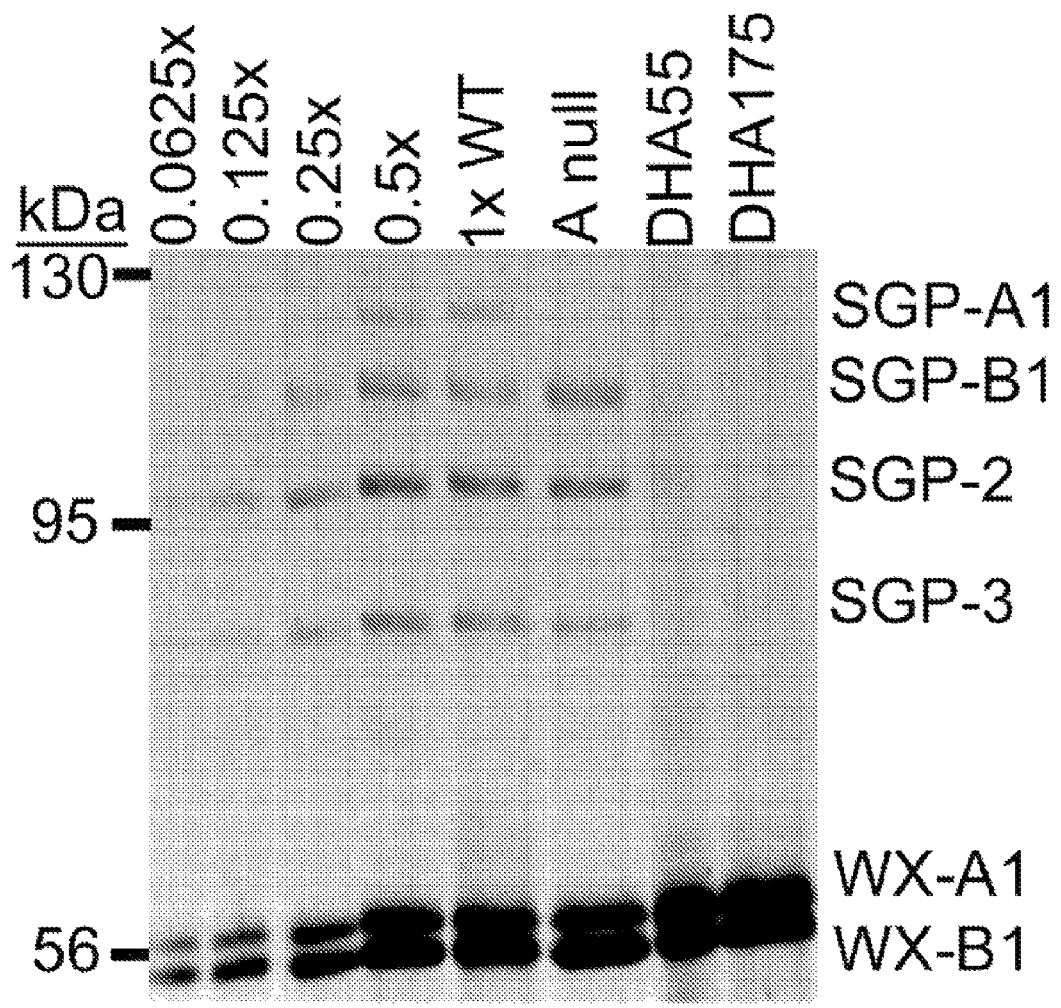
FIG. 3 depicts SDS-PAGE analysis of starch granule proteins from Mountrail/PI-330546 $F_5$ SGP-1 wild-type (WT), Mountrail/PI-330546 $F_5$ SGP-A1 null (A null) and SGP-1 double null genotypes DHA175 and DHA55. The acrylamide gel was silver stained and a dilution series of WT was used to create the loading curve. The elimination of both SGP-1 proteins in durum results in reduced binding of SGP-2 and SGP-3.

Seed from Mountrail/PI-330546 and Mountrail/IG-86304 $M_1$ lines was screened indirectly for mutations in SSIIa-B using a flour swelling power test (Table 4). Lines that had a flour swelling power of less than 6.5 were selected for analysis of SGPs via SDS-PAGE. One line from the Mountrail/PI-330546 cross, DHA175 was lacking SGP-A1/B1, SGP-2 and SGP-3 and line DHA55 from the Mountrail/IG-86304 cross had a SGP-B1 band that was approximately half the intensity of the Mountrail/IG-86304 (wild-type) control (data not shown), indicating a potential heterozygote. After growing this line another generation ($M_2$:$M_3$) it was confirmed to be a heterozygote using SDS-PAGE of the SGPs from individual plants. Starch granule proteins from Mountrail/PI-330546 (wild-type), Mountrail/PI-330546 (SGP-A1 null), DHA175 and a homozygous SGP-1 double null DHA55 were then analyzed via SDS-PAGE using a dilution series to examine the effect of the SGP-1 double nulls on the binding of the other SGPs (FIG. 3). In both DHA175 and DHA55 the SGP-A1 and SGP-B1 bands were completely missing and the SGP-2 and SGP-3 bands had an intensity that was less than 0.0625× the load of the wild-type control. The WX bands appeared normal in both the SGP-1 double null lines. In the SGP-A1 null control none of the SGP bands appeared altered compared to the wild-type control.

TABLE 4

Screening of EMS-derived lines using flour swelling power.

| Population | n‡ | FSP (g/g)§ |
|---|---|---|
| Mountrail/PI-330546 F5 (SGP-1 wild-type) | 24 | 8.4 (0.10)a |
| Mountrail/PI-330546 F5 (SGP-1A null) | 24 | 7.5 (0.10)b |
| EMS M$_1$ Mountrail/PI-330546 | 294 | 7.3 (0.29)b |
| DHA175† | 2 | 5.8 (0.15)c |
| EMS M$_1$ Mountrail/IG-86304 | 196 | 7.7 (0.05)b |
| DHA55† | 2 | 6.4 (0.20)c |

†These lines are SGP-1 double nulls.
‡N = number of lines used in analysis.
§FSP = flour swelling power measured on whole seed meal in water/flour suspension (g) over weight of flour (g).
Means followed with the same letter are not significantly different at P < 0.05 based on a Students t-test. Standard errors are in ( ).

PCR Screening for Mutations in SSIIa-A and SSIIa-B.

In the parental SGP-A1 null lines PI-330546 and IG-86304 a 29 bp deletion was discovered in the first exon at position 145-174 using the primer set Sgp-A1F3/Sgp-A1R3 (Shimbata et al. 2005). In line DHA175 a point mutation in SSIIa-B was found in the third exon at position 979 where a G/C to A/T transition occurred using the primer set Sgp-B1F1/Sgp-B1R1 (Sestili et al. 2010a). This changed the 327th amino acid from aspartic acid (GAT) to asparagine (AAT). In line DHA55 a point mutation was found in SSIIa-B in the eighth exon at position 1,864 using the primer set Sgp-B1F2/Sgp-B1R2 (Shimbata et al. 2005). This was also a G/C to A/T transition that resulted in an aspartic acid (GAC) to asparagine (AAC) change in amino acid 622.

Microscopic Analysis

Figure 4:
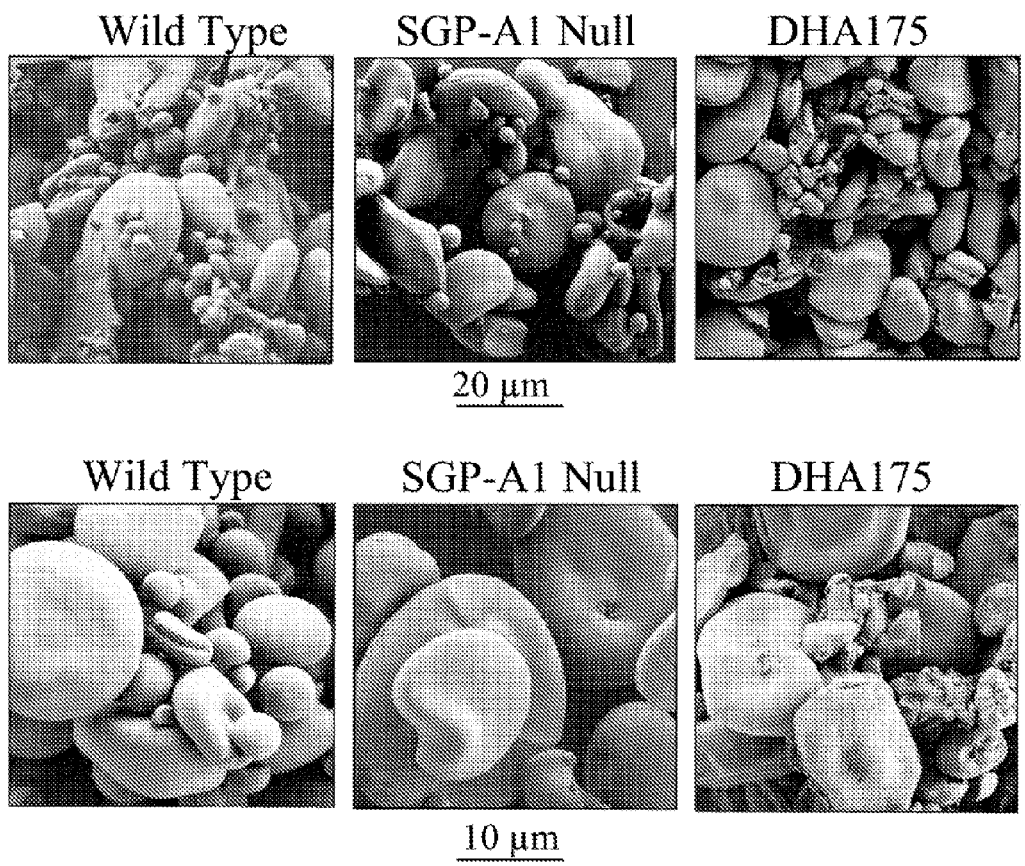
FIG. 4 depicts FEM micrograph of starch granules from Mountrail/PI-330546 F5 (SGP-1 wild-type), Mountrail/PI-330546 F5 (SGP-A1 null) and SGP-1 double null genotype DHA175.

Several images were taken at various magnification levels of each starch sample to try and obtain a representative unbiased starch granule image. In the Mountrail/PI-330546 (wild-type) line the larger A-type granules were smooth and lenticular shaped and the smaller B-type granules were spherical and smooth (FIG. 4). In the Mountrail/PI-330546 (SGP-A1 null) line the A-type starch granules had a wide range of minor deformities but appeared to maintain their smoothness and size. The B-type granules in the SGP-A1 null line were similar to those observed in the wild-type sample (FIG. 4). In the SGP-1 double null lines, DHA175 and DHA55, the A-type granules were deformed and less plump than in the wild-type and SGP-A1 null samples, and had rough or cracked surfaces (FIG. 4). Starch granule counts were not done but it appeared that the SGP-1 double null lines had fewer B-type granules which were also deformed and had a dented appearance.

Differential Scanning Calorimetry Analysis

The gelatinization properties and amylose content of SGP-1 double null and control starches was examined using DSC. The combined heat scan thermogram shows there is a clear alteration in the gelatinization of amylopectin in the SGP-1 double null lines which is represented by the first peak observed around 60° C. (FIG. 5). The SGP-1 double null lines had altered gelatinization properties over the wild type wheat lines. The SGP-1 double null lines had a significantly lower gelatinization temperature based on peak height and a dramatically smaller change in enthalpy (FIG. 5, Table 5). These data indicate a disruption in amylopectin synthesis. The second peak around 105° C. which is associated with amylose gelatinization was similar in shape and size across all samples with the SGP-1 double null lines having cooler gelatinization temperatures and larger changes in enthalpy compared to the controls (FIG. 5, Table 5). Amylose content in the SGP-A1 null line was unchanged compared to the wild-type control whereas the SGP-1 double null lines had significantly higher amylose content (Table 5). In line DHA175 there was a 41.1% increase in amylose and a 28.6% increase for DHA55.

TABLE 5

Differential scanning calorimetry analysis of SGP-1 double null starches.

| ID | Amylose (%)† | Peak 1 (° C.)† | ΔH1 (J/g)† | Peak 2 (° C.)† | ΔH2 (J/g)† |
|---|---|---|---|---|---|
| Wild-type | 38.02 (0.6)a | 64.4 (0.44) a | 8.6 (0.64) a | 103.8 (0.15) a | 4.7 (1.06) b |
| SGP-A1 null | 39.22 (2.0)a | 62.4 (0.52) b | 7.8 (0.72) a | 102.6 (0.30) b | 5.0 (0.42) ab |
| DHA175 | 53.63 (1.1)b | 57.2 (0.34) c | 2.8 (0.46) b | 102.8 (0.35) ab | 7.2 (0.25) a |
| DHA55 | 48.90 (3.2) b | 56.2 (0.15) c | 2.5 (0.80) b | 102.0 (0.40) b | 6.7 (0.95) ab |
| P value‡ | 0.0014 | <0.0001 | 0.0002 | 0.0222 | 0.1180 |

†Parameters were determined from thermograms using Pyris 7 DSC software. Values are the mean and standard error ( ) of three biological replicates. Means followed by the same letter are not significantly different based on LSD, α = 0.05.
‡Wild-type SGP-1 and SGP-A1 F$_5$ null samples came from the cross Mountrail/PI-330546.
§ANOVA P-value.

Starch Synthesis Gene Expression Analysis with RNA-Seq

To look at the RNA expression levels of genes involved with starch synthesis in the SGP-1 double null lines RNA-Seq was employed. Data from the two SGP-1 double null lines was combined and when compared to Mountrail (SGP-1 wild-type) there were several starch synthesis genes that had significant changes in transcript levels (Table 6). The deletion present in SSIIa-A in both DHA175 and DHA55 caused a dramatic reduction in SSIIa-A transcripts (Table 6). Due to the high homology of the SSIIa-A and SsIIa-B genes the few number of hits detected for SSIIa-A may have arose from areas where the two genes are 100% identical. To assess this possibility, the SSIIa-A hits were aligned to the SSIIa-A gene (Genbank:AJ269503) using Seqman NGEN (DNASTAR, Madison, Wis.). Virtually all the 40-50 bp hits aligned to segments of the gene where base pair differences existed between the two isoforms, indicating that these were fragments from SSIIa-A transcripts and not fragments of SSIIa-B transcripts (data not shown). The two independent point mutations in SSIIa-B did not produce the same effect as the deletion in SSIIa-4, on the contrary there was a significant up regulation of SSIIa-B (Table 6). Significant up regulation of transcripts was also exhibited for starch synthesis genes Wx-A1, SsI-1, SbeI-A, SbeIIa-A, SbeIIa-B, SSIII, the large subunit of AGPase, and Pho1. None of the samples showed a significant difference in transcript levels for the selected glutenin genes or any of the housekeeping genes with the exception of Cyp3 (Table 6).

TABLE 6

RNA-Seq expression analysis of starch synthesis genes in developing seeds from SGP-1 null lines and Mountrail.

| Genbank Accession | Gene | Mountrail§ | DHA55§ | DHA175§ | SGP-1 null¶ | SGP-1 Null/WT# |
|---|---|---|---|---|---|---|
| AJ269503 | Starch synthase II (Ss2a-A) | 876 (57) | 75 (22) | 44 (12) | 59 (19) | 0.07*** |
| AJ269504 | Starch synthase II (Ss2a-B) | 1,145 (117) | 2,477 (370) | 2,020 (180) | 2,249 (297) | 1.96** |
| AB019622‡ | Granule-bound starch synthase I (Wx-A1) | 4,410 (515) | 5,811 (341) | 5,723 (348) | 5,767 (309) | 1.31* |
| AB019623‡ | Granule-bound starch synthase I (Wx-B1) | 7,180(811) | 8,046 (740) | 13.039 (763) | 10,542 (1,716) | 1.47 |
| AJ292521 | Starch synthase I (SsI-1) | 827 (82) | 561 (112) | 936 (145) | 749 (166) | 0.91 |
| AJ292522 | Starch synthase I (SsI-2) | 3,158 (141) | 4,377 (274) | 5,110 (311) | 4,744 (350) | 1.50** |
| AF286318 | Starch branching enzyme I-A (Sbe1-A) | 7,329 (384) | 11,694 (1,137) | 14,523 (962) | 13,109 (1,299) | 1.79** |
| HE591389†‡ | Starch branching enzyme IIa (Sbe2a-A) | 3,629 (190) | 4,699 (472) | 5,755 (724) | 5,227 (641) | 1.44* |
| AY740401 | Starch branching enzyme IIa-B (Sbe2a-B) | 1,690 (104) | 2,442 (71) | 2,345 (295) | 2,393 (195) | 1.42* |
| AF258608 | Starch synthase III (Ss3) | 700 (27) | 894 (69) | 1,036 (84) | 965 (82) | 1.38* |
| AY044844†‡ | Starch Synthase IV (Ss4) | 21 (7) | 37 (7) | 47 (14) | 42 (10) | 1.99 |
| DQ839506 | ADP-glucose pyrophaspholase large subunit (AgpL) | 3,083 (258) | 6,237 (315) | 6,819 (503) | 6,528 (418) | 2.12*** |
| AF244997 | ADP glucose pyrophasphorylase large subunit (AgpL) | 26,631 (3,322) | 20,690 (4,399) | 29,136 (1,234) | 24,913 (3,935) | 0.94 |
| AJ301647 | Isoamylase I (Iso1) | 1,730 (74) | 2,211 (232) | 2,113 (285) | 2,162 (235) | 1.25 |
| EF137375† | Limit dextrinase debranching enzyme I (Ld1) | 1,469 (85) | 1,416 (180) | 2,520 (337) | 1,968 (424) | 1.34 |
| EU595762 | alpha-1,4-glucan phosphorylase (Pho1) | 1,654 (88) | 2,028 (53) | 2,449 (263) | 2,239 (216) | 1.35* |
| U66376 | 1,4-alpha-D-glueanotransferase | 732 (50) | 874 (144) | 1,311 (157) | 1,093 (193) | 1.49 |
| JF736013†‡ | HMW glutenin subunit (Glu-B1 Bx7) | 30,040 (3,463) | 27,288 (6,732) | 45,134 (2,445) | 36,211 (7,236) | 1.21 |
| HQ619891† | LMW glutenin subunit (LMW-5) | 675,506 (98,596) | 461,181 (29,247) | 1,300,483 (86,856) | 880,832 (271,666) | 1.30 |
| AF262983 | Cyclophilin A-2 (Cyp2) | 2,569 (234) | 3,183 (368) | 2,696 (399) | 2,939 (376) | 1.14 |
| AF262984 | Cyclophilin A-3 (Cyp3) | 954 (84) | 1,311 (169) | 2,102 (241) | 1,706 (312) | 1.79* |
| BK001238† | Ribosomal protein L3A-1 (Rpl3a-1) | 2,539 (347) | 1,944 (297) | 2,450 (182) | 2,197 (272) | 0.87 |
| DQ489316† | GTP-binding protein (Gbp-1) | 573 (56) | 702 (64) | 791 (79) | 747 (70) | 1.30 |
| FN429985 | glyceraldehyde-3-phosphate dehydrogenase (Ga3pd) | 25,582 | 25,582 | 25,582 | 25,582 | — |
| JF727656† | ubiquitin-protein ligase/zinc ion binding protein (Zfp-1) | 340 (69) | 298 (31) | 450 (61) | 374 (65) | 1.10 |
| U76896 | Beta-tubulin 5 (Tubb5) | 1,387 (86) | 1,727 (102) | 1,663 (219) | 1,695 (154) | 1.77 |

†Tissue of origin was unavailable; all other sequences came from developing endosperms.
‡Sequences are from genomic DNA with all introns removed; all other sequences were mRNA derived.
§Mean linear counts and standard errors ( ) from three biological replicates after normalization to Ga3pd.

Discussion

Our goal was to develop a high-amylose durum line through the mutagenesis of SSIIa (SGP-1). There is little natural variation at this locus as it is a key starch biosynthetic enzyme and after screening 255 *Triticum durum* accessions we only discovered two lines that were SGP-A1 null and none that were SGP-B1 null. Interestingly, the two lines that were SGP-A1 null, PI-330546 and IG-86304, carried the same 29 bp deletion located in the first exon. This deletion seemingly produces an unstable mRNA as there was a significant reduction of its transcript levels in the two SGP-1 double null lines. This is not the same deletion that was reported by Shimbata et al. (2005) for the SGP-A1 mutant in bread wheat (Yamamori and Endo 1996). The two separate point mutations created through EMS mutagenesis in SSIIa-B did not produce the same effect; in fact the expression of SSIIa-B was significantly higher in the SGP-1 double null lines compared to the cultivar Mountrail. Neither of the point mutations in SSIIa-B introduced a stop codon but the change of the effected amino acids (327 in DHA175 and 622 in DHA55) from aspartic acid to asparagine clearly affected the stability of the enzyme. It is unknown whether these amino acids are critical for the enzymes activity or if they affect the folding of the protein.

As shown in our previous studies several pleiotropic effects were observed as the result of the loss of SSII or SGP-1. Herein we demonstrate that the SGP-1 double null lines had significant increases in their amylose content from 38% to 50% (+12%). The two SGP-1 double null lines had extremely different amylopectin gelatinization peaks from the SGP-A1 null and wild-type which were characterized by a decreased enthalpy and reduced gelatinization temperature (FIG. 5, Table 5). In line DHA55 the peak for amylopectin gelatinization was almost too small to distinguish. Accordingly, the SGP-1 double null lines also had a lower flour swelling power (Table 4). These results are evidence of a disruption in amylopectin synthesis. Both types of starch granules from SGP-1 double nulls were deformed and had rough or cracked surfaces. While not statistically determined, we observed an overall decrease in the amount of B-type starch granules in the durum SGP-1 double null lines. There was an almost complete loss of other starch biosynthetic enzymes from the interior of starch granules, namely SBEII (SGP-2) and SSI (SGP-3), while GBSSI remained intact. The loss of these proteins presence in the starch granules however did not mean that these proteins were not produced. It has been shown that in the soluble fraction of the endosperm SBEII, SSI, and GBSSI accumulate at normal levels (Kosar-Hashemi et al. 2007, Morell et al. 2003). It has been hypothesized that SSs, SBEs, along with other starch biosynthetic enzymes act together in complexes in the wheat amyloplast and when one of these enzymes is disrupted it has significant effects on the other enzymes (Tetlow et al. 2004a). In the SGP-1 double null lines, this is manifested by the lack of entrapment of SSI and SBEII in the starch granule matrix. Tetlow et al. (2008) demonstrated that in bread wheat SBEII, SSI, and SSIIa interact to form a complex during starch deposition which is controlled by phosphorylation. The loss of SSII likely restricts the formation of this complex and in turn long-chain amylopectin formation and the entrapment of SBEII and SSI.

Using RNA-Seq to analyze the transcript levels of the genes involved in starch synthesis in SGP-1 double null lines there was indeed no negative effect on starch synthesis gene expression but in some cases an up-regulation. For Wx-A1, SsI-1, SbeI-A, SbeIIa-A, SbeIIa-B, SSIII, AgpL (large subunit of AGPase), and PhoI (alpha-1,4-glucan phosphorylase) there was a significant increase in the transcript levels of these genes in the SGP-1 double null lines. In general starch biosynthetic genes trended upward in expression in the SGP-1 double null lines. The up-regulation of starch biosynthetic genes after the elimination of a key enzyme has also been observed in bread wheat where SbeIIa was silenced using RNAi (Sestili et al. 2010b). Using qRT-PCT Sestili et al. (2010b) saw increases in Wx-1, SSIII, Iso1, and Ld1 transcripts but no increase for SsI, SSIIa, SbeIIb, or SbeI. The increase of starch synthesis related transcripts in the durum SGP-1 double null lines was much more moderate than those observed by Sestili et al. (2010b) and is likely due to the different methodologies used. Quantitative RT-PCR expression data presents relative differences through fold changes whereas RNA-seq provides a more precise assessment of transcript numbers. This phenomenon of starch biosynthetic genes being up-regulated when one of the critical genes is turned off through mutation or other means has yet to be fully explained. It could be that there is negative feedback that controls the expression of starch synthesis genes and the lack of SSII causes these genes to be up regulated. In SGP-1 mutants in bread wheat (Yamamori et al. 2000) and barley (Morell et al. 2003) it was noted that there was a significant decrease in starch content which seems peculiar given this up-regulation of most starch synthesis genes. However, knowing that these enzymes act in coordination it is reasonable to assume that maximum starch content is not achievable when these complexes do not form properly.

Given the high amylose content, altered gelatinization properties, and decreased flour swelling power of the two durum SGP-1 double-mutant lines presented here it is reasonable to assume that there will be significant impact on their end use quality. In an experiment where noodles were made from the Mountrail/PI-33038 F5 and Mountrail/IG-88905 F5 populations there was an increase in noodle firmness that was associated with the SGP-A1 null trait. The SPG-1 double null lines should produce a more profound effect as the amylose content of the SGP-A1 null lines was similar to the wild-type. Along with increased noodle firmness, there is a possibility that these lines will also have potential health benefits. In both human and animal trials high amylose bread wheat and barley with increased resistant starch was shown to increase overall colon health (Bird et al. 2008; Regina et al. 2006) and produce a lower glycemic index (Halstrom et al. 2011; King et al. 2008).

Example 3

Wheat Breeding Program Using the Durum Wheat Plants Having Modified Starch

Non-limiting methods for wheat breeding and agriculturally important traits (e.g., improving wheat yield, biotic stress tolerance, and abiotic stress tolerance etc.) are described in Slafer and Araus, 2007, ("Physiological traits for improving wheat yield under a wide range of conditions", Scale and Complexity in Plant Systems Research: Gene-Plant-Crop Relations, 147-156); Reynolds ("Physiological approaches to wheat breeding", *Agriculture and Consumer Protection*. Food and Agriculture Organization of the United Nations); Richard et al., ("Physiological Traits to Improve the Yield of Rainfed Wheat: Can Molecular Genetics Help", published by International Maize and Wheat Improvement Center); Reynolds et al. ("Evaluating Potential Genetic Gains in Wheat Associated with Stress-Adaptive Trait Expression in Elite Genetic Resources under Drought and Heat Stress Crop science". Crop Science 2007 47: Supplement_3: S-172-S-189); Setter et al., (Review of wheat improvement for waterlogging tolerance in Australia and India: the importance of anaerobiosis and element toxicities associated with different soils. Annals of Botany, Volume 103(2): 221-235); Foulkes et al., (Major Genetic Changes in Wheat with Potential to Affect Disease Tolerance. Phytopathology, July, Volume 96, Number 7, Pages 680-688 (doi: 10.1094/PHYTO-96-0680); Rosyara et al., 2006 (Yield and yield components response to defoliation of spring wheat genotypes with different level of resistance to *Helminthosporium* leaf blight. Journal of Institute of Agriculture and Animal Science 27. 42-48); U.S. Pat. Nos. 7,652,204, 6,197,518, 7,034,208, 7,528,297, 6,407,311; U.S. Published Patent Application Nos. 20080040826, 20090300783, 20060223707, 20110027233, 20080028480, 20090320152, 20090320151; WO/2001/029237A2; WO/2008/025097A1; and WO/2003/057848A2.

A durum wheat plant comprising modified starch or certain allele(s) of starch synthesis genes of the present invention can be self-crossed to produce offspring comprising the same phenotypes.

A durum wheat plant comprising modified starch or certain allele(s) of starch synthesis genes of the present invention ("donor plant") can also crossed with another plant ("recipient plant") to produce a F1 hybrid plant. Some of the F1 hybrid plants can be back-crossed to the recipient plant for 1, 2, 3, 4, 5, 6, 7, or more times. After each backcross, seeds are harvested and planted to select plants that comprise modified starch, and preferred traits inherited from the recipient plant. Such selected plants can be used as either a male or female plant to backcross with the recipient plant.

Example 4

Further Characterizations
Starch Content

The starch content of the SGP-1 double null lines and a wild-type control durum wheat line is measured by one or more methods as described herein, or those described in Moreels et al. (Measurement of Starch Content of Commercial Starches, Starch 39(12):414-416, 1987) or Chiang et al. (Measurement of Total and Gelatinized Starch by Glucoamylase and o-toluidine reagent, Cereal Chem. 54(3):429-435), each of which is incorporated by reference in its entirety. Starch content in the SGP-1 double null lines is expected to be slightly reduced compared to that of the wild-type control durum wheat line.

Glycemic Index

The glycemic index of the SGP-1 double null lines and a wild-type control durum wheat line is measured by one or more methods as described herein, or those described in Brouns et al. (Glycemic index methodology, Nutrition Research Reviews, 18(1):145-171, 2005), Wolever et al. (The glycemic index: methodology and clinical implications, Am. J. Clin. Nutr. 54(5):846-54, 1991), or Goni et al., A starch hydrolysis procedure to estimate glycemic index, Human Study, 17(3):427-437, 1997), each of which is incorporated by reference in its entirety.

The glycemic index, glycaemic index, or GI is the measurement of glucose (blood sugar) level increase from carbohydrate consumption. Glucose has a glycemic index of 100, by definition, and other foods have a lower glycemic index. The glycemic index of durum wheat pasta was measured by calculating the incremental area under the two-hour blood glucose response curve (AUC) following a 12-hour fast and ingestion of 50 g of available carbohydrates of DHA175 or wild-type pasta. The AUC of the test food is divided by the AUC of the standard (either glucose or white bread, giving two different definitions) and multiplied by 100. The average GI value is calculated from data collected in 5 human subjects. Both the standard and test food must contain an equal amount of available carbohydrate.

Figure 6:
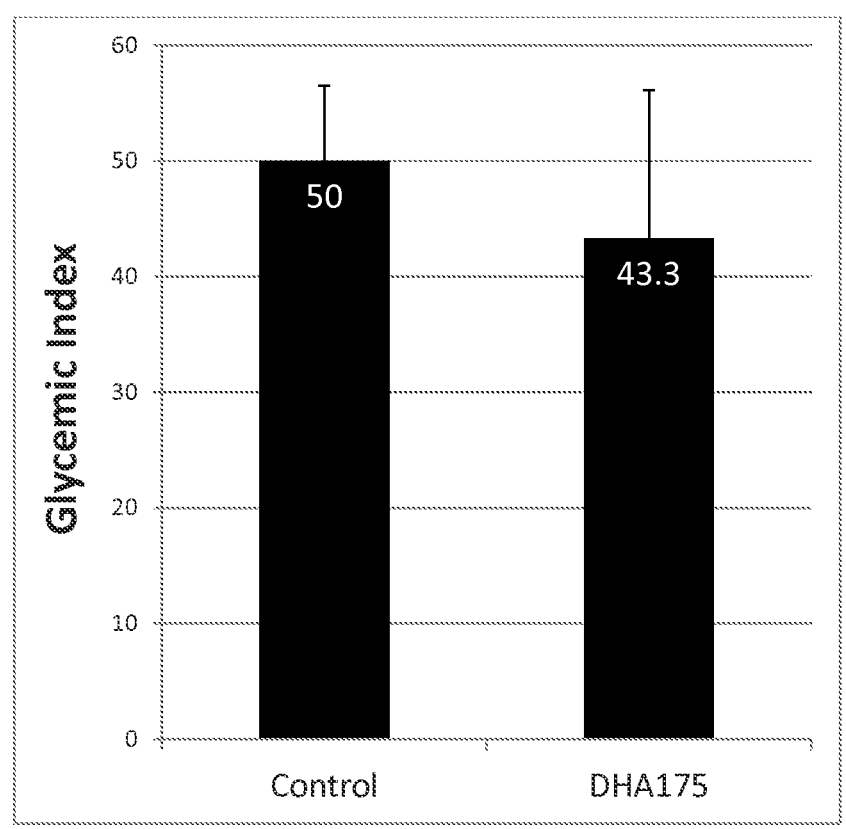
FIG. 6 depicts the glycemic index for DHA175 and wild-type control wheat pastas. The glycemic index was determined by calculating the incremental area under the two-hour blood glucose response curve (AUC) following a 12-hour fast and ingestion of DHA175 or wild-type durum pasta. DHA175 durum wheat pasta exhibits a lower glycemic index than wild-type pasta.
Figure 7:
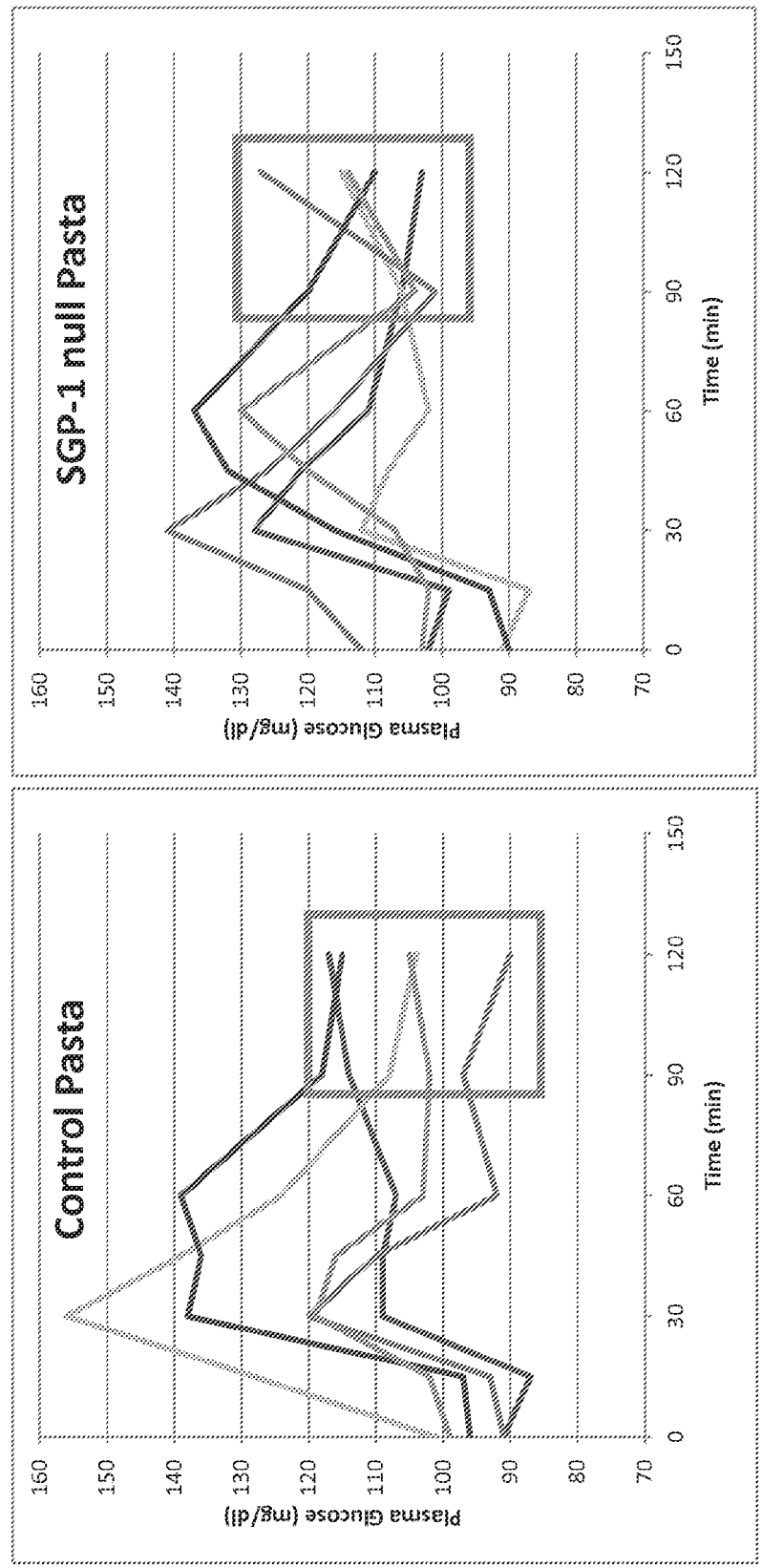
FIG. 7 depicts plasma glucose curves over the course of 120 minutes following a 12-hour fast and ingestion of DHA175 or wild-type durum pasta. DHA175 pasta also exhibited plasma glucose curves with lower glucose peaks and higher sustained glucose levels at 90 and 120 minutes when compared to wild time control durum.

The glycemic index of the DHA175 double null lines was found to be lower compared to the wild-type control durum wheat line (FIG. 6). Subjects given DHA175 pasta also exhibited plasma glucose curves with lower glucose peaks and higher sustained glucose levels at 90 and 120 minutes when compared to wild time control durum (FIG. 7). These results suggest that DHA175 pasta has a potential for greater satiety, maintaining elevated glucose levels for longer periods of time. The results also suggest the DHA175 pasta could also have health benefits over control durum wheat pasta by reducing insulin glucose spikes after consumption. Without wishing to be bound by any particular theory, the higher sustained levels of DHA175 glucose may be due to the higher protein content of the DHA175 noodles. The timing (90-120 minutes) of the increasing glucose levels in subjects fed DHA175 pasta is consistent with increases in glucose made from amino acids.

Pasta Quality

Quality of pasta made by the flour of the SGP-1 double null lines and a wild-type control durum wheat line is tested by one or more methods as described herein, or those described in Landi (Durum wheat, semolina and pasta quality characteristics for an Italian food company, Cheam-Options Mediterraneennes, pages 33-42) or Cole (Prediction and measurement of pasta quality, International Journal of Food Science and Technology, 26(2):133-151, 1991), each of which is incorporated by reference in its entirety.

Pasta firmness (Hardness, Table 7) and resistance to overcooking are measured. Pasta firmness is expected to be dramatically increased and overcooking reduced in the SGP-1 double null lines compared to that of the wild-type control durum wheat line.

Other qualitative factors of pasta can also be considered in evaluating pasta quality, including but not limited to the following: (1) the type of place of origin of the durum wheat from which the flour is produced; (2) the characteristics of the flour; (3) the manufacturing processes of kneading, drawing and drying; (4) possible added ingredients; and (5) the hygiene of preservation.

Rapid Visco Analyzer (RVA)

Starch of the SGP-1 double null lines and a wild-type control durum wheat line is tested in a Rapid Visco Analyzer (RVA) by one or more methods as described herein, or those described in Newport Scientific Method ST-00 Revision 3 (General Method for Testing Starch in Rapid Visco Analyzer, 1998), Ross (Amylose, amylopectin, and amylase: Wheat in the RVA, Oregon State University, 55$^{th}$ Conference Presentation, 2008), Bao et al., (Starch RVA profile parameters of rice are mainly controlled by Wx gene, Chinese Science Bulletin, 44(22):2047-2051, 1999), Ravi et al., (Use of Rapid Visco Analyzer (RVA) for measuring the pasting characteristics of wheat flour as influenced by additives, Journal of the Science of Food and Agriculture, 79(12): 1571-1576, 1999), or Gamel et al. (Application of the Rapid Visco Analyzer (RVA) as an Effective Rheological Tool for Measurement of β-Glucan Viscosity, 89(1):52-58, 2012), each of which is incorporated by reference in its entirety.

The SGP-1 double null lines are expected to have reduced peak viscosity compared to that of the wild-type control durum wheat line.

Resistant Starch

Resistant starch content of the SGP-1 double null lines and a wild-type control durum wheat line is tested by one or more methods as described herein, or those described in McCleary et al., (Measurement of resistant starch, J. AOAC Int. 2002, 85(3):665-675), Muir and O'Dea (Measurement of resistant starch: factors affecting the amount of starch escaping digestion in vitro, Am. J. Clin. Nutr. 56:123-127, 1992), Berry (Resistant starch: Formation and measurement of starch that survives exhaustive digestion with amylolytic enzymes during the determination of dietary fibre, Journal of Cereal Science, 4(4):301-314, 1986), Englyst et al., (Measurement of resistant starch in vitro and in vivo, British Journal of Nutrition, 75(5):749-755, 1996), each of which is incorporated by reference in its entirety.

The SGP-1 double null lines have increased resistant starch compared to the wild-type control durum wheat line in both dry and cooked pasta trials (Table 8 and Table 9).

Example 5

Noodle Firmness

DHA175 and a wild type sister line were grown in the field. The grain was cleaned, milled and the resulting semolina was used to prepare pasta. The milling and pasta processing procedures were as described previously (Carrera et al. 2007). Briefly, durum was milled to semolina using a Bühler experimental mill fitted with two Miag laboratory scale purifiers (Bühler-Miag, Minneapolis. Minn., USA). Hydrated semolina was extruded under vacuum as spaghetti using a DeMaCo semi-commercial laboratory extruder (DeFrancisci Machine Corp, Melbourne, Fla., USA). Spaghetti was dried in a laboratory pasta drier (Standard Industries, Fargo, N. Dak., USA) using a low temperature (40° C.) drying cycle.

Pasta textural properties were determined by cooking duplicate samples of each genotype in boiling deionized water until doneness. Cooking time was determined to be when each pasta was fully cooked through to the center of each piece. The DHA175 line had much reduced cooking time relative to the wild type pasta. Water absorption is the cooked weight divided by original dry weight with DHA175 having reduced water absorption. Cooking loss was determined by drying the cooking water and recording the percent solids lost with DHA175 having greater cooking loss. Pasta was allowed to drain and cool for five minutes prior to texture analysis. For texture analysis the TA.XT2 Texture Analyzer (Texture Technologies, Scarsdale, N.Y.) was used with a ¼ inch wide flat probe used to cut into six cooked pieces of pasta. Pasta firmness (hardness) is the peak force during the first compression of spaghetti by the probe. This parameter is related to sensory bite. The DHA175 spaghetti was substantially firmer than the wild type spaghetti. Noodle adhesiveness is the negative force between the first and the second peak (work necessary to overcome the attractive forces between the surface of the spaghetti and the surface of the probe), and it is theoretically related to pasta stickiness to teeth at biting. DHA175 pasta was less adhesive than the wild type pasta. Pasta cohesiveness and chewiness were measured as described in (Epstein et al., 2002). The DHA175 pasta also showed slightly lower cohesiveness with significantly higher chewiness scores (Table 7).

TABLE 7

Pasta Textural Properties

|  | Cooking Time (min.) | Hardness (g) | Adhesive-ness | Cohesive-ness | Chewiness | Water Absorption (%) | Cooking Loss (%) |
|---|---|---|---|---|---|---|---|
| DHA175 | 7:30 | 2382.85 | −1.17 | .55 | 1216.49 | 52.9 | 8.6 |
| Standard error | 0:10 | 22.52 | 1.17 | 0.01 | 43.2 | 4.3 | 0.2 |
| Wild Type | 8:45 | 1092.93 | −5.36 | 0.63 | 670.93 | 63.3 | 3.7 |
| Standard error | 0:10 | 12.14 | 0.27 | 0.001 | 6.8 | 2.7 | 0.1 |
| TTEST P | 0.001 | 0.001 | 0.01 | 0.000 | 0.000 | 0.001 | 0.01 |

Example 6

Analysis of Food Product

Pasta made from the grain of the SGP-1 double null genotype DHA175 and its wild type sister line durum wheat ("Wild Type") was further analyzed to determine their nutrient compositions. DHA175 and the Wild Type both came from F5-derived lines from the cross between Mountrail x PI330546. The unmutagenized source seed was designated as the Wild Type and then this seed was mutagenized and the resultant SGP-1 double null DHA175 was recovered. Both dried pasta and cooked pasta were analyzed.

Table 8 provides the nutrient compositions of dried pasta made from DHA175 and the wild type. The results show that the dried pasta made from the SGP-1 double null genotype DHA175 durum wheat has substantially more total dietary fiber ("TDFiber") (e.g., carbohydrates that are not digestible) than the dried pasta made from the wild type. Therefore, the products made from DHA175 are considered to have more dietary fiber that those made from the control durum wheat. In addition, the dried pasta made from DHA175 also has increased fat calorie, increased ash content, increased protein content, increased fat content, and increased resistant starch content when compared to the control durum wheat variety.

Similar results were observed when comparing cooked pasta made from DHA175 and the wild type and are provided in Table 9. The cooked samples were flash frozen in liquid nitrogen prior to submitting them to the lab for testing. Flash freezing should have prevented retrogradation.

Without wishing to be bound by any theory, the increased dietary fiber, increased protein and/or increased resistant starch in DHA175 are due to increased amylose content. Alternatively, the increased protein is simply due to the reduced starch content. Ash is also higher in the high amylose pasta made from the DHA175 durum wheat. The reduced seed plumpness in the DHA175 line makes it more difficult to separate endosperm (having lower ash and fiber) from bran (having higher ash and fiber) in the milling process. Thus, without wishing to be bound by any particular theory, the increase in fiber content in the DHA175 line may be due to a decreased endosperm to bran ratio (shrunken seeds) and reduced milling yield, which contributes to the increased fiber content in addition to the increased amylose content.

The cooking time for pasta made from the DHA175 durum wheat and the wild type control durum wheat was also determined. As provided in Table 10, the cooking time is significantly reduced when the pasta was made from the DHA175 durum wheat.

TABLE 8

Dry Pasta

| sample | Carbohydrates (%) | Calories per 100 g serving | | Moisture (%) | Ash (%) | Protein (%) | Total Dietary Fiber (%) | Fat (%) | Resistant Starch (%) | Available Carbohydrates (%) |
|---|---|---|---|---|---|---|---|---|---|---|
| | | Total Calories | Fat Calories | | | | | | | |
| DHA175-1 | 62.3 | 372.0 | 32.0 | 10.2 | 1.2 | 22.8 | 3.6 | 3.5 | 3.8 | 53.7 |
| DHA175-2 | 63.7 | 371.0 | 29.0 | 10.2 | 1.2 | 21.7 | 7.8 | 3.3 | 3.2 | 55.9 |
| Wild Type-1 | 70.2 | 365.0 | 17.0 | 10.4 | 0.7 | 16.8 | 3.0 | 1.9 | <2.0 | 67.2 |
| Wild Type-2 | 70.3 | 364.0 | 15.0 | 10.5 | 0.7 | 16.9 | 3.3 | 1.7 | <2.0 | 67.0 |
| DHA175 Avg | 63.0 | 371.5 | 30.5 | 10.2 | 1.2 | 22.3 | 8.2 | 3.4 | 3.5 | 54.8 |
| Wild Type Avg | 70.3 | 364.5 | 16.0 | 10.5 | 0.7 | 16.9 | 3.2 | 1.8 | <2.0 | 67.1 |
| P value | 0.01 | 0.01 | 0.01 | 0.01 | 0.00 | 0.01 | 0.01 | 0.01 | 0.05 | 0.01 |

TABLE 9

Cooked Pasta

| samples | Carbohydrates (%) | Calories per 100 g serving | | Moisture (%) | Ash (%) | Protein (%) | Total Dietary Fiber (%) | Fat (%) | Resistant Starch (%) | Available Carbohydrates (%) |
|---|---|---|---|---|---|---|---|---|---|---|
| | | Total Calories | Fat Calories | | | | | | | |
| DHA175-1 | 30.1 | 176.0 | 12.0 | 57.4 | 0.4 | 10.8 | 6.2 | 1.4 | 2.2 | 23.9 |
| DHA175-2 | 31.7 | 178.0 | 10.0 | 56.3 | 0.4 | 10.4 | 5.6 | 1.1 | 2.0 | 26.1 |
| Wild Type-1 | 29.8 | 156.0 | 8.0 | 61.9 | 0.1 | 7.3 | 1.6 | 0.9 | <2.0 | 28.2 |

TABLE 9-continued

Cooked Pasta

| samples | Carbohydrates (%) | Calories per 100 g serving | | Moisture (%) | Ash (%) | Protein (%) | Total Dietary Fiber (%) | Fat (%) | Resistant Starch (%) | Available Carbohydrates (%) |
|---|---|---|---|---|---|---|---|---|---|---|
| | | Total Calories | Fat Calories | | | | | | | |
| Wild Type-2 | 29.4 | 150.0 | 5.0 | 63.1 | 0.1 | 6.8 | 1.5 | 0.5 | <2.0 | 27.9 |
| DHA175 Avg | 30.9 | 177.0 | 11.0 | 56.9 | 0.4 | 10.6 | 50 | 1.2 | 2.1 | 25.0 |
| Wild Type Avg | 29.6 | 153.0 | 6.5 | 62.5 | 0.1 | 7.1 | 1.6 | 0.7 | <2.0 | 28.1 |
| P value | 0.01 | 0.01 | 0.10 | 0.01 | 0.01 | 0.01 | 0.01 | 0.06 | | 0.06 |

TABLE 10

| | Cooking Time (min.) |
|---|---|
| DHA175 | 7:30 |
| Standard error | 0:10 |
| Wild Type | 8:45 |
| Standard error | 0:10 |
| TTEST P | 0.001 |

Example 7

Segregation of SGP-A1 and SGP-B1 Mutants

SGP-1 double null genotypes DHA175 and DHA55 were each crossed with the wild type varieties 'Mountrail' and 'Divide' with the wild type varietal parent as female in each cross. ~150 F2 plants from each of the four populations were genotyped using markers specific to either the SGP-A1 or SGP-B1 mutations. Genotypes homozygous for the presence or absence of the segregating mutations were found at approximately the expected Mendelian ratio of 1/16 for each of the homozygous classes (Table 10). Genotyping revealed the segregation of SGP-1 mutations such that single (individual) SGP-A1 and single SGP-B1 wheat plants were recovered.

TABLE 10

Segregation of SGP-A1 and SGP-B1 mutations

| Cross | wt/wt | mut/wt | wt/mut | mut/mut |
|---|---|---|---|---|
| Mountrail/DHA55 | 10 | 7 | 6 | 6 |
| Mountrail/DHA175 | 8 | 8 | 6 | 9 |
| Divide/DHA55 | 11 | 12 | 5 | 7 |
| Divide/DHA175 | 14 | 15 | 10 | 10 |

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the non-limiting exemplary methods and materials are described herein.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. Nothing herein is to be construed as an admission that the present invention is not entitled to antedate such publication by virtue of prior invention.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

Altpeter F. V Vasil, V Srivastava. E Stoger, I K Vasil. Accelerated production of transgenic wheat (*Triticum aestivum* L.) plants. Plant Cell Rep 16:12-17, 1996.

Bird A. R., M. S. Vuaran, R. A. King, M. Noakes, J. Keogh, M. K. Morell, and D. L. Topping. 2008. Wholegrain foods made from a novel high-amylose barley variety (Himalaya 292) improve indices of bowel health in human subjects. Brit. J. Nutr. 99:1032-1040.

Casiraghi, M. C., Pagani, M. A., Erba, D., Marti, A., Cecchini, C., Grazia D'Egidio, M. G. Quality and nutritional properties of pasta products enriched with immature wheat grain. August 2013 Vol 64:5 544-550.

Ceoloni C, Biagetti M, Ciaffi M, Forte P, Pasquini M (1996) Wheat chromosome engineering at the 4× level: the potential of different alien gene transfers into durum wheat. Euphytica 89:87-97

Chibbar, R. N., M. Baga, S. Ganeshan, P. J. Hucl, A. Limin, C. Perron, I. Ratnayaka, A. Kapoor, V. Verma, and D. B. Fowler 2005. Carbohydrate modification to add value to wheat grain. In: Chung O. K., and Lookhart G. L. (eds.) Third international wheat quality conference, Manhattan, Kans., USA, pp 75-84.

Craig, J., J. R. Lloyd, K. Tomlinson, L. Barber, A. Edwards, T. L. Wang. C. Martin, C. L. Hedley, and A. M. Smith. 1998. Mutations in the gene encoding starch synthase II profoundly alter amylopectin structure in pea embryos. Plant Cell 10:413-426.

Denyer K., C. M. Hylton, C. F. Jenner, and A. M. Smith. 1995. Identification of Multiple Isoforms of Soluble and Granule-Bound Starch Synthase in Developing Wheat Endosperm. Planta 196:256-265.

Dexter J E, Matson, R R (1979). Changes in spaghetti protein solubility during cooking. Cereal Chem. 56: 394-397.

Feiz, L., J. M. Martin, and M. J. Giroux. 2009. Creation and functional analysis of new Puroindoline alleles in *Triticum aestivum*. Theor. and Appl. Genet. 118:247-257.

Foschia M, Peressini D, Sensidoni, A, Brennan C S (2013). The effects of dietary fibre addition on the quality of common cereal products. Journal of Cereal Science 58(2): 216-227.

Fuad T, Prabhasankar P (2010). "Role of Ingredients in Pasta Product Quality: A Review on Recent Developments." Critical Reviews in Food Science and Nutrition 50(8): 787-798.

Gilbert J, Procunier J D, Aung T (2000) Influence of the D genome in conferring resistance to fusarium head blight in spring wheat. Euphytica 114:181-186

Hallstrom, E., F. Sestili, D. Lafiandra, I. Bjorck, and E. Ostman. 2011. A novel wheat variety with elevated content of amylose increases resistant starch formation and may beneficially influence glycaemia in healthy subjects. Food & Nutr. Res. 55:7074.

Hazard, B., X. Zhang, P. Colasuonno, C. Uauy. D. M. Beckles, and J. Dubcovsky. 2012. Induced mutations in the starch branching enzyme 11 (SBEII) genes increase amylose and resistant starch content in durum wheat. Crop Sci. 52:1754-1766.

King R. A., M. Noakes. A. R. Bird, and M. K. Morell, and D. L. Topping. 2008. An extruded breakfast cereal made from a high amylose barley cultivar has a low glycemic index and lower plasma insulin response than one made from a standard barley. J. Cereal Sci. 48:526-530.

Konik-Rose C., J. Thistleton, H. Chanvrier, I. Tan, P. Halley, M. Gidley, B. Kosar-Hashemi, H. Wang, O. Larroque, J. Ikea, S. McMaugh, A. Regina, S. Rahman, M. Morell, and Z. Y. Li. 2007. Effects of starch synthase IIa gene dosage on grain, protein and starch in endosperm of wheat. Theor. Appl. Genet. 115:1053-1065.

Kosar-Hashemi, B., Z. Y. Li, O. Larroque, A. Regina, Y. M. Yamamori, M. K. Morell, and S. Rahman. 2007. Multiple effects of the starch synthase II mutation in developing wheat endosperm. Funct. Plant Biol. 34:431-438.

Lafiandra, D., F. Sestili, R. D'Ovidio, M. Janni, E. Botticella, G. Ferrazzano, M. Silvestri, R. Ranieri, and E. DeAmbrogio. 2010. Approaches for Modification of Starch Composition in Durum Wheat. Cereal Chem. 87:28-34.

Lanning S P, Blake N K, Sherman J D, Talbert L E (2008) Variable production of tetraploid and hexaploid progeny lines from spring wheat by durum wheat crosses. Crop Sci 48:199-202

Li, Z., X. Chu, G. Mouille, L. Yan. B. Kosar-Hashemi, S. Hey, J. Napier, P. Shewry, B. Clarke, R. Appels, M. K. Morell, and S. Rahman. 1999. The localization and expression of the class II starch synthases of wheat. Plant Physiol. 120:1147-1156.

Maki. K. C., C. L. Pelkman, E. T. Finocchiaro, K. M. Kelley, A. L. Lawless, A. L. Schild, and T. M. Rains. 2012. Resistant starch from high-amylose maize increases insulin sensitivity in overweight and obese men. J. Nutrit. 142:717-723.

Manthey F A, and Schorno A (2002) Physical and cooking quality of spaghetti made from whole wheat durum. Cereal Chem. 79:504-510.

Marioni, J. C., C. E. Mason, S. M. Mane, M. Stephens, and Y. Gilad. 2008. RNA-seq: an assessment of technical reproducibility and comparison with gene expression arrays. Genome Res. 18:1509-1517.

Martin A, Simpfendorfer S, Hare R A, Eberhard F S, Sutherland M W (2011) Retention of D genome chromosomes in pentaploid wheat crosses. Heredity 107:315-319

Miura, H., S. Tanii, T. Nakamura, and N. Watanabe. 1994. Genetic control of amylose content in wheat endosperm starch and differential effects of 3 Wx genes. Theoret. Appl. Genet. 89:276-280.

Morell, M. K., B. Kosar-Hashemi, M. Cmiel, M. S. Samuel, P. Chandler, S. Rahman, A. Buleon, I. L. Batey, and Z. Y. Li. 2003. Barley sex6 mutants lack starch synthase IIa activity and contain a starch with novel properties. Plant J. 34:172-184.

Nielsen, M. A., Sumner, A. K., and Whalley, L. L., Fortification of Pasta with Pea Flour and Air-Classified Pea Protein Concentrate. Cereal Chem. 57(3):203-206 1980

Nugent, A. P. 2005. Health properties of resistant starch. Nutrition Bulletin 30(1): 27-54.

Polaske, N. W., A. L. Wood, M. R. Campbell, M. C. Nagan, and L. M. Pollak. 2005. Amylose determination of native high-amylose corn starches by differential scanning calorimetry. Starch/Stärke 57:118-123.

Regina, A., A. Bird, D. Topping, S. Bowden, J. Freeman, T. Barsby, B. Kosar-Hashemi, Z. Y. Li, S. Rahman, and M. Morell. 2006. High-amylose wheat generated by RNA interference improves indices of large-bowel health in rats. Proc. Natl. Acad. Sci. USA 103:3546-3551.

Sestili, F., E. Botticella, Z. Bedo, A. Phillips, and D. Lafiandra. 2010a. Production of novel allelic variation for genes involved in starch biosynthesis through mutagenesis. Mol. Breeding 25:145-154.

Sestili, F., M. Janni, A. Doherty, E. Botticella, R. D'Ovidio, S. Masci, J. D. Jones, and D. Lafiandra. 2010b. Increasing the amylose content of durum wheat through silencing of the SBEIIa genes. BMC Plant Biol. 10:144.

Shimbata, T., T. Nakamura, P. Vrinten, M. Saito, J. Yonemaru, Y. Seto, and H. Yasuda. 2005. Mutations in wheat starch synthase II genes and PCR-based selection of a SGP-1 null line. Theoret. Appl. Genet. 111:1072-1079.

Smidansky E D, Clancy M, Meyer F D, Lanning S P, Blake N K, Talbert L E, Giroux M J (2002) Enhanced ADP-glucose pyrophosphorylase activity in wheat endosperm increase seed yield. Proc Natl Acad Sci USA 99:1724-1729

Soh, H. N., M. J. Sissons, and M. A. Turner. 2006. Effect of starch granule size distribution and elevated amylose content on durum dough rheology and spaghetti cooking quality. Cereal Chem. 83:513-519.

Tetlow, I. J., K. G. Beisel, S. Cameron, A. Makhmoudova, F. Liu, N. S. Bresolin, R. Wait, M. K. Morell, and M. J. Emes. 2008. Analysis of protein complexes in wheat amyloplasts reveals functional interactions among starch biosynthetic enzymes. Plant Physiol. 146:1878-1891.

Tetlow, I. J. 2006. Understanding storage starch biosynthesis in plants: a means to quality improvement. Can. J. Bot. 84:1167-1185.

Tetlow I. J., M. K. Morell, and M. J. Emes. 2004a. Recent developments in understanding the regulation of starch metabolism in higher plants. J. Exp. Bot. 55:2131-2145.

Tetlow, I. J., R. Wait, Z. X. Lu, R. Akkasaeng, C. G. Bowsher, S. Esposito, B. Kosar-Hashemi, M. K. Morell, and M. J. Emes. 2004b. Protein phosphorylation in amyloplasts regulates starch branching enzyme activity and protein-protein interactions. Plant Cell 16:694-708.

Thompson, D. B. 2000. Strategies for the manufacture of resistant starch. Trends in Food Sci. Tech. 11:245-253.

Yamamori, M., T. Nakamura, T. R. Endo, and T. Nagamine. 1994. Waxy protein deficiency and chromosomal location of coding genes in common wheat. Theoret. Appl. Genet. 89:179-184.

Yamamori, M., and T. R. Endo. 1996. Variation of starch granule proteins and chromosome mapping of their coding genes in common wheat. Theoret. Appl. Genet. 93:275-281.

Yamamori, M., S. Fujita, K. Hayakawa, J. Matsuki, and T. Yasui. 2000. Genetic elimination of a starch granule protein, SGP-1, of wheat generates an altered starch with apparent high amylose. Theoret. Appl. Genet. 101:21-29.

Yamamori M., M. Kato, M. Yui, and M. Kawasaki M. 2006. Resistant starch and starch pasting properties of a starch synthase IIa-deficient wheat with apparent high amylose. Aust. J. Agr. Res. 57:531-535.

Zhang, X. L., C. Colleoni, V. Ratushna, M. Sirghle-Colleoni. M. G. James, and A. M. Myers. 2004. Molecular characterization demonstrates that the Zea mays gene sugary2 codes for the starch synthase isoform SSIIa. Plant Molecular Biology 54:865-879.

Crosbie. G. B., Lambe, W. J., Tsutsui, H., and Gilmour, R. F. 1992. Further evaluation of the flour swelling volume test for identifying wheats potentially suitable for Japanese noodles. J. Cereal Sci. 15:271-280.

Elias E. M. and Miller. J. D. 2000. Registration of Mountrail durum wheat. Crop Sci. 40:1499.

Epstein, J., Morris, C. F., Huber, K. C., 2002. Instrumental texture of white salted noodles prepared from recombinant inbred lines of wheat differing in the three granule bound starch synthase (Waxy) genes. J. Cereal Sci. 35, 51-63.

Hannah, L. C. and James, M. 2008. The complexities of starch biosynthesis in cereal endosperms. Current Opinions in Biotechnology 19:160-165.

Hatcher, D. W., Dexter, J. E., Bellido, G. G., Clarke, J. M., and Anderson, M. J. 2009. Impact of genotype and environment on the quality of amber durum wheat alkaline noodles. Cereal Chem. 86:452-462.

Hung, P. V., Yamamori, M., and Morita, N. 2005. Formation of enzyme resistant starch in bread as affected by high amylose wheat flour substitutions. Cereal Chem. 82:690-694.

Lafiandra, D., Sestili, F., D'Ovidio, R., Janni, M., Botticella, E., Ferrazzano, G., Silvestri, M., Ranieri, R., and DeAmbrogio, E. 2010. Approaches for modification of starch composition in durum wheat. Cereal Chem. 87:28-34.

Li, Z., Chu. X., Mouille, G., Yan, L., Kosar-Hashemi, B., Hey, S., Napier, J., Shewry, P., Clarke, B., Appels, R., Matthew K. Morell, M. K., and Rahman, S. 1999. The localization and expression of the class II starch synthases of wheat. Plant Physiology 120:1147-1155.

Littell. R. C., Stroup, W. W., and Fruend, R. J. 2002. SAS for linear models. 4$^{th}$ ed. SAS Institute Inc, Cary, N.C.

Miura, H., and Tanii, S. 1994. Endosperm starch properties in several wheat cultivars preferred for Japanese noodles. Euphytica 72:171-175.

Martin, J. M., Berg, J. E., Hofer, P., Kephart, K. D., Nash, D. and Bruckner, P. L. 2010. Divergent selection for polyphenol oxidase and grain protein and their impacts on white salted noodle, bread and agronomic traits in wheat. Crop Sci. 50:1298-1309.

Martin, J. M., Talbert, L. E., Habernicht, D. K., Lanning, S. P., Sherman, J. D., Carlson, G., and Giroux, M. J. 2004. Reduced amylose effects on bread and white salted noodle quality. Cereal Chem. 81:188-193.

Morita, N., Maeda, T., Miyazaki, M. Yamamori, M., Miura, H., and Ohtsuka, I. 2002. Dough and baking properties of high-amylose and waxy wheat flours. Cereal Chem. 79:491-495.

Nakamura, T., Yamamori, M., Hirano, H., Hidaka, S., and Nagamine, T., 1995. Production of waxy (amylose-free) wheats. Mol. Gen. Genet. 248:253-259.

Nugent, A. P. 2005. Health properties of resistant starch. Nutrition Bulletin 30(1): 27-54.

Oda, M., Yasuda, Y., Okazaki, S., Yamauchi, Y., and Yokoyama, Y. 1980. A method of flour quality assessment for Japanese noodles. Cereal Chem. 57; 253-254.

SAS Institute. 2011. SAS 9.3 for Windows. SAS Inst., Cary, N.C.

Soh, H. N., Sissons, M. J., and Turner, M. A. 2006. Effect of starch granule size distribution and elevated amylose content on durum dough rheology and spaghetti cooking quality. Cereal Chem. 83:513-519.

Tester, R. F., and Morrison, W. R. 1990. Swelling and gelatinisation of cereal starches. I. Effects of amylopectin, amylose and lipids. Cereal Chemistry, 67, 551-557.

Thompson, D. B. 2000. Strategies for the manufacture of resistant starch. Trends Food Sci. Technol. 11:245-253.

Uauy et al. 2009 (Uauy C, Paraiso F, Colasuonno P, Tran R K, Tsai H, Berardi S, Comai L, Dubcovsky J. A modified TILLING approach to detect induced mutations in tetraploid and hexaploid wheat. BMC Plant Biol. 2009; 9:115) (cites SBEIIa: GenBank AF338431, SBEIIb: GenBank AY740398].

Vignaux, N., Doehlert, D. C., Elias, E. M. McMullen, M. S., Grant. L. A., and Kianianl, S. F. 2005. Quality of spaghetti made from full and partial waxy durum wheat. Cereal Chem. 82:93-100.

Vignaux, N., Doehlert, D. C., Hegstad, J., Elias, E. M. McMullen, M. S., Grant. L. A., and Kianianl, S. F. 2004. Grain quality characteristics and milling performance of full and partial waxy durum lines. Cereal Chem. 81:377-383.

Yamamori, M. and Endo, T. R. 1996. Variation of starch granule proteins and chromosome mapping of their coding genes in common wheat. Theor. Appl. Genet. 93:275-281.

Yamamori, M., Fujita, S. Hayakawa, K., Matsuki, J., and Yasui, T. 2000. Genetic elimination of a starch granule protein, SGP-1, of wheat generates an altered starch with apparent high amylose. Theor. Appl. Genet. 101:21-29.

Zhao, X. C., Batey, I. L., Sharp, P. J., Crosbie, G., Barclay, I., Wilson, R., Morell, M. K., and Appels, R. 1998. A single genetic locus associated with starch granule properties and noodle quality in wheat. J. Cereal Sc. 27: 7-13.

The invention claimed is:

1. A method for producing a durum wheat plant comprising one or more mutant durum starch granule protein-B1 (SGP B1) allele(s), and one or more mutant durum starch granule protein-A1 (SGP A1) allele(s), the method comprising:
   a. mutagenizing durum wheat grain to produce a mutagenized population of grain, wherein the durum wheat grain comprises a previously existing mutant durum SGP-A1 allele prior to mutagenizing, wherein the previously existing mutant durum SGP-A1 allele is not derived from a hexaploid wheat;
   b. growing one or more durum wheat plants from said mutagenized durum wheat grain;
   c. screening the resulting plants from step (b) for a newly produced mutant durum SGP-B1 allele, wherein said newly produced mutant SGP-B1 allele encodes an amino acid substitution from aspartic acid to asparagine at an amino acid position corresponding to amino acid 327 or 622 of SEQ ID No. 6; and
   d. selecting a durum wheat plant comprising the newly produced mutant durum SGP-B1 allele;
wherein the resulting plant comprises one or more mutant durum SGP-B1 allele(s) and one or more mutant durum SGP-A1 allele(s).

2. The method of claim 1, wherein the previously existing mutant durum SGP-A1 allele of step (a) comprises a 29 bp deletion as found in PI-330546 wheat line.

3. The method of claim 1, wherein the newly produced mutant durum SGP-B1 allele of step (c) encodes an amino acid substitution from aspartic acid to asparagine at an amino acid position corresponding to amino acid 327 of SEQ ID No. 6.

4. The method of claim 1, wherein the newly produced mutant durum SGP-B1 allele of step (c) encodes an amino acid substitution from aspartic acid to asparagine at an amino acid position corresponding to amino acid 622 of SEQ ID No. 6.

5. The method of claim 1, comprising an additional step of crossing the plant from step (d) with itself or with a second plant for one or more generations to produce a durum wheat plant that is homozygous for the mutant SGP-A1 and SGP-B1 alleles.

6. The method of claim 5, wherein the durum wheat plant that is homozygous for the SGP-A1 and SGP-B1 mutant alleles produces high amylose grain, and wherein the proportion of amylose in the starch of said high amylose grain is greater than about 38% as measured by differential scanning calorimetry analysis.

7. The method of claim 5, wherein the durum wheat plant that is homozygous for the SGP-A1 and SGP-B1 mutant alleles produces high amylose grain, and wherein the proportion of amylose in the starch of said high amylose grain is at least 25% higher than the proportion of amylose in the starch from grain of an appropriate durum wheat reference variety grown under similar field conditions.

8. The method of claim 5, wherein the durum wheat plant that is homozygous for the SGP-A1 and SGP-B1 mutant alleles produces high amylose grain, and wherein the proportion of amylose in the starch of said high amylose grain is at least 35% higher than the proportion of amylose in the starch from grain of an appropriate durum wheat reference variety grown under similar field conditions.

9. A method of producing a durum wheat plant comprising one or more durum starch granule protein-B1 null (SGP-B1-null) allele(s), and one or more durum starch granule protein-A1 null (SGP-A1-null) allele(s), the method comprising:
  a. crossing a durum wheat plant comprising one or more SGP-A1-null allele(s) with a second durum wheat plant comprising one or more SGP-B1-null allele(s) to produce F1 progeny plants; and
  b. selecting for an F1 progeny plant comprising at least one copy of each of the SGP-A1-null and SGP-B1-null alleles;
wherein none of the SGP-A1-null or SGP-B1-null alleles are derived from hexaploid wheat, and wherein at least one SGP-B1-null allele encodes an amino acid substitution from aspartic acid to asparagine at an amino acid position corresponding to amino acid 327 or 622 of SEQ ID No. 6.

10. The method of claim 9, wherein at least one SGP-B1-null allele encodes an amino acid substitution from aspartic acid to asparagine at an amino acid position corresponding to amino acid 327 of SEQ ID No. 6.

11. The method of claim 9, wherein at least one SGP-B1-null allele encodes an amino acid substitution from aspartic acid to asparagine at an amino acid position corresponding to amino acid 622 of SEQ ID No. 6.

12. The method of claim 9, wherein at least one SGP-A1-null allele comprises a 29 bp deletion as found in PI-330546 wheat line.

13. The method of claim 9, comprising an additional step of crossing the plant from step (b) with itself or with a second plant for one or more generations to produce a durum wheat plant that is homozygous for the SGP-A1-null and SGP-B1-null alleles.

14. The method of claim 13, wherein the durum wheat plant that is homozygous for the SGP-A1-null and SGP-B1-null alleles produces high amylose grain, and wherein the proportion of amylose in the starch of said high amylose grain is greater than about 38% as measured by differential scanning calorimetry analysis.

15. The method of claim 13, wherein the durum wheat plant that is homozygous for the SGP-A1-null and SGP-B1-null alleles produces high amylose grain, and wherein the proportion of amylose in the starch of said high amylose grain is at least 25% higher than the proportion of amylose in the starch from grain of an appropriate durum wheat reference variety grown under similar field conditions.

16. The method of claim 13, wherein the durum wheat plant that is homozygous for the SGP-A1-null and SGP-B1-null alleles produces high amylose grain, and wherein the proportion of amylose in the starch of said high amylose grain is at least 35% higher than the proportion of amylose in the starch from grain of an appropriate durum wheat reference variety grown under similar field conditions.

17. The method of claim 12, comprising an additional step of crossing the plant from step (b) with itself or with a second plant for one or more generations to produce a durum wheat plant that is homozygous for the SGP-A1-null and SGP-B1-null alleles.

18. The method of claim 17, wherein the durum wheat plant that is homozygous for the SGP-A1-null and SGP-B1-null alleles produces high amylose grain, and wherein the proportion of amylose in the starch of said high amylose grain is greater than about 38% as measured by differential scanning calorimetry analysis.

19. The method of claim 17, wherein the durum wheat plant that is homozygous for the SGP-A1-null and SGP-B1-null alleles produces high amylose grain, and wherein the proportion of amylose in the starch of said high amylose grain is at least 25% higher than the proportion of amylose in the starch from grain of an appropriate durum wheat reference variety grown under similar field conditions.

20. The method of claim 17, wherein the durum wheat plant that is homozygous for the SGP-A1-null and SGP-B1-null alleles produces high amylose grain, and wherein the proportion of amylose in the starch of said high amylose grain is at least 35% higher than the proportion of amylose in the starch from grain of an appropriate durum wheat reference variety grown under similar field conditions.

21. A method for producing a durum wheat plant comprising one or more mutant durum starch granule protein-B1 (SGP-B1) allele(s), and one or more mutant durum starch granule protein-A1 (SGP-A1) allele(s), the method comprising:
  a. mutagenizing durum wheat grain to produce a mutagenized population of grain, wherein the durum wheat grain comprises a previously existing mutant durum SGP-B1 allele prior to mutagenizing, wherein the previously existing mutant durum SGP-B1 allele is not derived from a hexaploid wheat;
  b. growing one or more durum wheat plants from said mutagenized durum wheat grain;
  c. screening the resultant plants from step (b) for a newly produced mutant durum SGP-A1 allele, wherein the newly produced mutant SGP-A1 allele comprises a 29 bp deletion as found in PI-330546 wheat line; and
  d. selecting a durum wheat plant comprising the newly produced mutant durum SGP-A1 allele;
  wherein the resulting plant comprises one or more mutant durum SGP-B1 allele(s) and one or more mutant durum SGP-A1 allele(s), and wherein at least one previously existing mutant durum SGP-B1 allele of step (a) encodes an amino acid substitution from aspartic acid to asparagine at an amino acid position corresponding to amino acid 327 or 622 of SEQ ID No. 6.

22. The method of claim 21, wherein the previously existing mutant durum SGP-B1 allele of step (a) encodes an amino acid substitution from aspartic acid to asparagine at an amino acid position corresponding to amino acid 327 of SEQ ID No. 6.

23. The method of claim 21, wherein the previously existing mutant durum SGP-B1 allele of step (a) encodes an amino acid substitution from aspartic acid to asparagine at an amino acid position corresponding to amino acid 622 of SEQ ID No. 6.

24. The method of claim 21, comprising an additional step of crossing the plant from step (d) with itself or with a second plant for one or more generations to produce a durum wheat plant that is homozygous for the mutant SGP-A1 and SGP-B1 alleles.

25. The method of claim 24, wherein the durum wheat plant that is homozygous for the SGP-A1 and SGP-B1 mutant alleles produces high amylose grain, and wherein the proportion of amylose in the starch of said high amylose grain is greater than about 38% as measured by differential scanning calorimetry analysis.

26. The method of claim 24, wherein the durum wheat plant that is homozygous for the SGP-A1 and SGP-B1 mutant alleles produces high amylose grain, and wherein the proportion of amylose in the starch of said high amylose grain is at least 25% higher than the proportion of amylose in the starch from grain of an appropriate durum wheat reference variety grown under similar field conditions.

27. The method of claim 24, wherein the durum wheat plant that is homozygous for the SGP-A1 and SGP-B1 mutant alleles produces high amylose grain, and wherein the proportion of amylose in the starch of said high amylose grain is at least 35% higher than the proportion of amylose in the starch from grain of an appropriate durum wheat reference variety grown under similar field conditions.

* * * * *